US011690413B2

(12) United States Patent
Donohoe et al.

(10) Patent No.: US 11,690,413 B2
(45) Date of Patent: Jul. 4, 2023

(54) WEARABLE ARTICLE WITH REMOVABLE MODULE

(71) Applicant: NIKE, Inc., Beaverton, OR (US)

(72) Inventors: Brendan Donohoe, Portland, OR (US); Keith Folske, Wilsonville, OR (US); Brian Kash, Portland, OR (US); Kevin Steward, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 17/685,119

(22) Filed: Mar. 2, 2022

(65) Prior Publication Data
US 2022/0240599 A1  Aug. 4, 2022

Related U.S. Application Data

(63) Continuation of application No. 16/907,884, filed on Jun. 22, 2020, now Pat. No. 11,297,883, which is a (Continued)

(51) Int. Cl.
*A41D 1/00* (2018.01)
*A61B 5/00* (2006.01)
(Continued)

(52) U.S. Cl.
CPC .......... *A41D 1/002* (2013.01); *A61B 5/02055* (2013.01); *A61B 5/681* (2013.01);
(Continued)

(58) Field of Classification Search
CPC ........ A41D 1/002; A41D 13/00; A41D 27/00; A61B 5/02055; A61B 5/6807;
(Continued)

(56) References Cited

U.S. PATENT DOCUMENTS 1,531,994 A   3/1925   Starmer
3,106,033 A   10/1963  Brewer
(Continued)

FOREIGN PATENT DOCUMENTS

AU   2002100391 A4   6/2002
CN       2708689 Y   7/2005
(Continued)

OTHER PUBLICATIONS

Sayem et al., Review on Smart Electro-Clothing Systems (SeCSs) (Year: 2020); 23 pages.
(Continued)

*Primary Examiner* — Eric Blount
(74) *Attorney, Agent, or Firm* — Banner & Witcoff, Ltd.

(57) ABSTRACT

A system includes a wearable article and a housing assembly including a receptacle defining a chamber and having an access opening providing access to the chamber to removably receive an electronic module within the chamber. The housing assembly further includes an interface having first and second electrical contacts exposed to the chamber. First and second conductive leads are connected to the electrical contacts through the bottom side of the receptacle to place the leads in electronic communication with the contacts. The housing assembly is bonded between top and bottom layers of material forming a portion of the wearable article, such that the layers are bonded to the receptacle by a bonding material.

22 Claims, 69 Drawing Sheets

Related U.S. Application Data continuation of application No. 15/951,705, filed on Apr. 12, 2018, now Pat. No. 10,687,562.

(60) Provisional application No. 62/484,725, filed on Apr. 12, 2017.

(51) Int. Cl.
| | | |
|---|---|---|
| *A61B 5/0205* | (2006.01) | |
| *G06F 1/16* | (2006.01) | |
| *A63B 71/06* | (2006.01) | |
| G06F 3/01 | (2006.01) | |
| A61B 5/11 | (2006.01) | |

(52) U.S. Cl.
CPC ........ *A61B 5/6807* (2013.01); *A63B 71/0619* (2013.01); *G06F 1/163* (2013.01); *A61B 5/11* (2013.01); *A61B 5/6805* (2013.01); *A61B 5/6806* (2013.01); *A61B 2562/0204* (2013.01); *A61B 2562/0219* (2013.01); *A61B 2562/0247* (2013.01); *A63B 2225/685* (2013.01); *G06F 3/011* (2013.01)

(58) Field of Classification Search
CPC ......... A61B 5/681; A61B 5/11; A61B 5/6805; A61B 5/6806; A61B 2562/0204; A61B 2562/0219; A61B 2562/0247; A61B 5/1125; A61B 2503/10; A63B 71/0619; A63B 2225/685; A63B 71/06; G06F 1/163; G06F 3/011
USPC ....................................... 340/573.1
See application file for complete search history.

(56) References Cited

U.S. PATENT DOCUMENTS

| | | | |
|---|---|---|---|
| 3,135,330 | A | 6/1964 | Hanson et al. |
| 3,160,910 | A | 12/1964 | Quinn |
| 4,313,445 | A | 2/1982 | Georgi |
| 4,462,116 | A | 7/1984 | Sanzone et al. |
| 4,709,307 | A | 11/1987 | Branom |
| 4,832,010 | A | 5/1989 | Lerman |
| 5,155,442 | A | 10/1992 | Mercer |
| 5,353,793 | A | 10/1994 | Bornn |
| 5,547,115 | A | 8/1996 | Ambrosius et al. |
| 5,613,756 | A | 3/1997 | Allen |
| 5,809,576 | A | 9/1998 | Huston et al. |
| 6,178,343 | B1 | 1/2001 | Bindszus et al. |
| 6,425,137 | B1 | 7/2002 | Fakhrai |
| 6,563,424 | B1 | 5/2003 | Kaario |
| 7,736,310 | B2 | 6/2010 | Taub |
| 8,105,208 | B2 | 1/2012 | Oleson et al. |
| 8,381,989 | B2 | 2/2013 | O'Neill |
| 9,141,087 | B2 | 9/2015 | Brown et al. |
| 9,521,868 | B2 | 12/2016 | Cobbett et al. |
| 9,734,477 | B2 | 8/2017 | Weast et al. |
| 10,271,587 | B2 | 4/2019 | Cobbett et al. |
| 2002/0044052 | A1 | 4/2002 | Stewart |
| 2002/0124295 | A1 | 9/2002 | Fenwick et al. |
| 2002/0163800 | A1 | 11/2002 | Hansen |
| 2004/0010199 | A1 | 1/2004 | Hashimoto et al. |
| 2004/0081025 | A1 | 4/2004 | Chen |
| 2004/0171464 | A1 | 9/2004 | Ashby et al. |
| 2004/0250933 | A1 | 12/2004 | DeMichele |
| 2005/0119833 | A1 | 6/2005 | Nanikashvili |
| 2006/0026730 | A1 | 2/2006 | Terczak |
| 2006/0075537 | A1 | 4/2006 | Tsai |
| 2006/0117458 | A1 | 6/2006 | Ishihara et al. |
| 2007/0011919 | A1 | 1/2007 | Case |
| 2007/0021269 | A1 | 1/2007 | Shum |
| 2007/0026695 | A1 | 2/2007 | Lee et al. |
| 2007/0106133 | A1 | 5/2007 | Satchwell et al. |
| 2007/0194066 | A1 | 8/2007 | Ishihara et al. |
| 2007/0261703 | A1 | 11/2007 | Gheneva et al. |
| 2007/0279852 | A1 | 12/2007 | Daniel et al. |
| 2007/0300174 | A1 | 12/2007 | Macbeth et al. |
| 2008/0045872 | A1 | 2/2008 | Bauerfeind et al. |
| 2008/0058668 | A1 | 3/2008 | Seyed Momen et al. |
| 2008/0125288 | A1 | 5/2008 | Case |
| 2008/0141436 | A1 | 6/2008 | Morgan |
| 2009/0012542 | A1 | 1/2009 | N'diaye et al. |
| 2009/0105795 | A1 | 4/2009 | Minogue et al. |
| 2009/0113089 | A1 | 4/2009 | Liu et al. |
| 2009/0292178 | A1 | 11/2009 | Ellis et al. |
| 2010/0010357 | A1 | 1/2010 | Ostrowiecki |
| 2010/0032462 | A1 | 2/2010 | Cameron et al. |
| 2010/0063652 | A1 | 3/2010 | Anderson |
| 2010/0268056 | A1 | 10/2010 | Picard et al. |
| 2011/0025195 | A1 | 2/2011 | Govender |
| 2011/0057003 | A1 | 3/2011 | Wysocki |
| 2011/0199779 | A1 | 8/2011 | Chu |
| 2011/0205161 | A1 | 8/2011 | Myers et al. |
| 2011/0235311 | A1 | 9/2011 | Stone |
| 2011/0241627 | A1 | 10/2011 | Arai et al. |
| 2012/0029299 | A1 | 2/2012 | DeRemer et al. |
| 2012/0035426 | A1 | 2/2012 | Mielcarz et al. |
| 2012/0080462 | A1 | 4/2012 | Hajarian |
| 2012/0099298 | A1 | 4/2012 | Hsu |
| 2012/0136231 | A1 | 5/2012 | Markel |
| 2012/0174278 | A1 | 7/2012 | Spivak |
| 2012/0229248 | A1 | 9/2012 | Parshionikar et al. |
| 2012/0246795 | A1 | 10/2012 | Scheffler et al. |
| 2012/0296174 | A1 | 11/2012 | McCombie et al. |
| 2013/0131484 | A1 | 5/2013 | Pernu et al. |
| 2013/0237882 | A1 | 9/2013 | Niemimaki |
| 2013/0267854 | A1 | 10/2013 | Johnson et al. |
| 2013/0313914 | A1 | 11/2013 | Hou |
| 2014/0012161 | A1 | 1/2014 | Ross, Jr. |
| 2014/0107493 | A1 | 4/2014 | Yuen et al. |
| 2014/0131402 | A1 | 5/2014 | Holmes |
| 2014/0176944 | A1 | 6/2014 | Addison et al. |
| 2014/0189928 | A1 | 7/2014 | Oleson et al. |
| 2014/0212706 | A1 | 7/2014 | Ro et al. |
| 2014/0213863 | A1 | 7/2014 | Loseu et al. |
| 2014/0213917 | A1 | 7/2014 | Hobeika et al. |
| 2014/0236037 | A1 | 8/2014 | Banet et al. |
| 2014/0243618 | A1 | 8/2014 | Charles, Jr. et al. |
| 2014/0268685 | A1 | 9/2014 | McLisky |
| 2014/0276236 | A1 | 9/2014 | Swain et al. |
| 2014/0278125 | A1 | 9/2014 | Balakrishnan et al. |
| 2014/0316305 | A1 | 10/2014 | Venkatraman et al. |
| 2014/0358473 | A1 | 12/2014 | Goel et al. |
| 2015/0011099 | A1 | 1/2015 | Kim et al. |
| 2015/0031964 | A1 | 1/2015 | Bly et al. |
| 2015/0148619 | A1 | 5/2015 | Berg et al. |
| 2015/0164349 | A1 | 6/2015 | Gopalakrishnan et al. |
| 2015/0169074 | A1 | 6/2015 | Ataee et al. |
| 2015/0182160 | A1 | 7/2015 | Kim et al. |
| 2015/0190072 | A1 | 7/2015 | Armstrong |
| 2015/0257708 | A1 | 9/2015 | Winokur et al. |
| 2015/0267911 | A1 | 9/2015 | Cushnie |
| 2015/0302158 | A1 | 10/2015 | Morris et al. |
| 2015/0366098 | A1 | 12/2015 | Lapetina et al. |
| 2015/0370333 | A1 | 12/2015 | Ataee et al. |
| 2016/0021945 | A1 | 1/2016 | Richmond |
| 2016/0058375 | A1 | 3/2016 | Rothkopf |
| 2016/0135516 | A1 | 5/2016 | Cobbett et al. |
| 2016/0135522 | A1 | 5/2016 | Rothschild et al. |
| 2016/0135743 | A1 | 5/2016 | Cobbett et al. |
| 2016/0136882 | A1 | 5/2016 | Cobbett et al. |
| 2016/0150958 | A1 | 6/2016 | Kranz |
| 2016/0187391 | A1 | 6/2016 | Ye et al. |
| 2016/0192516 | A1 | 6/2016 | Thompson |
| 2016/0192716 | A1 | 7/2016 | Lee |
| 2016/0206083 | A1 | 7/2016 | Gomez et al. |
| 2016/0209016 | A1 | 7/2016 | Bernstein |
| 2016/0226286 | A1 | 8/2016 | Xiang |
| 2016/0249698 | A1 | 9/2016 | Berzowska et al. |
| 2016/0288999 | A1 | 10/2016 | Caveney et al. |
| 2016/0338441 | A1 | 11/2016 | London |
| 2016/0349790 | A1 | 12/2016 | Connor |
| 2016/0374608 | A1 | 12/2016 | Dugan |

(56) References Cited

U.S. PATENT DOCUMENTS

| | | |
|---|---|---|
| 2017/0095692 A1 | 4/2017 | Chang et al. |
| 2017/0100300 A1 | 4/2017 | Rapp et al. |
| 2017/0126053 A1 | 5/2017 | Lai |
| 2017/0172504 A1 | 6/2017 | Lee et al. |
| 2017/0332442 A1 | 11/2017 | Strecker |
| 2018/0003579 A1 | 1/2018 | Esposito et al. |
| 2018/0042550 A1 | 2/2018 | Zhang |
| 2018/0184727 A1 | 7/2018 | Petruschka et al. |
| 2018/0242658 A1 | 8/2018 | Dal Lago et al. |
| 2018/0279889 A1 | 10/2018 | Lee |
| 2018/0295895 A1 | 10/2018 | Donohoe et al. |
| 2018/0295896 A1 | 10/2018 | Donohoe et al. |
| 2018/0295897 A1 | 10/2018 | Donohoe et al. |
| 2019/0159727 A1 | 5/2019 | Macagno et al. |
| 2020/0315267 A1 | 10/2020 | Donohoe et al. |
| 2022/0240599 A1 | 8/2022 | Donohoe et al. |

FOREIGN PATENT DOCUMENTS

| | | |
|---|---|---|
| CN | 2774203 Y | 4/2006 |
| CN | 101288517 A | 10/2008 |
| CN | 101800499 A | 8/2010 |
| CN | 202489245 U | 10/2012 |
| CN | 203505634 U | 4/2014 |
| CN | 203709336 U | 7/2014 |
| CN | 104969047 A | 10/2015 |
| CN | 105722419 A | 6/2016 |
| CN | 205285056 U | 6/2016 |
| EP | 1559335 A2 | 8/2005 |
| EP | 2260910 A1 | 12/2010 |
| JP | H03015439 A | 1/1991 |
| JP | H09322882 A | 12/1997 |
| JP | H11081017 A | 3/1999 |
| JP | 2001112725 A | 4/2001 |
| JP | 3106033 U | 12/2004 |
| JP | 2005194671 A | 7/2005 |
| JP | 2006312010 A | 11/2006 |
| JP | 2007521030 A | 8/2007 |
| JP | 3135330 U | 9/2007 |
| JP | 2008520841 A | 6/2008 |
| JP | 2008541311 A | 11/2008 |
| JP | 2009536694 A | 10/2009 |
| JP | 2009280951 A | 12/2009 |
| JP | 2010059567 A | 3/2010 |
| JP | 2010517657 A | 5/2010 |
| JP | 2011136182 A | 7/2011 |
| JP | 2011526518 A | 10/2011 |
| JP | 2011527588 A | 11/2011 |
| JP | 2012071054 A | 4/2012 |
| JP | 2012524640 A | 10/2012 |
| JP | 2013192877 A | 9/2013 |
| JP | 2014076113 A | 5/2014 |
| JP | 2014180328 A | 9/2014 |
| JP | 2015511840 A | 4/2015 |
| JP | 2016034579 A | 3/2016 |
| JP | 2016041253 A | 3/2016 |
| KR | 2014-0024845 A | 3/2014 |
| KR | 20140097681 A | 8/2014 |
| KR | 20150130475 A | 11/2015 |
| WO | 2001015286 A1 | 3/2001 |
| WO | 2006055125 A1 | 5/2006 |
| WO | 2010015030 A1 | 2/2010 |
| WO | 2010073691 A1 | 7/2010 |
| WO | 2012024139 A1 | 2/2012 |
| WO | 2013144866 A1 | 10/2013 |
| WO | 2014037874 A1 | 3/2014 |
| WO | 2015115441 A1 | 8/2015 |
| WO | 2016081752 A1 | 5/2016 |
| WO | 2016122399 A1 | 8/2016 |

OTHER PUBLICATIONS

Feb. 18, 2016—(WO) International Search Report/Written Opinion—App PCT/US15/61691.

Feb. 18, 2016—(WO) International Search Report/Written Opinion—App PCT/US15/61675.

Feb. 24, 2016—(WO) International Search Report/Written Opinion—App PCT/US15/61676.

Shekharappa et al., Correlation between body mass index and cardiovascular parameters in obese and non-obese in different age groups, 2011, Internatinal Journal of Biological & Medical Research, 2(2): 551-555.

Weight Loss Resources, BMI Calculator, 2004, Web, Retreived from: http://www.weightlossresources.co.uk/body_weight/healthy_weight/bmi_calculator.htm.

CNET, First look: Withings Pulse a sleek wireless pedometer and heart rate monitor, 2013, Web Video. Retrieved from: https://www.youtube.com/watch?v=j8L6ls0fYmM.

Ratas, Review of Withings Pulse, 2013, Web, Retrieved from: http://technogog.com/review/reviewofwithingspulse/.

Cambridge University Engineering Department, Materials Data Book, 2003, Web, Rerieved from: http://www.mdpeng.cam.ac.uk/web/library/enginfo/dueddatabooks/materials.pdf.

May 4, 2016—(WO) ISR & WO—App PCT/US15/61694.

Funada S et al: "Body mass index and cardiovascular disease mortality in Japan: The Ohsaki Study", Preventive Medicine, Academic Press, XX, vol. 47, No. 1, Jul. 1, 2009 (Jul. 1, 2009), pp. 66-70.

Apr. 29, 2016—(WO) ISR & WO—App No. PCT/US2015/061644.

Jun. 7, 2016—(WO) ISR & WO—App No. PCT/US2015/061670.

Shad, Lessons Learnt From Breaking Things: Wrist Activity Trackers, 2013 Web, Retrieved from: http://www.mindtribe.com/2013/10/lessonslearntfrombreakinthings1/.

UM Libraries, The Michigan Technic, 1944, vols. 63-64, p. 34.

Jul. 23, 2018—(WO) ISR & WO—App No. PCT/US18/027256.

Pete Pachal: "How the Samsung Galaxy S5 Measures Your Heart Rate [VIDEO]", Feb. 25, 2014 (Feb. 25, 2014), pp. 1-7, XP0055795715. Retrieved from the Internet: URL:https://mashable.com/2014/02/24/samsung-gs5-heart-rate/?europe-liue[retrieved on Apr. 15, 2021].

WEARABLE ARTICLE WITH REMOVABLE MODULE

CROSS-REFERENCE TO RELATED APPLICATIONS

This application is a continuation of co-pending U.S. patent application Ser. No. 16/907,884, filed Jun. 22, 2020, and issued as U.S. Pat. No. 11,297,883 on Apr. 12, 2002, which is a continuation of U.S. patent application Ser. No. 15/951,705, filed Apr. 12, 2018, and issued as U.S. Pat. No. 10,687,562 on Jun. 23, 2020, which claims priority to and is a non-provisional of U.S. Provisional Application No. 62/484,725, filed Apr. 12, 2017, all of which prior applications are incorporated herein by reference in their entireties.

TECHNICAL FIELD

The present invention relates to apparel. Aspects of the disclosure concern, more particularly, an article of apparel that incorporates an electronic device that is retained within the article of apparel yet operable, and may be partially viewable, from outside the article of apparel.

BACKGROUND

When engaged in a physical activity, such as running, an athlete wants to maintain a focus on the activity. Although many mobile devices may be updated to include "apps" or modules that provide athletic or fitness-related information, they are often ineffective for many athletes, including those involved in intense physical activities. Removing an electronic device, such as a mobile phone or music player from a pocket to operate the device can be distracting to the athlete. In addition, the athlete may drop the device while fumbling to remove or replace the device from a pocket. Further, many athletes, including but not limited to professional, semi-professional, and league players are bound by rules and regulations which can greatly restrict the materials worn by the athlete during a game or tournament. Unfortunately, historically acceptable apparel was not designed to allow reliable reception of athletic sensing devices. This disclosure addresses these and other shortcomings of the prior art.

BRIEF SUMMARY

General aspects of the present disclosure relate to methods and structures for connecting a housing assembly to an article of apparel or other wearable article, as well as such an article with the housing assembly connected thereto and potentially an electronic module connected to or otherwise received in the housing assembly.

Aspects of the disclosure relate to a method for use with a housing assembly that includes a receptacle defining a chamber and having an access opening providing access to the chamber, such that receptacle is configured to removably receive an electronic module within the chamber by insertion of the electronic module through the access opening. The housing assembly further includes a first contact member having a first contact pad positioned outside the chamber and a first arm extending from the first contact pad into the chamber to form a first electrical contact and a second contact member having a second contact pad positioned outside the chamber and a second arm extending from the second contact pad into the chamber to form a second electrical contact, such that the first and second electrical contacts form an interface exposed to the chamber and configured for connection with a connector of the electronic module when the electronic module is received in the receptacle. The method includes connecting a first conductive lead to the first contact pad and connecting a second conductive lead to the second contact pad to place the first and second leads in electronic communication with the first and second electrical contacts, and bonding the housing assembly to a wearable article. The housing assembly is bonded between a top layer and a bottom layer of material forming at least a portion of the wearable article, such that the top layer and the bottom layer are bonded to the receptacle by a bonding material. The wearable article has an electrically-powered component, and the first and second conductive leads are connected to the electrically-powered component.

According to one aspect, the method further includes assembling the housing assembly. This assembling may include mounting the first and second contact members on a carrier and inserting the carrier into a cavity in the receptacle to engage the carrier with the receptacle such that the carrier supports the first and second electrical contacts to form the interface. The first arm and the second arm extend outside the receptacle such that the first contact pad and the second contact pad are positioned adjacent an outer surface of the receptacle.

According to another aspect, the method further includes covering at least the first contact pad and the second contact pad with an insulative material.

According to a further aspect, the bonding material is a heat-sealable material, and bonding the housing assembly to the wearable article includes placing the heat-sealable material between the receptacle and the top and bottom layers and heat pressing the top layer and the bottom layers to the receptacle. In one configuration, the receptacle has a flange extending outward around a periphery of the receptacle, and the heat pressing is applied at least around the flange of the receptacle.

According to yet additional aspects, the top layer and the bottom layer are formed of different materials and/or the top layer forms an outer surface of the wearable article in use.

According to a still further aspect, the access opening is on a top side of the receptacle and the first and second arms extend out of a bottom side of the receptacle opposite the top side, where the bottom layer is positioned inside of the top layer when the wearable article is in use, and the top layer covers at least a portion of the top side of the receptacle, such that the access opening is accessible from outside the wearable article. In one configuration, a portion of the top layer extends into the access opening and is bonded to an interior surface of the receptacle defining the chamber. In another configuration, the first and second conductive leads are connected to the first and second contact pads at a location inside of an inner surface of the wearable article in use.

Additional aspects of the disclosure relate to a method for use with a housing assembly that includes a receptacle defining a chamber and having an access opening providing access to the chamber, such that receptacle is configured to removably receive an electronic module within the chamber by insertion of the electronic module through the access opening. The housing assembly further includes a first contact member having a first contact pad positioned outside the chamber and a first arm extending from the first contact pad into the chamber to form a first electrical contact and a second contact member having a second contact pad positioned outside the chamber and a second arm extending from the second contact pad into the chamber to form a second electrical contact, such that the first and second electrical contacts form an interface exposed to the chamber and configured for connection with a connector of the electronic module when the electronic module is received in the receptacle. The method includes bonding the housing assembly to a wearable article between a top layer and a bottom layer of material forming at least a portion of the wearable article, such that the top layer and the bottom layer are bonded to the receptacle by a bonding material. The bottom layer is positioned inside of the top layer when the wearable article is in use, and the first arm and the second arm extend through the bottom layer and are positioned adjacent an inside surface of the wearable article.

According to one aspect, the access opening is on a top side of the receptacle and the first and second arms extend out of a bottom side of the receptacle opposite the top side, and the top layer covers at least a portion of the top side of the receptacle, such that the access opening is accessible from outside the wearable article. In one configuration, a portion of the top layer extends into the access opening and is bonded to an interior surface of the receptacle defining the chamber.

According additional aspects, the bottom layer forms the inside surface of the wearable article in use and/or the first and second contact pads have greater widths than the first and second arms.

According to another aspect, the method further includes assembling the housing assembly. This assembling may include mounting the first and second contact members on a carrier and inserting the carrier into a cavity in the receptacle to engage the carrier with the receptacle such that the carrier supports the first and second electrical contacts to form the interface, where the first arm and the second arm extend outside the receptacle.

According to a further aspect, the method further includes covering at least the first contact pad and the second contact pad and a portion of the inside surface of the wearable article with an insulative material.

According to yet another aspect, the bonding material is a heat-sealable material, and bonding the housing assembly to the wearable article includes placing the heat-sealable material between the receptacle and the top and bottom layers and heat pressing the top layer and the bottom layers to the receptacle. In one configuration, the receptacle has a flange extending outward around a periphery of the receptacle, and the heat pressing is applied at least around the flange of the receptacle.

According to a still further aspect, the method further includes connecting a first conductive lead to the first contact pad and connecting a second conductive lead to the second contact pad to place the first and second leads in electronic communication with the first and second electrical contacts, and the wearable article has an electrically-powered component, such that the first and second conductive leads are connected to the electrically-powered component.

Further aspects of the disclosure relate to a method for use with a housing assembly that includes a receptacle defining a chamber and having an access opening providing access to the chamber on a top side of the receptacle, such that receptacle is configured to removably receive an electronic module within the chamber by insertion of the electronic module through the access opening. The housing assembly further includes a first contact member having a first electrical contact exposed to the chamber and a second contact member having a second electrical contact exposed to the chamber, such that the first and second electrical contacts form an interface exposed to the chamber and configured for connection with a connector of the electronic module when the electronic module is received in the receptacle. The method includes bonding the housing assembly to a wearable article between a top layer and a bottom layer of material forming at least a portion of the wearable article, such that the top layer and the bottom layer are bonded to the receptacle by a bonding material and the top layer covers at least a portion of the top side of the receptacle. The bottom layer is positioned inside of the top layer when the wearable article is in use, and the access opening is accessible from an outside surface of the wearable article.

According to one aspect, the bonding material is a heat-sealable material, and bonding the housing assembly to the wearable article includes placing the heat-sealable material between the receptacle and the top and bottom layers and heat pressing the top layer and the bottom layers to the receptacle. In one configuration, the receptacle includes a flange extending outward around a periphery of the receptacle, and the heat pressing is applied at least around the flange of the receptacle.

According to another aspect, the top layer forms the outside surface of the wearable article in use.

Other aspects of the disclosure relate to a system manufactured using the methods described herein. In one example, the system includes a wearable article configured to be worn on a user's body, the wearable article having top and bottom layers of material forming at least a portion thereof, a receptacle, and first and second contact members. The receptacle defines a chamber and has an access opening providing access to the chamber on a top side of the receptacle, such that receptacle is configured to removably receive an electronic module within the chamber by insertion of the electronic module through the access opening. The first contact member includes a first contact pad positioned outside the chamber and a first arm extending from the first contact pad into the chamber to form a first electrical contact. The second contact member includes a second contact pad positioned outside the chamber and a second arm extending from the second contact pad into the chamber to form a second electrical contact, such that the first and second electrical contacts form an interface exposed to the chamber and configured for connection with a connector of the electronic module when the electronic module is received in the receptacle. The receptacle is bonded to the wearable article between the top layer and the bottom layer, such that the top layer and the bottom layer are bonded to the receptacle by a bonding material, and the access opening is accessible from an outside surface of the wearable article. The top layer covers at least a portion of the top side of the receptacle and a portion of the top layer extends into the access opening and is bonded to an interior surface of the receptacle defining the chamber, and the top layer has an opening permitting access to the interface through the top layer. The bottom layer covers at least a portion of a bottom side of the receptacle, such that the first and second arms extend through the bottom layer to position the first and second contact pads inside of the bottom layer.

According to one aspect, the top layer forms an outside surface of the wearable article in use, and the bottom layer forms an inside surface of the wearable article in use. In one configuration, the system further includes an insulative material covering at least the first and second contact pads and a portion of the inside surface of the wearable article adjacent to the first and second contact pads.

According to another aspect, the bonding material is a heat-sealable material located between the receptacle and the top and bottom layers and heat pressed to the receptacle.

According to a further aspect, the receptacle has a flange extending outward around a periphery of the receptacle, and the top and bottom layers are bonded to the receptacle at least around the flange of the receptacle.

According to yet another aspect, the system includes a housing including the receptacle and a carrier having the first and second contact members mounted thereon, where the carrier is received in a cavity in the receptacle to engage the carrier with the receptacle such that the carrier supports the first and second electrical contacts to form the interface.

Other features and advantages of the disclosure will be apparent from the following description taken in conjunction with the attached drawings.

BRIEF DESCRIPTION OF THE DRAWINGS

To allow for a more full understanding of the present disclosure, it will now be described by way of example, with reference to the accompanying drawings in which.

DETAILED DESCRIPTION

Aspects of this disclosure involve obtaining, storing, and/or processing athletic data relating to the physical movements of an athlete. The athletic data may be actively or passively sensed and/or stored in one or more non-transitory storage mediums. Still further aspects relate to using athletic data to generate an output, such as for example, calculated athletic attributes, feedback signals to provide guidance, and/or other information. These and other aspects will be discussed in the context of the following illustrative examples of a personal training system.

This application incorporates by reference U.S. patent application Ser. No. 13/828,893, filed Mar. 14, 2013; U.S. patent application Ser. No. 14/946,682, filed Nov. 19, 2015; U.S. patent application Ser. No. 14/946,670, filed Nov. 19, 2015; U.S. patent application Ser. No. 14/946,674, filed Nov. 19, 2015; U.S. patent application Ser. No. 14/946,691, filed Nov. 19, 2015; U.S. Provisional Application No. 62/082,113, filed Nov. 19, 2014; U.S. Provisional Application No. 62/100,782, filed Jan. 7, 2015; U.S. Provisional Application No. 62/146,029, filed Apr. 10, 2015; U.S. Provisional Application No. 62/168,357, filed May 29, 2015; U.S. Provisional Application No. 62/168,502, filed May 29, 2015; U.S. Provisional Application No. 62/215,497, filed Sep. 8, 2015; U.S. Provisional Application No. 62/359,879, filed Jul. 8, 2016; and U.S. Provisional Application No. 62/356,960, filed Jun. 30, 2016.

In the following description of the various embodiments, reference is made to the accompanying drawings, which form a part hereof, and in which is shown by way of illustration various embodiments in which aspects of the disclosure may be practiced. It is to be understood that other embodiments may be utilized and structural and functional modifications may be made without departing from the scope and spirit of the present disclosure. Further, headings within this disclosure should not be considered as limiting aspects of the disclosure and the example embodiments are not limited to the example headings.

I. Example Personal Training System

A. Illustrative Networks

Figure 1:
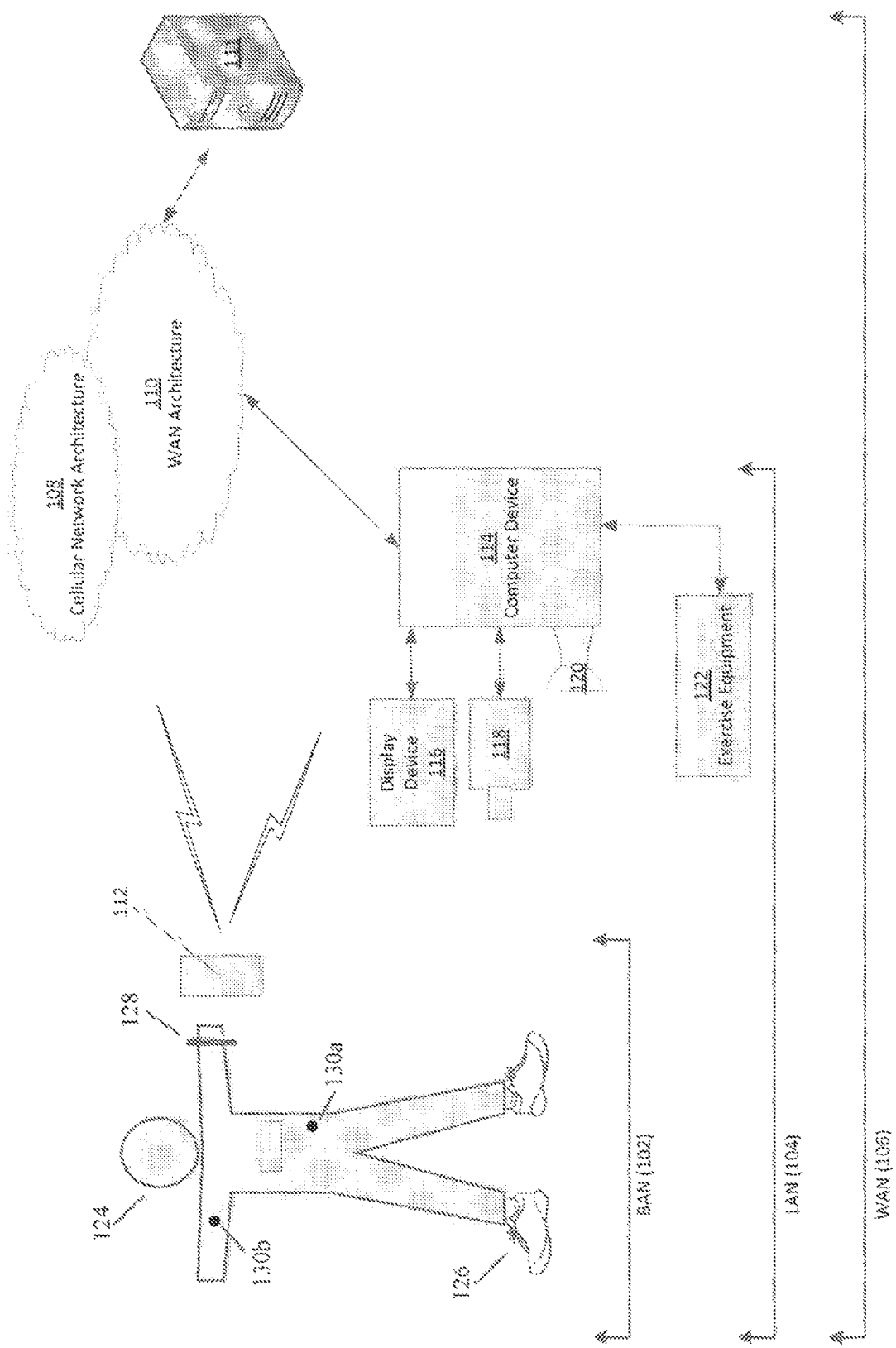
FIG. 1 illustrates an example system that may be configured to provide personal training and/or obtain data from the physical movements of a user in accordance with example embodiments.

Aspects of this disclosure relate to systems and methods that may be utilized across a plurality of networks. In this regard, certain embodiments may be configured to adapt to dynamic network environments. Further embodiments may be operable in differing discrete network environments. FIG. 1 illustrates an example of a personal training system 100 in accordance with example embodiments. Example system 100 may include one or more interconnected networks, such as the illustrative body area network (BAN) 102, local area network (LAN) 104, and wide area network (WAN) 106. As shown in FIG. 1 (and described throughout this disclosure), one or more networks (e.g., BAN 102, LAN 104, and/or WAN 106), may overlap or otherwise be inclusive of each other. Those skilled in the art will appreciate that the illustrative networks 102-106 are logical networks that may each comprise one or more different communication protocols and/or network architectures and yet may be configured to have gateways to each other or other networks. For example, each of BAN 102, LAN 104 and/or WAN 106 may be operatively connected to the same physical network architecture, such as cellular network architecture 108 and/or WAN architecture 110. For example, portable electronic device 112, which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 108 and/or 110. These protocols are well known in the art, and thus will not be discussed here in more detail.

Network architectures 108 and 110 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 1, (such as portable electronic device 112 or any other device described herein) may be considered inclusive to one or more of the different logical networks 102-106. With the foregoing in mind, example components of an illustrative BAN and LAN (which may be coupled to WAN 106) will be described.

1. Example Local Area Network

LAN 104 may include one or more electronic devices, such as for example, computer device 114. Computer device 114, or any other component of system 100, may comprise a mobile terminal, such as a telephone, music player, tablet, netbook or any portable device. In other embodiments, computer device 114 may comprise a media player or recorder, desktop computer, server(s), a gaming console, such as for example, a Microsoft® XBOX, Sony® Playstation, and/or a Nintendo® Wii gaming consoles. Those skilled in the art will appreciate that these are merely example devices for descriptive purposes and this disclosure is not limited to any console or computing device.

Figure 2:
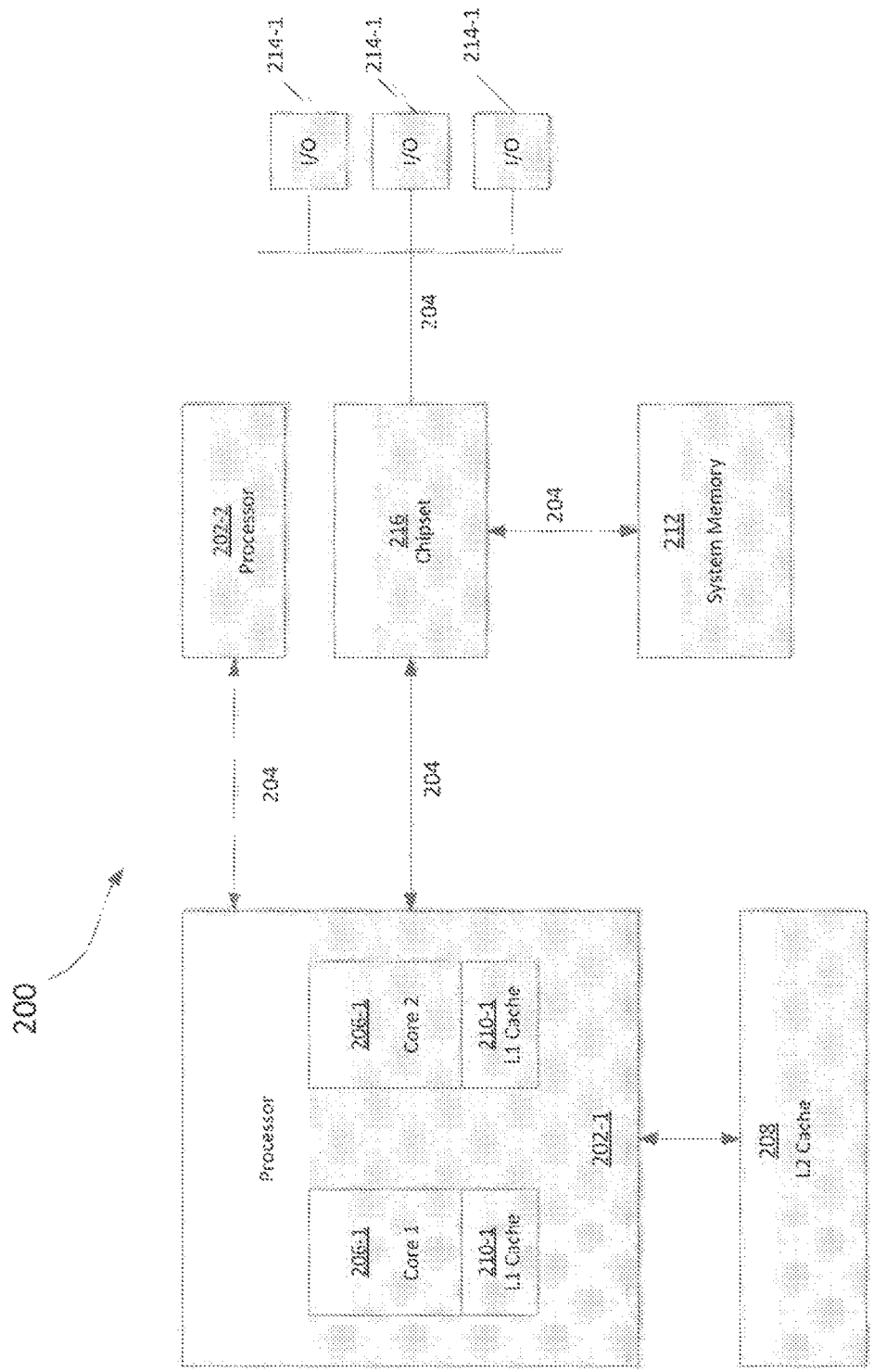
FIG. 2 illustrates an example computer device that may be part of or in communication with the system of FIG. 1.

Those skilled in the art will appreciate that the design and structure of computer device 114 may vary depending on several factors, such as its intended purpose. One example implementation of computer device 114 is provided in FIG. 2, which illustrates a block diagram of computing device 200. Those skilled in the art will appreciate that the disclosure of FIG. 2 may be applicable to any device disclosed herein. Device 200 may include one or more processors, such as processor 202-1 and 202-2 (generally referred to herein as "processors 202" or "processor 202"). Processors 202 may communicate with each other or other components via an interconnection network or bus 204. Processor 202 may include one or more processing cores, such as cores 206-1 and 206-2 (referred to herein as "cores 206" or more generally as "core 206"), which may be implemented on a single integrated circuit (IC) chip.

Cores 206 may comprise a shared cache 208 and/or a private cache (e.g., caches 210-1 and 210-2, respectively). One or more caches 208/210 may locally cache data stored in a system memory, such as memory 212, for faster access by components of the processor 202. Memory 212 may be in communication with the processors 202 via a chipset 216. Cache 208 may be part of system memory 212 in certain embodiments. Memory 212 may include, but is not limited to, random access memory (RAM), read only memory (ROM), and include one or more of solid-state memory, optical or magnetic storage, and/or any other medium that can be used to store electronic information. Yet other embodiments may omit system memory 212.

System 200 may include one or more I/O devices (e.g., I/O devices 214-1 through 214-3, each generally referred to as I/O device 214). I/O data from one or more I/O devices 214 may be stored at one or more caches 208, 210 and/or system memory 212. Each of I/O devices 214 may be permanently or temporarily configured to be in operative communication with a component of system 100 using any physical or wireless communication protocol.

Returning to FIG. 1, four example I/O devices (shown as elements 116-122) are shown as being in communication with computer device 114. Those skilled in the art will appreciate that one or more of devices 116-122 may be stand-alone devices or may be associated with another device besides computer device 114. For example, one or more I/O devices may be associated with or interact with a component of BAN 102 and/or WAN 106. I/O devices 116-122 may include, but are not limited to athletic data acquisition units, such as for example, sensors. One or more I/O devices may be configured to sense, detect, and/or measure an athletic parameter from a user, such as user 124. Examples include, but are not limited to: an accelerometer, a gyroscope, a location-determining device (e.g., GPS), light (including non-visible light) sensor, temperature sensor (including ambient temperature and/or body temperature), sleep pattern sensors, heart rate monitor, image-capturing sensor, moisture sensor, force sensor, compass, angular rate sensor, and/or combinations thereof among others.

In further embodiments, I/O devices 116-122 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 100 may be configured to transmit and/or receive athletic data, including the parameters, metrics, or physiological characteristics collected within system 100 or otherwise provided to system 100. As one example, WAN 106 may comprise server 111. Server 111 may have one or more components of system 200 of FIG. 2. In one embodiment, server 111 comprises at least a processor and a memory, such as processor 206 and memory 212. Server 111 may be configured to store computer-executable instructions on a non-transitory computer-readable medium. The instructions may comprise athletic data, such as raw or processed data collected within system 100. System 100 may be configured to transmit data, such as energy expenditure points, to a social networking website or host such a site. Server 111 may be utilized to permit one or more users to access and/or compare athletic data. As such, server 111 may be configured to transmit and/or receive notifications based upon athletic data or other information.

Returning to LAN 104, computer device 114 is shown in operative communication with a display device 116, an image-capturing device 118, sensor 120 and exercise device 122, which are discussed in turn below with reference to example embodiments. In one embodiment, display device 116 may provide audio-visual cues to athlete 124 to perform a specific athletic movement. The audio-visual cues may be provided in response to computer-executable instruction executed on computer device 114 or any other device, including a device of BAN 102 and/or WAN. Display device 116 may be a touchscreen device or otherwise configured to receive a user-input.

In one embodiment, data may be obtained from image-capturing device 118 and/or other sensors, such as sensor 120, which may be used to detect (and/or measure) athletic parameters, either alone or in combination with other devices, or stored information. Image-capturing device 118 and/or sensor 120 may comprise a transceiver device. In one embodiment sensor 128 may comprise an infrared (IR), electromagnetic (EM) or acoustic transceiver. For example, image-capturing device 118, and/or sensor 120 may transmit waveforms into the environment, including towards the direction of athlete 124 and receive a "reflection" or otherwise detect alterations of those released waveforms. Those skilled in the art will readily appreciate that signals corresponding to a multitude of different data spectrums may be utilized in accordance with various embodiments. In this regard, devices 118 and/or 120 may detect waveforms emitted from external sources (e.g., not system 100). For example, devices 118 and/or 120 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology.

In one embodiment, exercise device 122 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 122 may be or comprise an interface for receiving an electronic device containing athletic data performed remotely from computer device 114. For example, a user may use a sporting device (described below in relation to BAN 102) and upon returning home or the location of equipment 122, download athletic data into element 122 or any other device of system 100. Any I/O device disclosed herein may be configured to receive activity data.

2. Body Area Network

BAN 102 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 112, it may be a multi-purpose electronic device, that for example, includes a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as an output device, input device, and/or storage device for a computer. Device 112 may be configured as an input device for receiving raw or processed data collected from one or more devices in BAN 102, LAN 104, or WAN 106. In one or more embodiments, portable device 112 may comprise one or more components of computer device 114. For example, portable device 112 may be include a display 116, image-capturing device 118, and/or one or more data acquisition devices, such as any of the I/O devices 116-122 discussed above, with or without additional components, so as to comprise a mobile terminal.

a. Illustrative Apparel/Accessory Sensors

In certain embodiments, I/O devices may be formed within or otherwise associated with user's 124 clothing or accessories, including a watch, armband, wristband, necklace, shirt, shoe, or the like. These devices may be configured to monitor athletic movements of a user. It is to be understood that they may detect athletic movement during user's 124 interactions with computer device 114 and/or operate independently of computer device 114 (or any other device disclosed herein). For example, one or more devices in BAN 102 may be configured to function as an all-day activity monitor that measures activity regardless of the user's proximity or interactions with computer device 114. It is to be further understood that the sensory system 302 shown in FIG. 3 and the device assembly 400 shown in FIG. 4, each of which are described in the following paragraphs, are merely illustrative examples.

i. Shoe-Mounted Device

Figure 3:
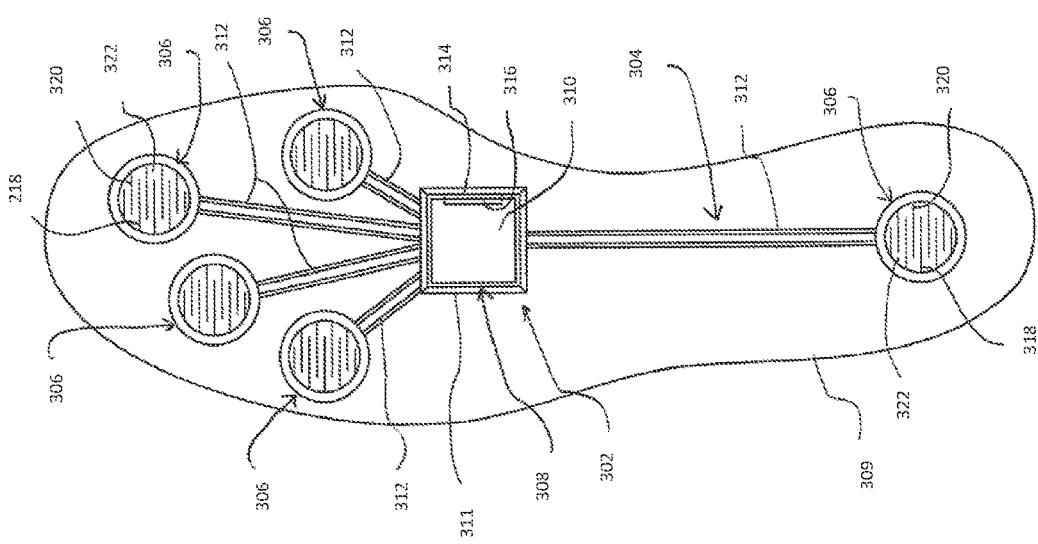
FIG. 3 shows an illustrative sensor assembly that may be worn by a user in accordance with example embodiments.

In certain embodiments, device 126 shown in FIG. 1, may comprise footwear which may include one or more sensors, including but not limited to those disclosed herein and/or known in the art. FIG. 3 illustrates one example embodiment of a sensor system 302 providing one or more sensor assemblies 304. Assembly 304 may comprise one or more sensors, such as for example, an accelerometer, gyroscope, location-determining components, force sensors and/or or any other sensor disclosed herein or known in the art. In the illustrated embodiment, assembly 304 incorporates a plurality of sensors, which may include force-sensitive resistor (FSR) sensors 306; however, other sensor(s) may be utilized. Port 308 may be positioned within a sole structure 309 of a shoe, and is generally configured for communication with one or more electronic devices. Port 308 may optionally be provided to be in communication with an electronic module 310, and the sole structure 309 may optionally include a housing 311 or other structure to receive the module 310. The sensor system 302 may also include a plurality of leads 312 connecting the FSR sensors 306 to the port 308, to enable communication with the module 310 and/or another electronic device through the port 308. Module 310 may be contained within a well or cavity in a sole structure of a shoe, and the housing 311 may be positioned within the well or cavity. In one embodiment, at least one gyroscope and at least one accelerometer are provided within a single housing, such as module 310 and/or housing 311. In at least a further embodiment, one or more sensors are provided that, when operational, are configured to provide directional information and angular rate data. The port 308 and the module 310 include complementary interfaces 314, 316 for connection and communication.

In certain embodiments, at least one force-sensitive resistor 306 shown in FIG. 3 may contain first and second electrodes or electrical contacts 318, 320 and a force-sensitive resistive material 322 disposed between the electrodes 318, 320 to electrically connect the electrodes 318, 320 together. When pressure is applied to the force-sensitive material 322, the resistivity and/or conductivity of the force-sensitive material 322 changes, which changes the electrical potential between the electrodes 318, 320. The change in resistance can be detected by the sensor system 302 to detect the force applied on the sensor 316. The force-sensitive resistive material 322 may change its resistance under pressure in a variety of ways. For example, the force-sensitive material 322 may have an internal resistance that decreases when the material is compressed. Further embodiments may utilize "volume-based resistance", which may be implemented through "smart materials." As another example, the material 322 may change the resistance by changing the degree of surface-to-surface contact, such as between two pieces of the force sensitive material 322 or between the force sensitive material 322 and one or both electrodes 318, 320. In some circumstances, this type of force-sensitive resistive behavior may be described as "contact-based resistance."

ii. Wrist-Worn Device

Figure 4:
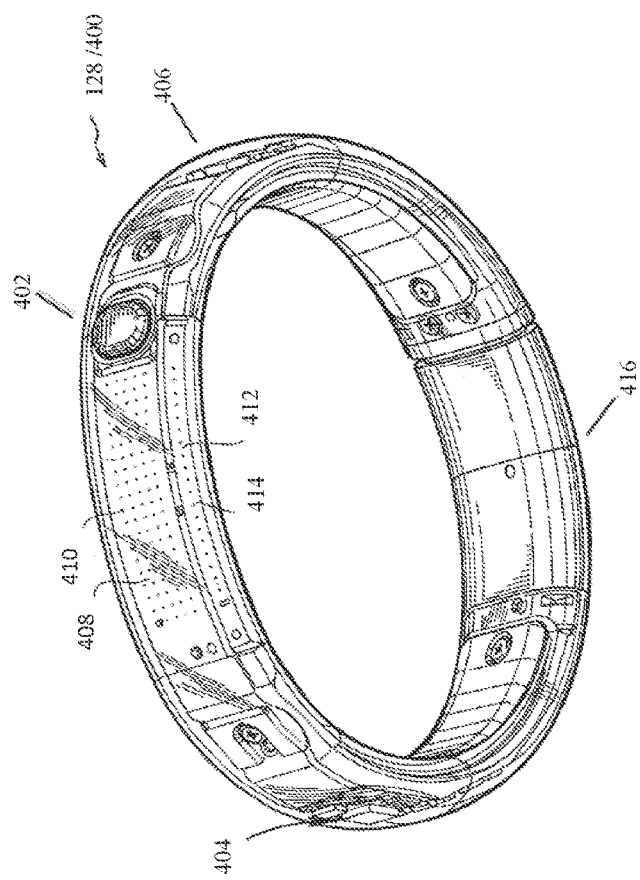
FIG. 4 shows another example sensor assembly that may be worn by a user in accordance with example embodiments.

As shown in FIG. 4, device 400 (which may resemble or comprise sensory device 128 shown in FIG. 1), may be configured to be worn by user 124, such as around a wrist, arm, ankle, neck or the like. Device 400 may include an input mechanism, such as a depressible input button 402 configured to be used during operation of the device 400. The input button 402 may be operably connected to a controller 404 and/or any other electronic components, such as one or more of the elements discussed in relation to computer device 114 shown in FIG. 1. Controller 404 may be embedded or otherwise part of housing 406. Housing 406 may be formed of one or more materials, including elastomeric components and comprise one or more displays, such as display 408. The display may be considered an illuminable portion of the device 400. The display 408 may include a series of individual lighting elements or light members such as LED lights 410. The lights may be formed in an array and operably connected to the controller 404. Device 400 may include an indicator system 412, which may also be considered a portion or component of the overall display 408. Indicator system 412 can operate and illuminate in conjunction with the display 408 (which may have pixel member 414) or completely separate from the display 408. The indicator system 412 may also include a plurality of additional lighting elements or light members, which may also take the form of LED lights in an exemplary embodiment. In certain embodiments, indicator system may provide a visual indication of goals, such as by illuminating a portion of lighting members of indicator system 412 to represent accomplishment towards one or more goals. Device 400 may be configured to display data expressed in terms of activity points or currency earned by the user based on the activity of the user, either through display 408 and/or indicator system 412.

A fastening mechanism 416 can be disengaged wherein the device 400 can be positioned around a wrist or portion of the user 124 and the fastening mechanism 416 can be subsequently placed in an engaged position. In one embodiment, fastening mechanism 416 may comprise an interface, including but not limited to a USB port, for operative interaction with computer device 114 and/or devices, such as devices 120 and/or 112. In certain embodiments, fastening member may comprise one or more magnets. In one embodiment, fastening member may be devoid of moving parts and rely entirely on magnetic forces.

In certain embodiments, device 400 may comprise a sensor assembly (not shown in FIG. 4). The sensor assembly may comprise a plurality of different sensors, including those disclosed herein and/or known in the art. In an example embodiment, the sensor assembly may comprise or permit operative connection to any sensor disclosed herein or known in the art. Device 400 and or its sensor assembly may be configured to receive data obtained from one or more external sensors.

iii. Apparel and/or Body Location Sensing

Element 130 of FIG. 1 shows an example sensory location which may be associated with a physical apparatus, such as a sensor, data acquisition unit, or other device. Yet in other embodiments, it may be a specific location of a body portion or region that is monitored, such as via an image capturing device (e.g., image capturing device 118). In certain embodiments, element 130 may comprise a sensor, such that elements 130a and 130b may be sensors integrated into apparel, such as athletic clothing. Such sensors may be placed at any desired location of the body of user 124. Sensors 130a/b may communicate (e.g., wirelessly) with one or more devices (including other sensors) of BAN 102, LAN 104, and/or WAN 106. In certain embodiments, passive sensing surfaces may reflect waveforms, such as infrared light, emitted by image-capturing device 118 and/or sensor 120. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Figure 5:
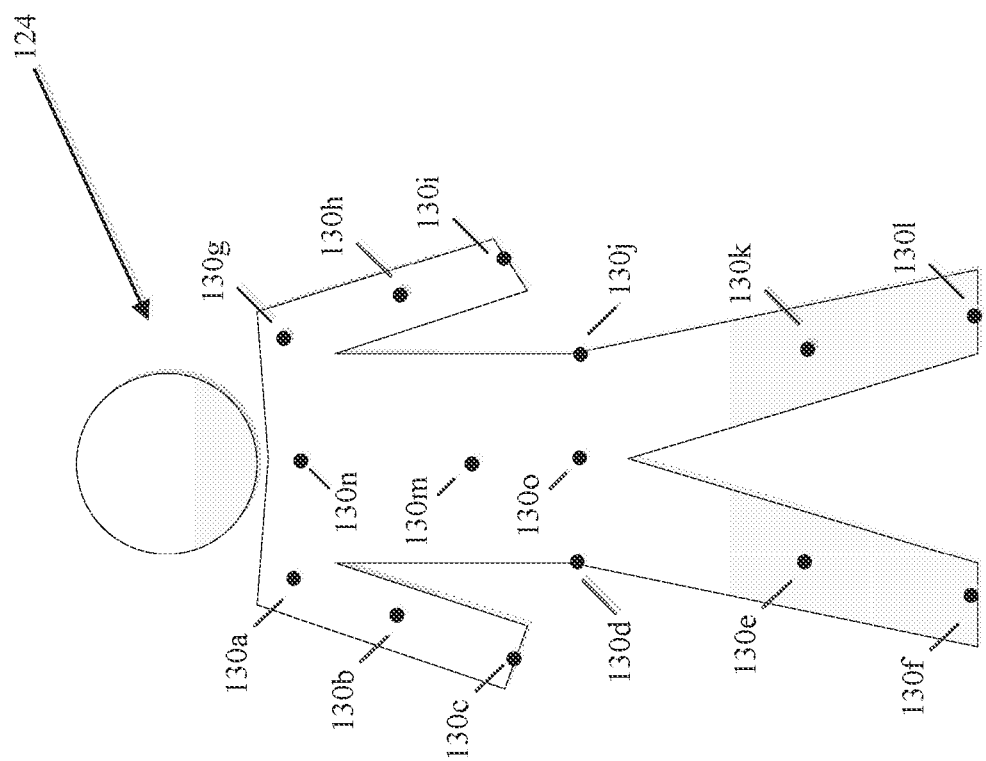
FIG. 5 shows illustrative locations for sensory input which may include physical sensors located on/in a user's clothing and/or be based upon identification of relationships between two moving body parts of the user.

FIG. 5 shows illustrative locations for sensory input (see, e.g., sensory locations 130a-130o). In this regard, sensors may be physical sensors located on/in a user's clothing, yet in other embodiments, sensor locations 130a-130o may be based upon identification of relationships between two moving body parts. For example, sensor location 130a may be determined by identifying motions of user 124 with an image-capturing device, such as image-capturing device 118. Thus, in certain embodiments, a sensor may not physically be located at a specific location (such as one or more of sensor locations 130a-130o), but is configured to sense properties of that location, such as with image-capturing device 118 or other sensor data gathered from other locations. In this regard, the overall shape or portion of a user's body may permit identification of certain body parts. Regardless of whether an image-capturing device is utilized and/or a physical sensor located on the user 124, and/or using data from other devices, (such as sensory system 302), device assembly 400 and/or any other device or sensor disclosed herein or known in the art is utilized, the sensors may sense a current location of a body part and/or track movement of the body part. In one embodiment, sensory data relating to location 130m may be utilized in a determination of the user's center of gravity (a.k.a, center of mass). For example, relationships between location 130a and location(s) 130f/130l with respect to one or more of location(s) 130m-130o may be utilized to determine if a user's center of gravity has been elevated along the vertical axis (such as during a jump) or if a user is attempting to "fake" a jump by bending and flexing their knees. In one embodiment, sensor location 1306n may be located at about the sternum of user 124. Likewise, sensor location 130o may be located approximate to the naval of user 124. In certain embodiments, data from sensor locations 130m-130o may be utilized (alone or in combination with other data) to determine the center of gravity for user 124. In further embodiments, relationships between multiple sensor locations, such as sensors 130m-130o, may be utilized in determining orientation of the user 124 and/or rotational forces, such as twisting of user's 124 torso. Further, one or more locations, such as location(s), may be utilized as (or approximate) a center of moment location. For example, in one embodiment, one or more of location(s) 130m-130o may serve as a point for a center of moment location of user 124. In another embodiment, one or more locations may serve as a center of moment of specific body parts or regions.

II. Athletic Band with Removable Module

Aspects of this disclosure relate to a system that may measure one or more attributes (e.g., physiological, biomedical, athletic, with the understanding that these may be overlapping examples) of a user during physical movements. In one embodiment, systems and methods may measure one or more attributes of a user while performing intense physical exercise or movements. For example, users may be participating in professional sporting activities, including but not limited to: American football, football, basketball, swimming, or a combination thereof. In one embodiment, systems and methods may consistently provide measurements from a user during exercises in which the system experiences impact forces and/or acceleration magnitudes commonly encountered during intensive activity, such as engaging in professional sports.

Certain aspects relate to a modular system that may firmly retain or otherwise hold at least one sensor against a user's skin during intense physical activities. In one embodiment, the system may be configured to retain a heart rate sensor against a user's skin during the intense physical activity in a manner that allows accurate readings during the activity. The band may further secure at least one sensor against the skin and allow for less than 1 mm of movement of the sensor with respect to the user's skin during the athletic activity or during movements commonly associated with the average forces and/or acceleration magnitudes of the specific athletic activity. In yet another embodiment, the band may be configured such that a removable sensor moves less than 0.5 mm with respect to the surface of the user's skin during the athletic activity. The system may comprise a band 920 configured to be secured against the user's skin or clothing. In one embodiment, the band is configured to be an armband, however, may be configured as a wristband, waistband, or other configuration. In one embodiment, the band 920 is configured to be worn between the user's elbow and wrist. In another embodiment, the band is configured to be worn in a location between the elbow and the shoulder.

Band 920 may be any suitable article of apparel that can be attached to the body such as, but not limited to, bands such as armbands, wristbands, leg bands, and belts. In addition, the article of apparel may be any suitable article of apparel that can be worn on the body such as shirts, jackets, coats, sweatshirts, vests, shorts, and pants, and various other articles of clothing.

In one embodiment, the band 920 may be configured without fasteners configured to retain the band around the arm. In one embodiment, the band may exhibit a modulus of elasticity that allows the band to be retained around an appendage of the user (e.g., arm) in a manner that fasteners are not required to secure the band 920 to the appendage to obtain accurate sensor readings during the activity, which may be intense athletic activity. In yet another embodiment, fasteners may be utilized to connect at least a portion or portions of the band together for attachment to the appendage. Any suitable fasteners may be used such as Velcro, snaps, buttons, buckles, and zippers as is within the skill of the art.

In another aspect of the invention, as shown in the figures herein, a wrist band or armband may be a continuous tubular band made of an elastic material that can be pulled onto the wrist or arm. As discussed below, a pocket (e.g., pocket 940) may be attached to, or formed integrally with, the band 920. As further discussed below, band 920 may be configured to comprise a "pocket" configured to retain an electronic module. In this regard, the band may form a seal or other surface around a portion of the user's skin in a manner that distributes forces such that at least a portion of the band 920 is held against the user's skin with a less force per unit area compared to any surface of an electronic module 930 held in the pocket 940 is pressed against the skin when the user is wearing the band 920. Band 920 may further be configured such that a certain portion of ambient light is blocked from contacting the user's skin under the band 920. In this regard, band 920 may block light in one or more specific regions and/or over the entire area covered by the band during normal use. In one embodiment, at least 75% of ambient light is blocked from reaching the area of the band immediate proximate to where a sensor extends from an aperture of the band and contacts the surface of the user's skin.

Generally, the device includes a band 920 configured to be worn by or otherwise attached to the body of a user and a module 930 configured to be connected to the band 920, in order to be worn by or otherwise attached to the user. The band 920 may be an armband in one embodiment, as illustrated in FIGS. 15-19, which is configured to be worn on the upper forearm of the user, just below the elbow. The band 920 in this embodiment includes a tubular body 921 defining a central passage 922, such that the user's arm is received through the passage 922 and the tubular body 921 wraps around the arm. The tubular body 921 is somewhat frusto-conical in shape in the embodiment shown, with a wider top end 923 configured to be positioned closer to the elbow, and an opposite narrower bottom end 924 configured to be positioned closer to the wrist, where the arm is typically smaller. The frusto-conical shape of the tubular body 921 may assist in resisting slipping of the band 920 when worn on the user's forearm during activity. In another embodiment, a similarly structured band 920 may be configured to be worn elsewhere on the body. For example, the band 920 may be configured to be worn elsewhere on the arm, such as on the upper arm, the wrist, the hand, etc. As another example, the band 920 may be configured to be wrap around a different body part of the user, such as various locations on the leg, neck, torso, head, etc. It is understood that the dimensions and contours of the band 920 may be adjusted for wrapping around different body parts.

In one embodiment, the band 920 may be formed of a flexible, elastic material that can stretch to allow the user to comfortably wear the band 920 and to place the band 920 on and off of the user's body, e.g., an elastic fabric. The band 920 may be made from two or more layers of material that are joined together, and which may be part of a single piece folded over to create multiple layers. FIGS. 15-19 illustrate one embodiment of the band 920 that utilizes a housing 963, as described herein.

Figure 6:
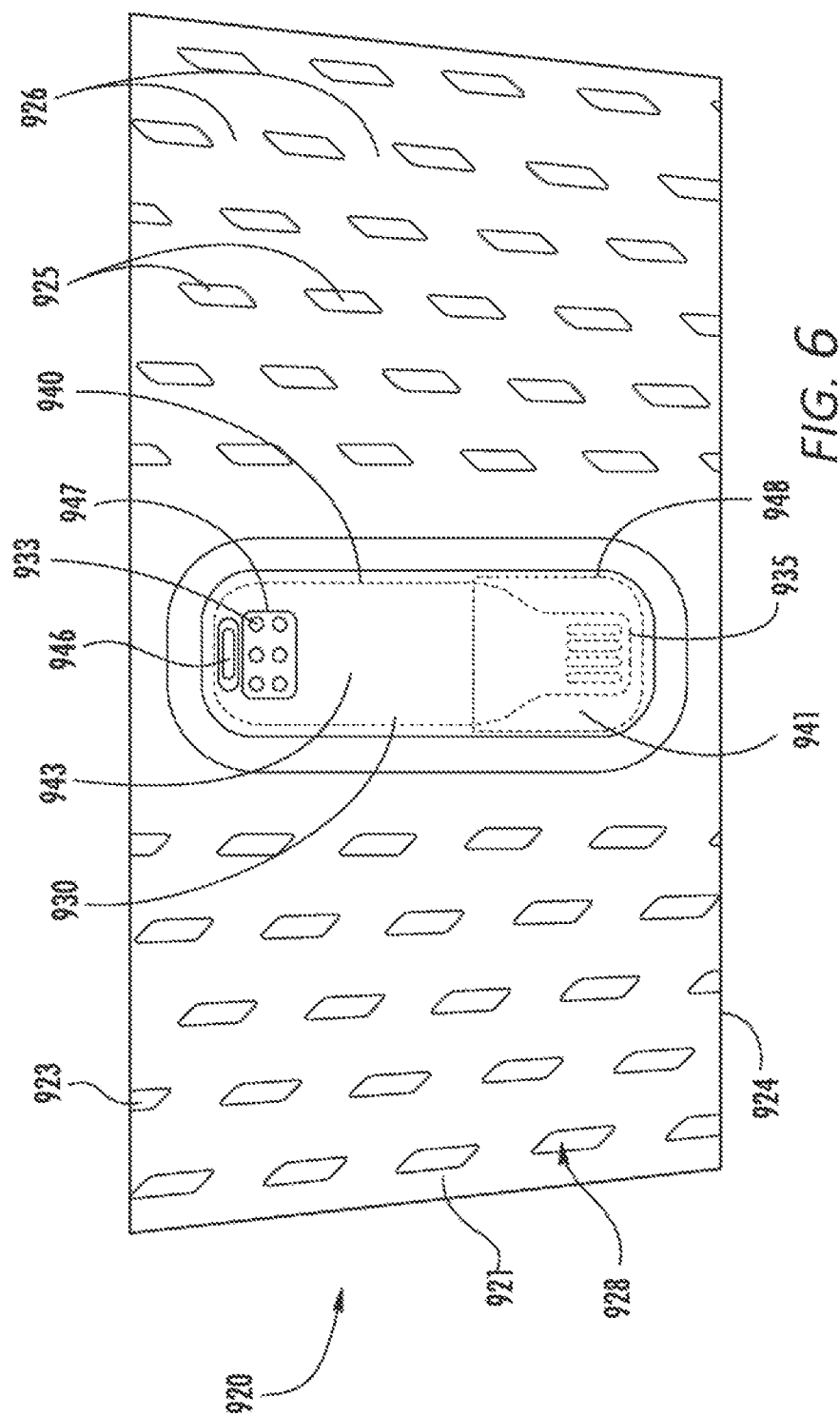
FIG. 6 is a top view and a side view of one embodiment of a band according to aspects of the disclosure.
Figure 7:
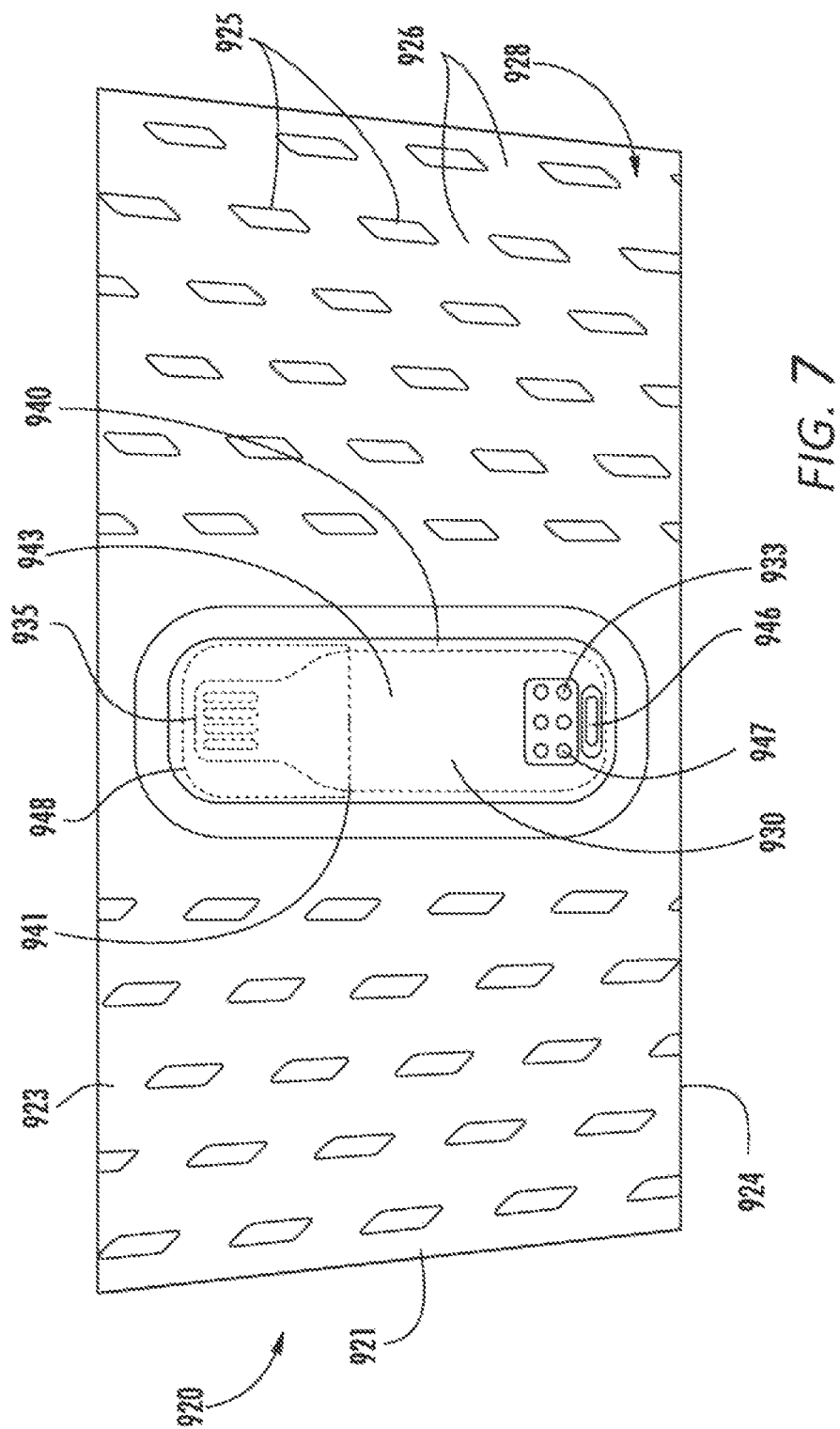
FIG. 7 is a top view and a side view of another embodiment of a band according to aspects of the disclosure.

In the embodiments shown in FIGS. 6-7 and 15-19, the band 920 is made from a piece of fabric that is folded over onto itself to form two layers and joined by adhesive applied between the two layers. The adhesive may be formed into a pattern in some embodiments, which may be visible in the finished product, creating a distinct visual appearance. The adhesive pattern may also be functional, such as in controlling the maximum degree of stretching of the band 920, controlling the locations of stretching or other deformation of the band 920, enhancing the durability of the band 920, and/or other functions. As shown in FIGS. 6-7, the adhesive is applied in a plurality of lines 925 extending in the axial direction (i.e., between the ends 923, 924) along the band 920 and spaced circumferentially from each other. In these configurations, radial stretching of the band 920 occurs between the lines 925, and the adhesive lines 925 provide low-stretch areas. The band 920 in FIGS. 6-7 may have broken or discontinuous adhesive lines 925 (i.e., line segments), having one or more gaps 926 along each line 925. Additionally, the gaps 926 of each line 925 in this embodiment may be offset or staggered from the gaps 926 of the adjacent lines 925. In another embodiment, the band 920 may have solid adhesive lines (which may be straight and/or curved), or one or more solid blocks of adhesive. The configurations of the adhesive lines as described herein provide several advantages. First, the lines 925 extending axially allows most of the radial stretching of the band to occur between the lines 925, so that the modulus or elastic response of the elastic material of the band 920 controls the amount of stretching. Additionally, the lines 925 extending axially permits the adhesive of the lines 925 to have a more significant influence on the modulus or elastic response of the band 920 in the axial direction, thus limiting the amount of axial stretching that occurs. This is beneficial to avoid excess stretching as the band 920 is pulled onto the user's body (e.g., forearm), so that the band 920 slides as desired, rather than wasting user-exerted energy by stretching the band. The "offset" of the gaps 926 also helps limit axial stretching. Further, the intermittent application of the adhesive lines 925 provides greater breathability, as the fabric of the band material is typically more breathable than the adhesive. In another embodiment, the band 920 is made from a piece of fabric that is folded over onto itself to form two layers and joined around the ends 923, 924, such as by adhesive, stitching, etc.

The band 920 is generally configured to hold an electronic module 930, which may be removable from the band 920. In one embodiment, the band 920 has a pocket 940 defining a cavity 941 configured to receive the module 930 in a removable configuration.

In one embodiment, as illustrated in FIGS. 6-7 and 15-19, the pocket 940 is accessible from an inner surface 927 of the band 920 that is configured to confront and/or contact the user's body. In this configuration, the pocket 940 has an access opening 942 defined on the inner side 927 of the band 920, and the module 930 can be inserted and removed through the opening 942. In other embodiments, the access opening 942 may be located on the outer side 928 of the band 920. The band 920 may be flipped inside-out in order to facilitate this access. The pocket 940 in each embodiment shown in FIGS. 6-7 and 15-19 has an outer wall 943 that forms part of the outer surface 928 of the band 920 and an inner wall 944 that forms part of the inner surface 927 of the band 920, with the cavity 941 defined between the walls 943, 944. These walls 943, 944 are at least somewhat flexible in one embodiment, and may be made of a single layer and/or piece or multiple layers and/or pieces. In other embodiments, the walls 943, 944 may be rigid, and may be made of the same material or a different material as other portions of the band 920. The access opening 942 is defined within the inner wall 944 at one end of the cavity 941 in the embodiments of FIGS. 6-7 and 15-19, such that the module 930 is inserted by inserting one end of the module 930 (the USB connector 135 in one embodiment) into the opening 942 and then pushing the rest of the module 930 through the opening 942 and into the cavity 941.

FIGS. 6A-B illustrate embodiments of the band 920 with the module 930 inserted into the pocket 940. In FIG. 6A, the pocket 940 is configured for insertion of the module 930 with the light 934 and the button 933 positioned nearer the top end 923 of the band 920 (i.e., nearer the user's elbow) and the connector 935 positioned nearer the bottom end 924 of the band 920 (i.e., nearer the user's wrist). In FIG. 7, the pocket 940 is configured for insertion of the module 930 with the light 934 and the button 933 positioned nearer the bottom end 924 of the band 920 (i.e., nearer the user's wrist) and the connector 935 positioned nearer the top end 923 of the band 920 (i.e., nearer the user's elbow). It is understood that the access opening 942 (not shown in FIGS. 6-7) may be located near the top end 923 in FIG. 6 and near the bottom end 924 in FIG. 7. The configuration in FIG. 6B may provide greater ergonomics and ease of use. For example, viewing the light 934 and pushing the button 933 may require less movement and more natural movement when these components are located nearer the wrist. Also, the force of pushing the button 933 compresses the user's arm, and if the button 933 is nearer the wrist where the bone is closer to the skin, there is less soft tissue that can compress under the force of the button pushing. In the configuration of FIG. 6B, the protective shell 948 (described below) protects the connector 935, as it is located in an area where users may grip to pull the band 920 on the arm.

The pocket 940 may also include one or more sensor openings 945 configured to permit the sensor(s) 932 of the module 930 an unimpeded path to sense the user's body directly, such as by contacting the user's body (e.g., a heart rate sensor) or otherwise interacting directly with the user's body (e.g., an optical, heat, or other radiation-based sensor). In the embodiment illustrated in FIGS. 15-19, the pocket 940 has an opening 942 on the inner wall 944 that extends into the cavity 941 and is configured to act as both a sensor opening and access opening. In other words, the opening 942 is large enough to permit insertion of the module 930 into the cavity 941 through the opening 942, and a portion of the opening 942 permits the projection 939 of the module 930 to extend through to permit the sensor(s) 932 to be in close proximity to the user's body. In other embodiments, the pocket 940 may have a sensor opening 945 on the inner wall 944 that is separate from the access opening 942. the pocket 940 may have multiple sensor openings 945.

The outer wall 943 of the pocket is configured to cover the module 930, and may be configured to permit reading and/or manipulation of the module through the outer wall 943. For example, the outer wall 943 may include one or more windows 946 to permit viewing of a display of the module 930. Such a window 946 may be an opening in the outer wall 943 or a transparent or translucent portion that allows viewing of a light or lighted display therethrough. In the embodiments shown in FIGS. 6-7 and 15-19, the outer wall 943 has a window 946 to permit viewing of a single light, and may additionally or alternately have one or more windows 946 configured to permit viewing of a plurality of LEDs on the module 930 (i.e., a readable display). It is understood that the pocket 940 may have one or more windows 946 configured to be complementary with the structure of the module 930.

As another example, the outer wall 943 may have one or more button portions 947 that are configured to allow manipulation of one or more buttons 933 of the module 930 through the outer wall 943. It is understood that "buttons" may include mechanical/electrical buttons, a touch-screen interface, or other manually operable components. The button portion 947 may simply be a flexible portion of the outer wall 943 that permits the user to press the button portion 947 to activate the button 933 of the module 930. The outer wall 943 may further have one or more flex zones (not shown) to control flexing of the outer wall 943 and/or portions of the band 920, such as a concave or indented portion having greater flexibility. In another embodiment, the button portion 947 may have a button mechanism (or mechanisms) that actuates the button(s) 933 of the module 930. For example, in the embodiment of FIGS. 15-19, the outer wall 943 of the pocket has a button portion 947 configured to interact with the button 933 on the module 930 and a window 946 configured to permit viewing of the light 934 through the outer wall 943. In a further embodiment, the button portion 947 may double as a window 946, such as if the module 930 has a button with a light on it or if the module 930 has a lighted touch-screen display. The outer wall 943 may further have indicia, such as indications of the location(s) of the button(s) 933 on the module 930, logos, instructions, etc.

Figure 12:
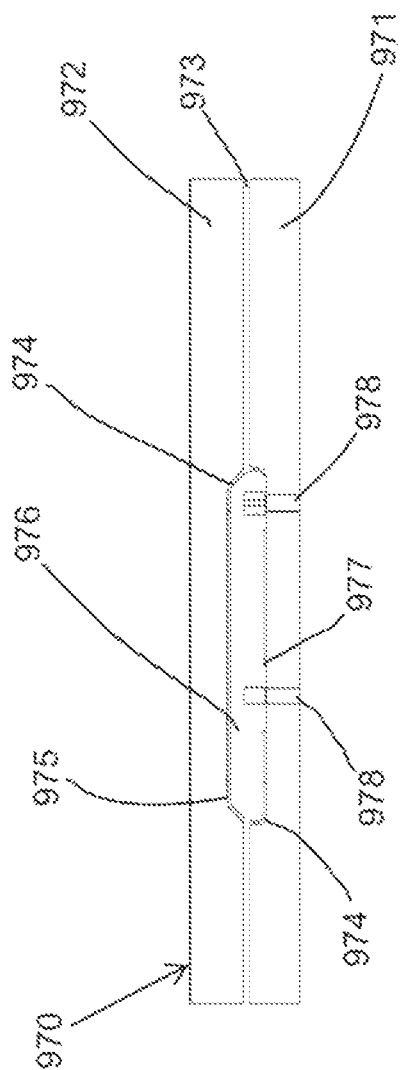
FIG. 12 is a cross-sectional view of the mold of FIG. 11 along a longitudinal axis.
Figure 13:
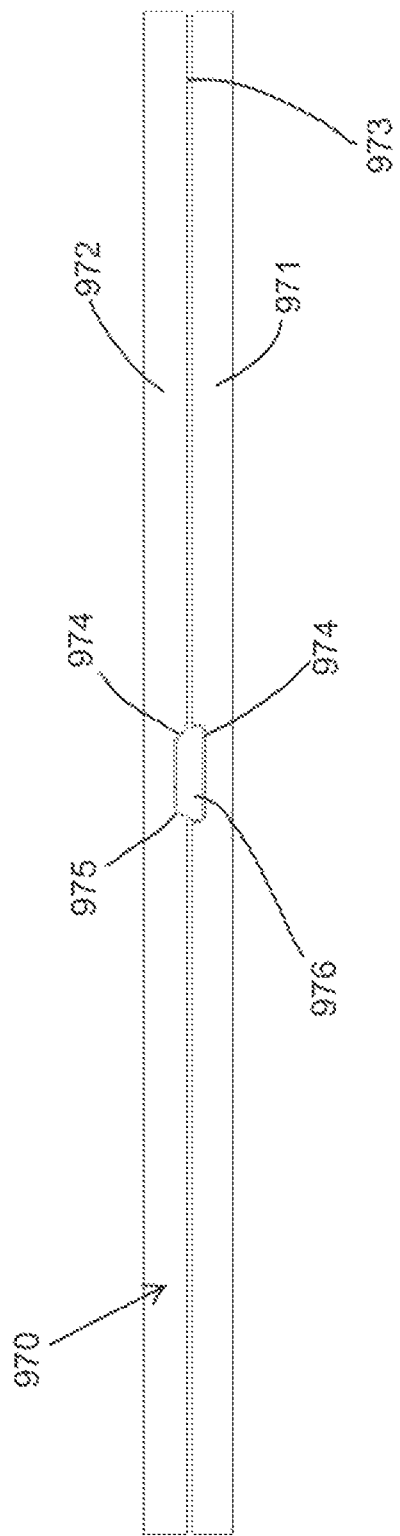
FIG. 13 is a cross-sectional view of the mold of FIG. 11 along a lateral axis.
Figure 14:
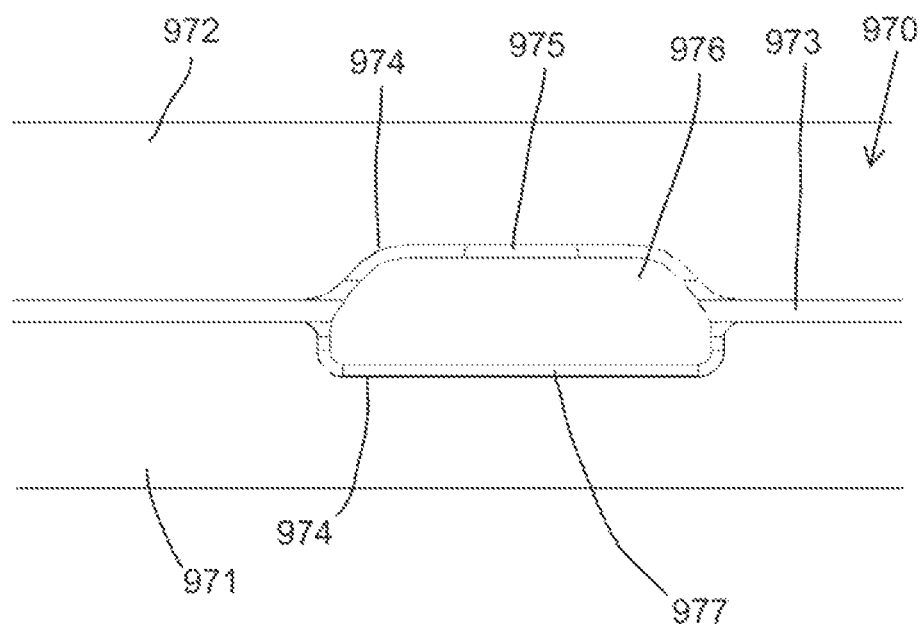
FIG. 14 is a magnified view of a portion of the mold as shown in FIG. 13.
Figure 15:
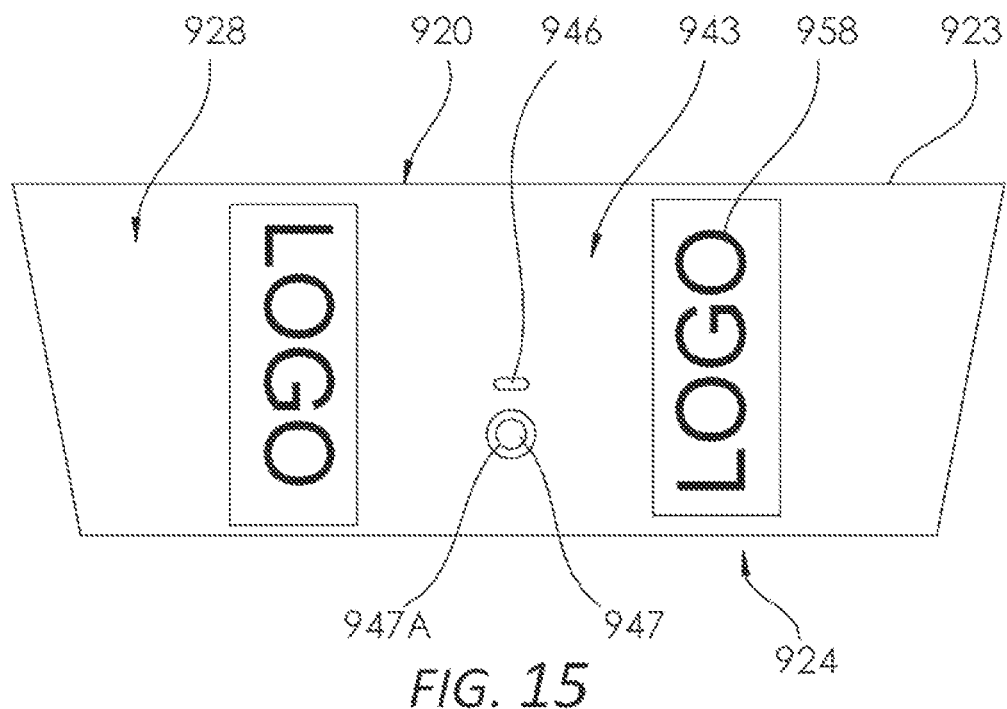
FIG. 15 is a top view of another embodiment of a band according to aspects of the disclosure.
Figure 16:
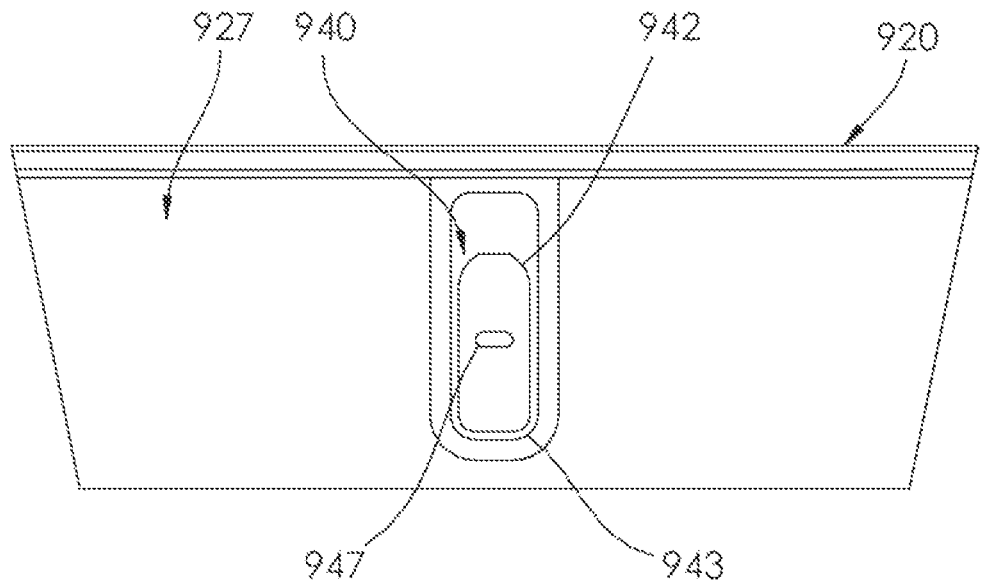
FIG. 16 is a top view of the band of FIG. 15, turned inside-out.
Figure 17:
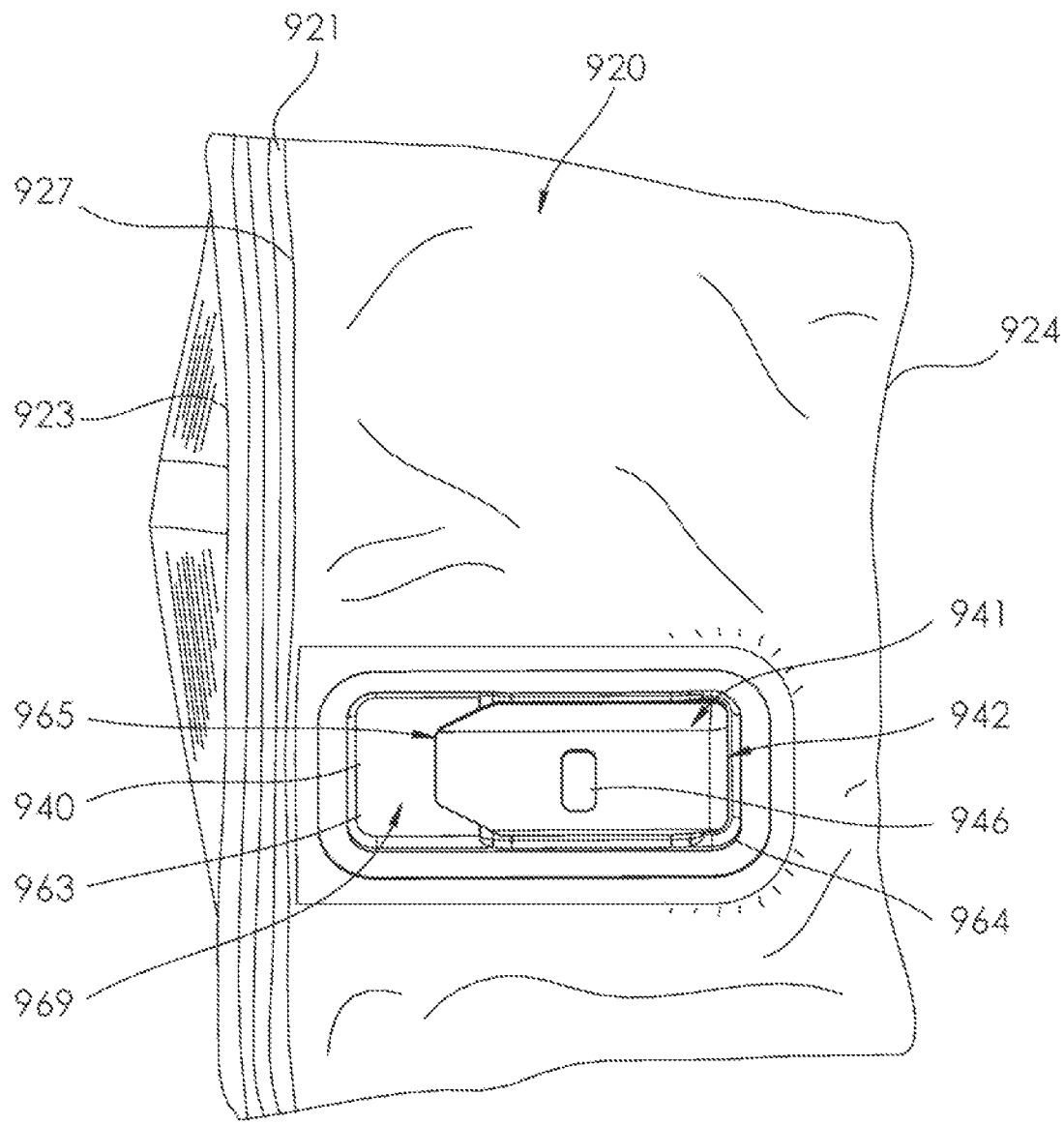
FIG. 17 is top view of the band of FIG. 15, turned inside out.
Figure 18:
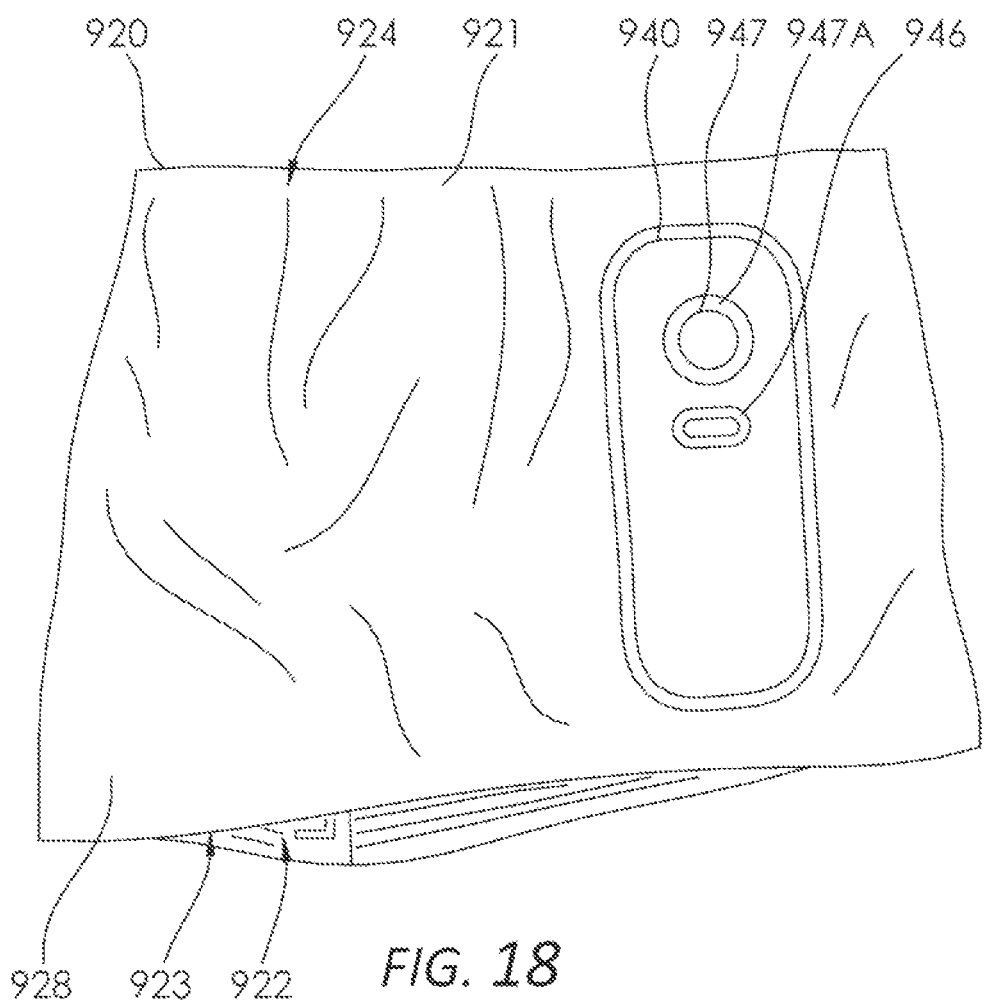
FIG. 18 is top view of the band of FIG. 15.
Figure 19:
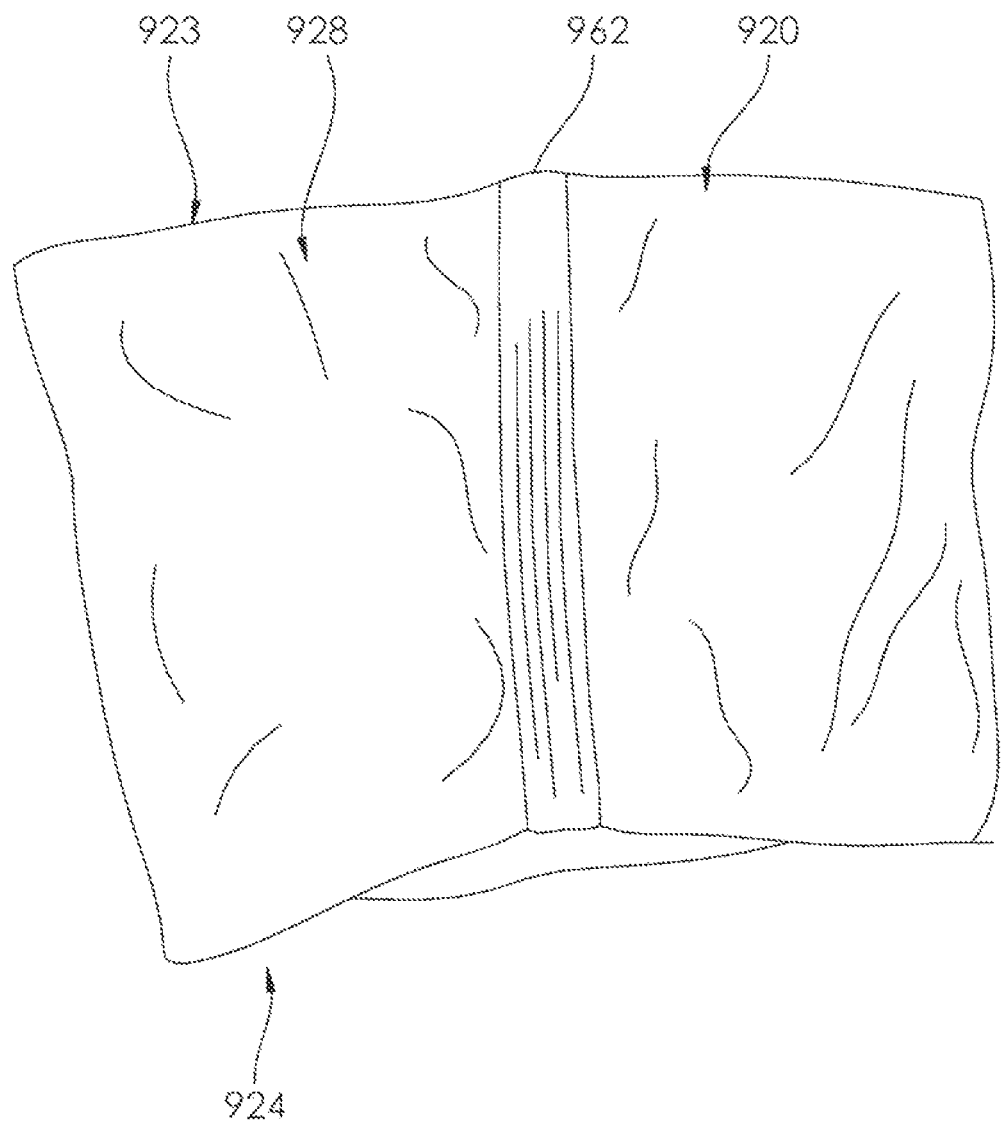
FIG. 19 is bottom view of the band of FIG. 15.
Figure 20:
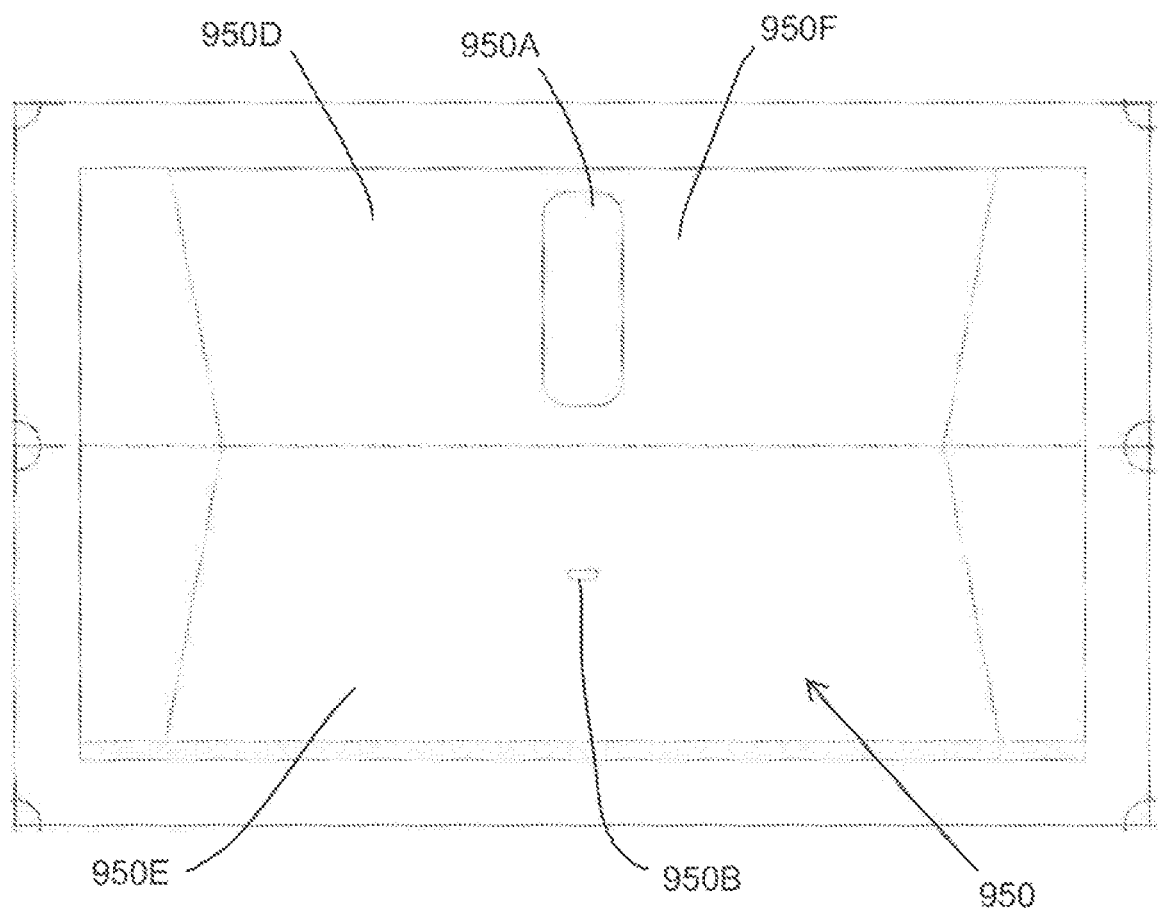
FIGS. 20-22 are top views of components for manufacturing the band as shown in FIGS. 15-19.
Figure 21:
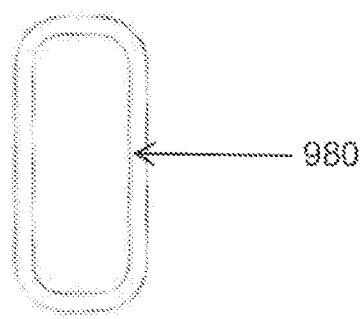

The band 920 may be assembled by using a heat press operation, with heat-activated films bonding the pieces of the band 920 together. In one embodiment, as described in U.S. patent application Ser. Nos. 14/946,682; 14/946,670; 14/946,674; and Ser. No. 14/946,691, the pieces of the material of the band 920 may be heat pressed to mold the material to define the pocket 940 and increase the rigidity of the material. The band 920 of FIGS. 6-7 is created in this manner. FIGS. 11-14 illustrate an example embodiment of a mold 970 that can be used to manufacture the band 920 using the components and techniques described in as described in the applications referenced above. The mold 970 includes two mold plates 971, 972 that are pressed together around the assembled band components, such that these components are received in a mold cavity 973 between the mold plates 971, 972 in an assembled manner. The mold plates 971, 972 each have an enlarged portion 974 that creates a secondary cavity 975 within the mold cavity 973, for molding the pocket 940. One or both plates 971, 972 may include one or more holes 978 to permit gases to escape during molding. A plug 976 is inserted between the layers forming the band 920 during the heat pressing, to form the inner shape of the pocket 940, as shown in FIGS. 12-14. As illustrated in FIGS. 12 and 14, the plug 976 includes a projection 977 that extends through the sensor opening 945 during the molding process. After the heat pressing is completed, the mold plates 971, 972 are separated, the plug 976 is removed from the pocket 940 (such as through the opening 942), and the assembled band 920 is removed from the mold 970. Additional manufacturing steps may then be taken. It is understood that the structure and configuration of the mold 970 and the components thereof may be changed for bands 920 having different sizes, shapes, structures, etc. After the process is complete, the assembly is removed from the mold, and the final structure of the band 920 is assembled as a flat piece. A protective shell may be placed within the cavity 941 to protect at least a portion of the module 930, and may be formed of a rigid material, such as a rigid plastic or fiber reinforced polymer (e.g., thermoplastic polyurethane), a metallic material, or other material. Various bonding, trimming, and closure strips may be used to fully define the band 920 in the final form as shown in FIGS. 6-7. FIG. 6 illustrates one embodiment of the band 920 with the module 940 received in the pocket 940, and FIG. 7 illustrates a similar band 920, as described elsewhere herein.

Figure 27:
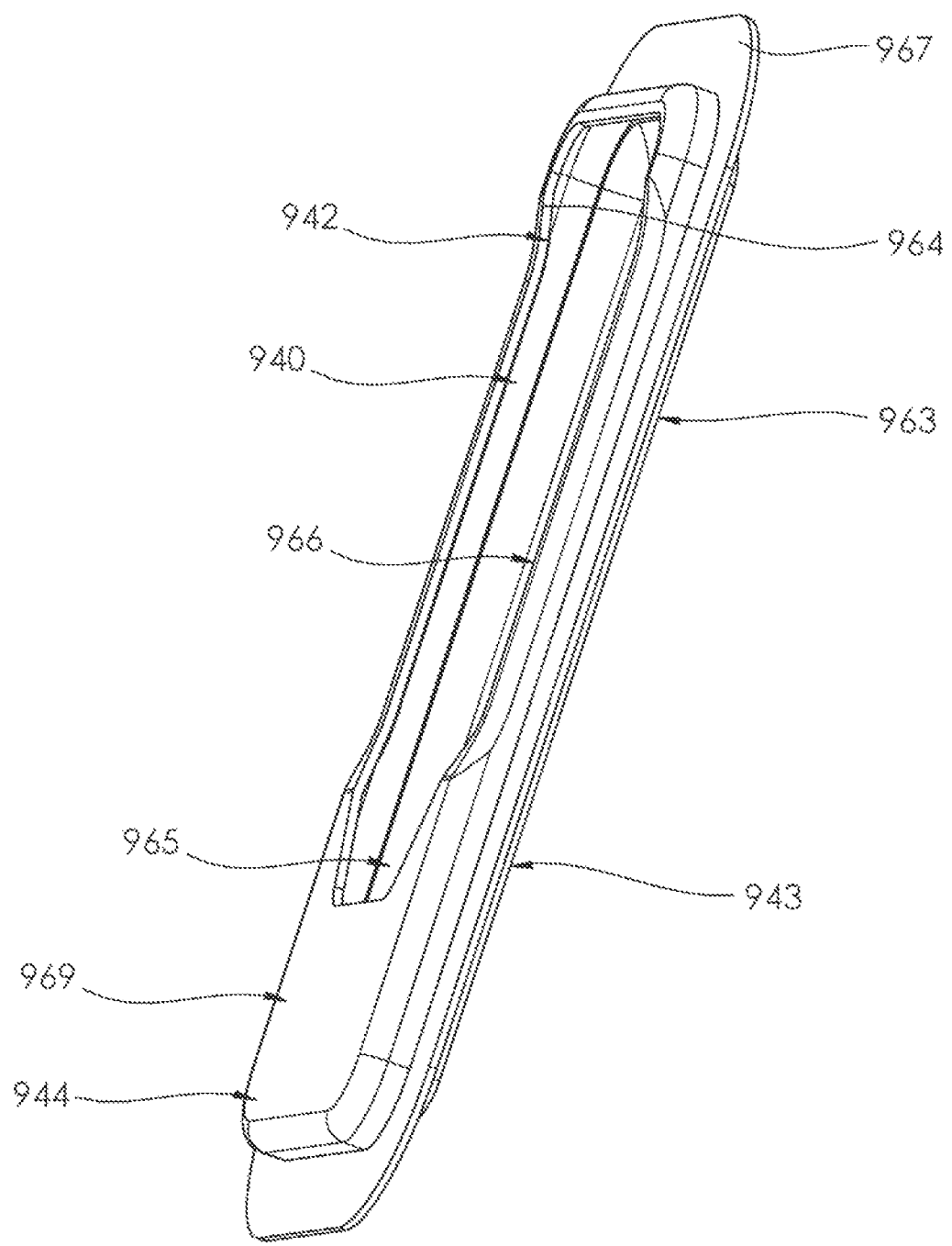
FIG. 27 is a side view of the housing of FIG. 23.
Figure 28:
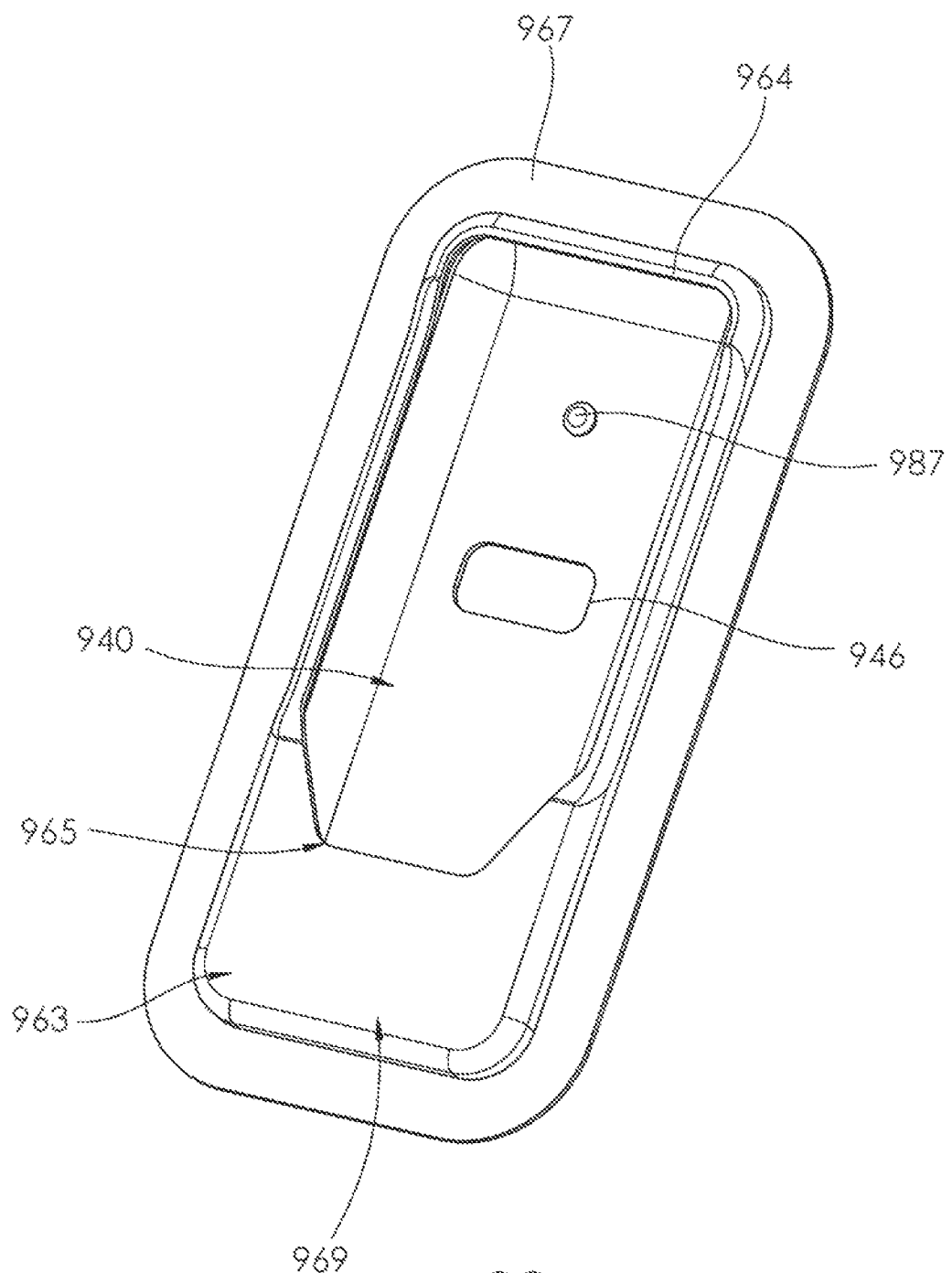
FIG. 28 is a bottom perspective view of the housing of FIG. 23.
Figure 29:
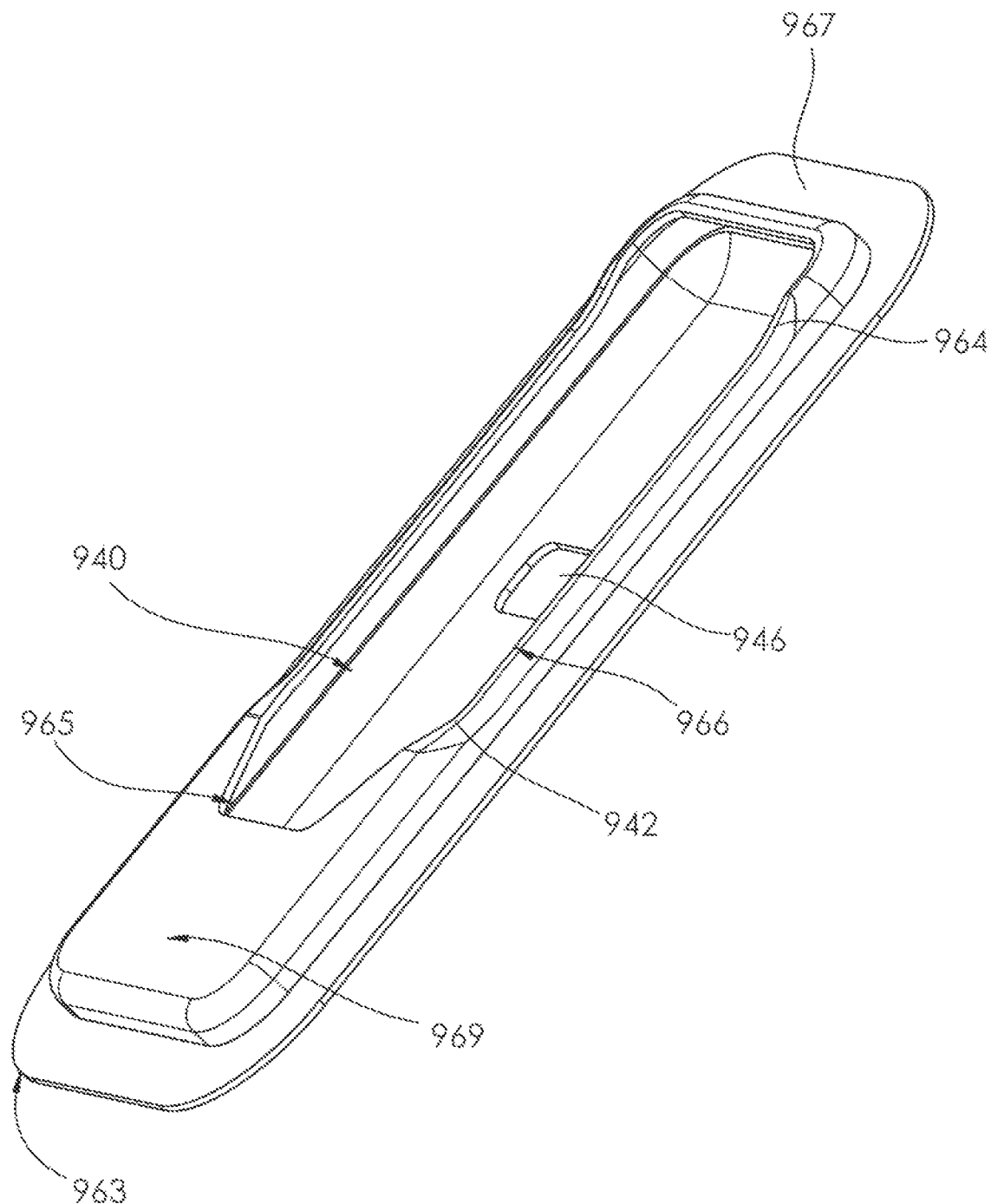
FIG. 29 is a bottom perspective view of the housing of FIG. 23.
Figure 30:
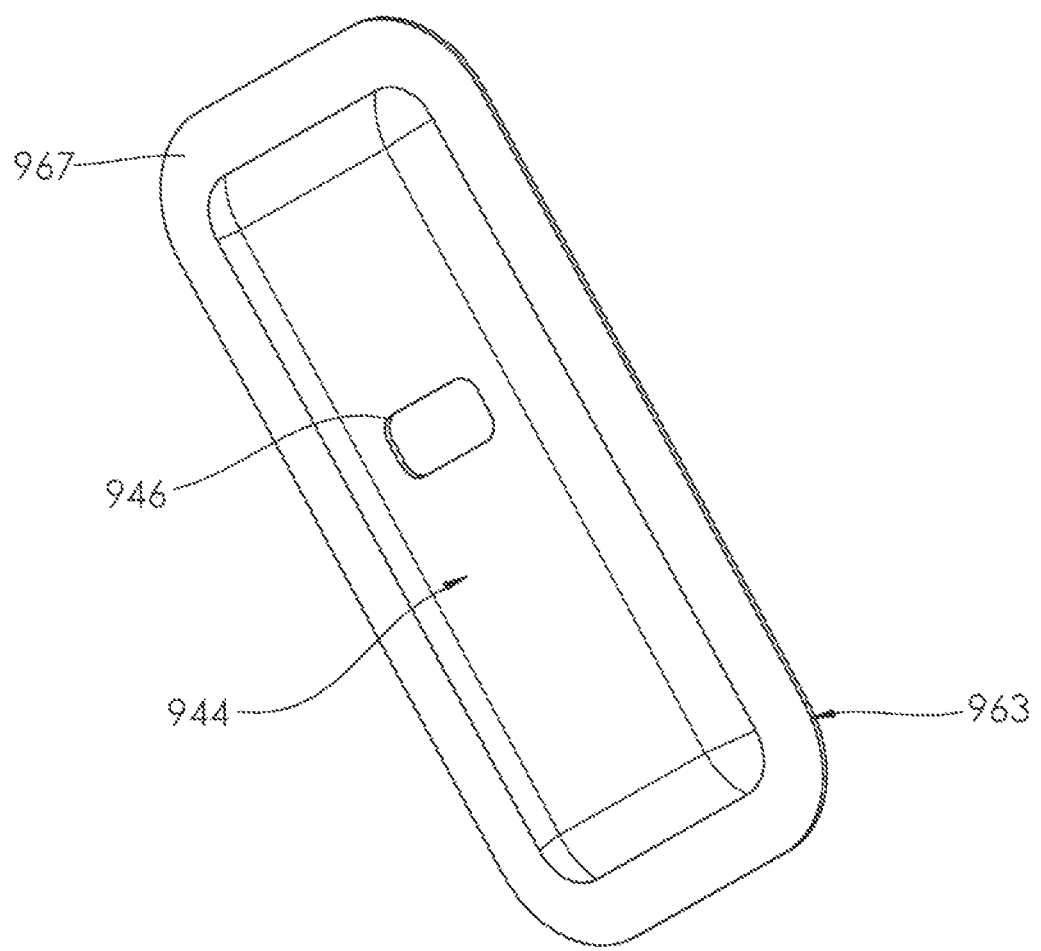
FIG. 30 is a top perspective view of the housing of FIG. 23.
Figure 31:
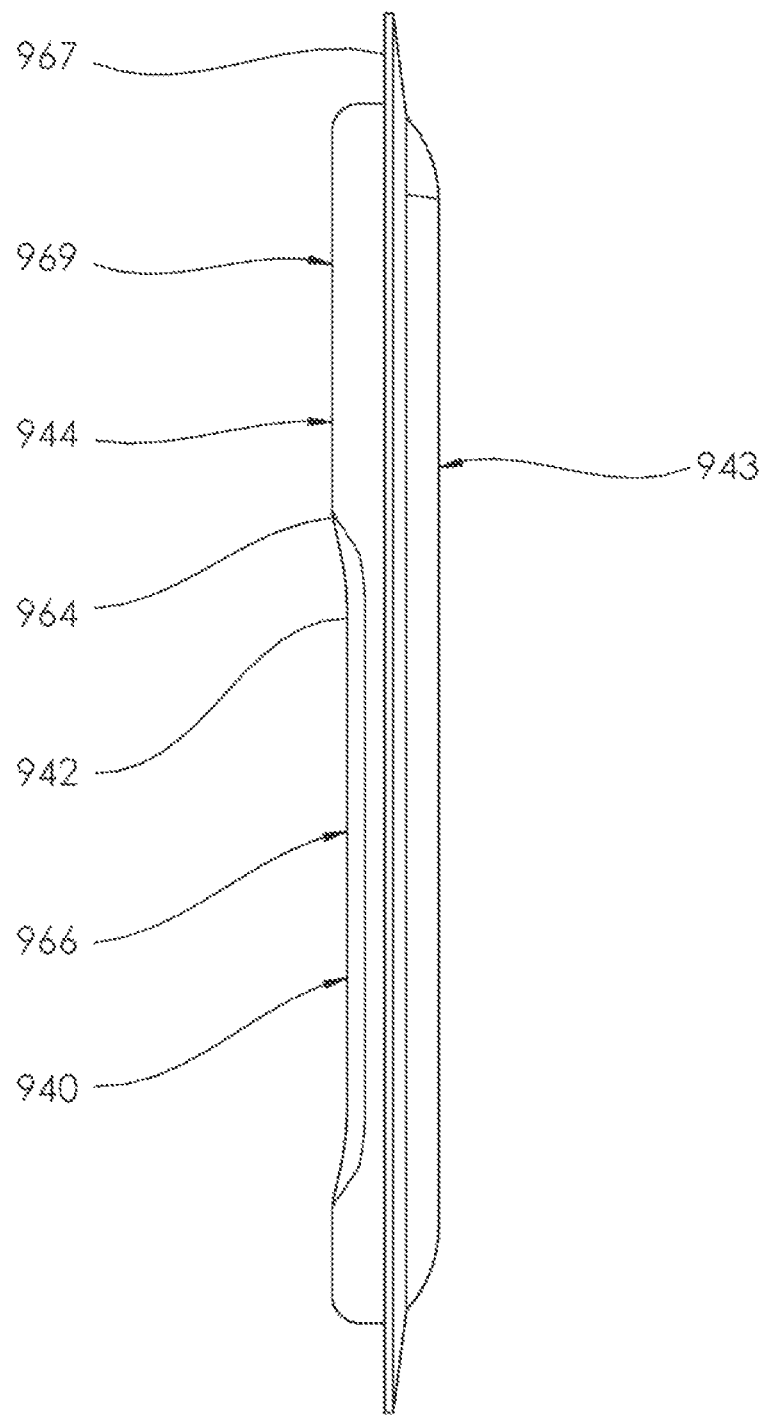
FIG. 31 is a side view of the housing of FIG. 23.

The band 920 in FIGS. 15-19 utilizes a housing 963 that is formed separately from the band 920 and is connected to the band 920 to form the pocket 940. One embodiment of the housing 963 is shown in FIGS. 23-24 and 27-31. The housing 963 may be made of a thermoplastic polyurethane (TPU) material and is formed in a single piece (e.g., by injection molding) in one embodiment, but may be partially or completely made from other materials, multiple pieces, and/or other techniques in other embodiments. The housing 963 in this embodiment is a moderately rigid shell that completely defines the cavity 941 and defines the opening 942 on the inner wall 944 and the window 946 on the outer wall 943. In one embodiment, the rigidity of the housing 963 may be sufficiently rigid to protect the module 930, and sufficiently flexible to permit manipulation of the button 933 by pressing on the button portion 947 of the band 920. The rigidity of the housing 963 may be greater than the rigidity of the fabric material forming the band 920. The housing 963 may also have a protrusion 987 on the outer wall 943 in one embodiment, to facilitate manipulation of the button 933 by the button portion 947 on the outer surface 928 of the band 920 and/or to enhance the "feel" of the button 933, as shown in FIG. 28. The protrusion 987 may lightly engage the button 933 or be in close proximity to the button 933, so that manipulation of the button 933 requires a small amount of movement/flexing of the adjacent portions of the housing 963. The embodiment of FIG. 28 has the protrusion 987 formed as a dome-shaped protrusion formed of an epoxy material applied to the inner surface of the outer wall 943. In other embodiments, the protrusion may be formed differently, such as being integrally formed (e.g., molded) with the housing 963, or may be structured or located differently. As shown in FIGS. 27-31, the housing 963 in the illustrated embodiment has a lip 964 that extends inwardly around the opening 942 and functions to retain the module 930 within the pocket 940. The opening 942 has a narrowed portion 965 that is configured to engage with the projection 939 of the module 930 to hold the projection 939 in place, and the lip 964 has recessed portions 966 located around the narrowed portion 965, as shown in FIGS. 27, 29, and 31. The recessed portions 966 permit the projection 939 to extend farther outwardly relative to the lip 964, in order to have better access to the user's skin. The housing 963 also has a wall 969 configured to form a pocket enclosing and holding the connector(s) 935 of the module 930.

In one embodiment, the housing 963 further has a flange 967 that extends outwardly around at least a portion of the periphery of the housing 963 and is configured for connection to the band 920. In the embodiment shown in FIGS. 23-24 and 27-31, the flange 967 extends generally in a single plane around the entire periphery of the housing 963. In other embodiments, the flange 967 may have a different configuration (e.g., intermittent), or may not be present. Generally, the exterior surfaces of the housing 963 shown in FIGS. 23-24 and 27-31 are smoothly contoured, both for aesthetics and for increased comfort when the housing 963 engages the user's body.

The window 946 of the housing 963 may be an empty passage in one embodiment, or may have a transparent filler in another embodiment, in order to resist ingress of material from the outer surface 928 of the band 920. In further embodiments, the window 946 may include a light-scattering and/or light-collecting structure, to enhance transmission of the light through the window 946, making light from the display 934 appear brighter at the outer surface 928 of the band 920 from a wide variety of angles. For example, the window 946 may include a clear silicon print aligned with the window 946 in one embodiment. As another example, the window 946 may have a silkscreen fabric or fine weave of material aligned with the window 946 in another embodiment. As a further example, the window 946 may have a film connected over the window 946 in yet another embodiment, such as a polycarbonate film that is connected by adhesive or sonic welding. It is understood that these structures may be located within the window 946 and/or positioned over the inner and/or outer surfaces of the window 946, in various embodiments. This may be particularly advantageous when used with a housing 963 as shown in FIGS. 27-31, which may have a significant wall thickness between the display 934, which may make the light darker or more difficult to detect from peripheral angles.

FIGS. 20-40 illustrate one embodiment of a set of components and a method for manufacturing the band 920 as shown in FIGS. 15-19, which may be made from a piece of fabric that is folded over onto itself to form two layers and joined by stitching and/or adhesive applied between the two layers. It is understood that the band 920 may be made from two or more separate pieces joined together in another embodiment. The band 920 may use a heat press operation in assembly, with heat-activated films bonding the pieces of the band 920 together. The embodiment of the method shown in FIGS. 32-40 utilizes more localized heat pressing, and does not involve heat pressing the entire band 920 as in the method described above with respect to FIGS. 11-14. FIGS. 20-31 illustrate components that may be used in the method illustrated in FIGS. 32-40, which are described in greater detail below with respect to FIGS. 32-40.

Figure 32:
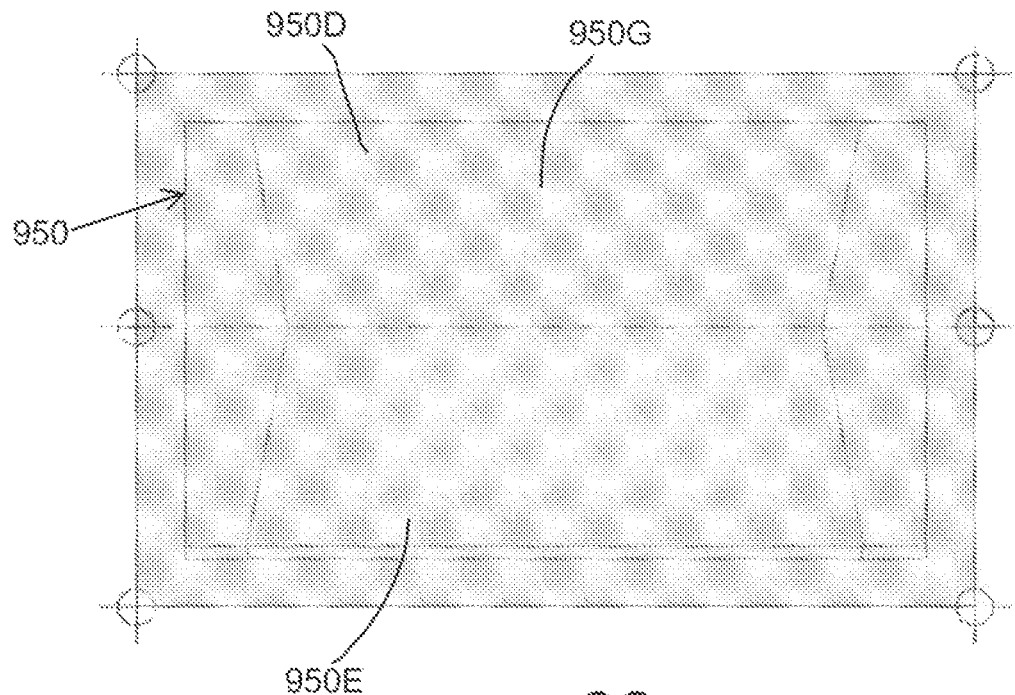
FIGS. 32-40 are plan views schematically illustrating a method of manufacturing a band according to aspects of the disclosure, using the components and housing of FIGS. 20-31.
Figure 33:
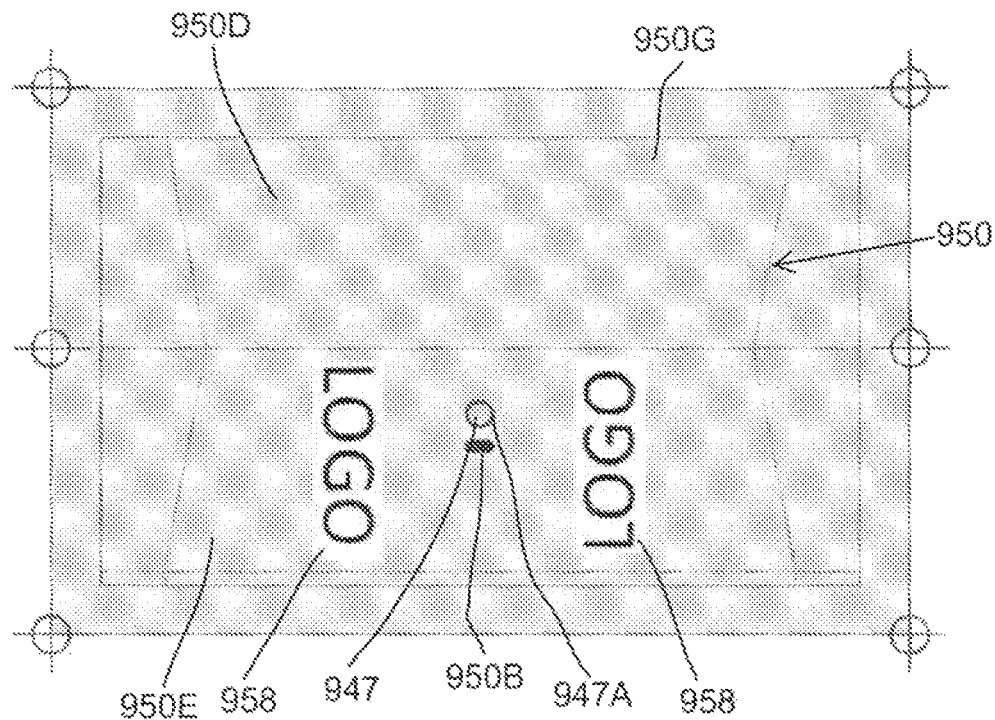
Figure 34:
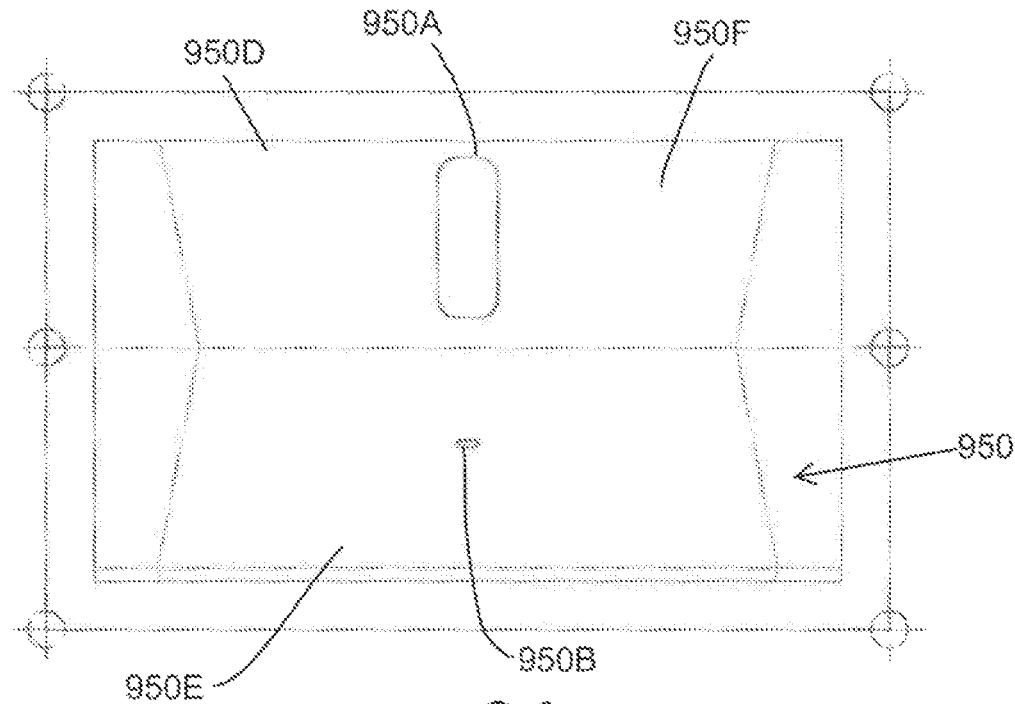

In the embodiment of FIGS. 20-40, a main body piece 950 is formed (e.g., cut) from an fabric material with elastic properties (e.g., a polyethylene-based material), as shown in FIG. 32, with fold lines indicated by broken lines. Graphics 958 may be applied to the outer surface 928 of the band 920, such as by screen printing as shown in FIG. 33, if desired. The main body piece 950 has a first hole 950A for the housing 963 to extend through the band 920 and be accessible from the inner surface 927 of the band 920 and a second hole 950B aligned with and/or forming part of the window 946. The holes 950A-B may be formed in the main body piece 950 by cutting or laser etching in one embodiment, as shown in FIG. 34, and may be formed before or after application of the graphics (if graphics are applied). The central fold line divides the main body piece 950 into a first or inner portion 950D forming the inner surface 927 of the band 920 and a second or outer portion 950E forming the outer surface 928 of the band 920, and the main body piece 950 has an inside surface 950F and an outside surface 950G (illustrated by shading in FIGS. 32-40. The outside surface 950G forms the inner and outer surfaces 927, 928 of the band 920 after assembly, and the inside surface 950F is folded over on itself during manufacturing and forms no portion of the inner and outer surfaces 927, 928 of the band 920. It is understood that graphics 958 that are configured to be visible on the inner or outer surface 927, 928 of the band 920 may be applied to the outside surface 950G of the main body piece 950.

Figure 35:
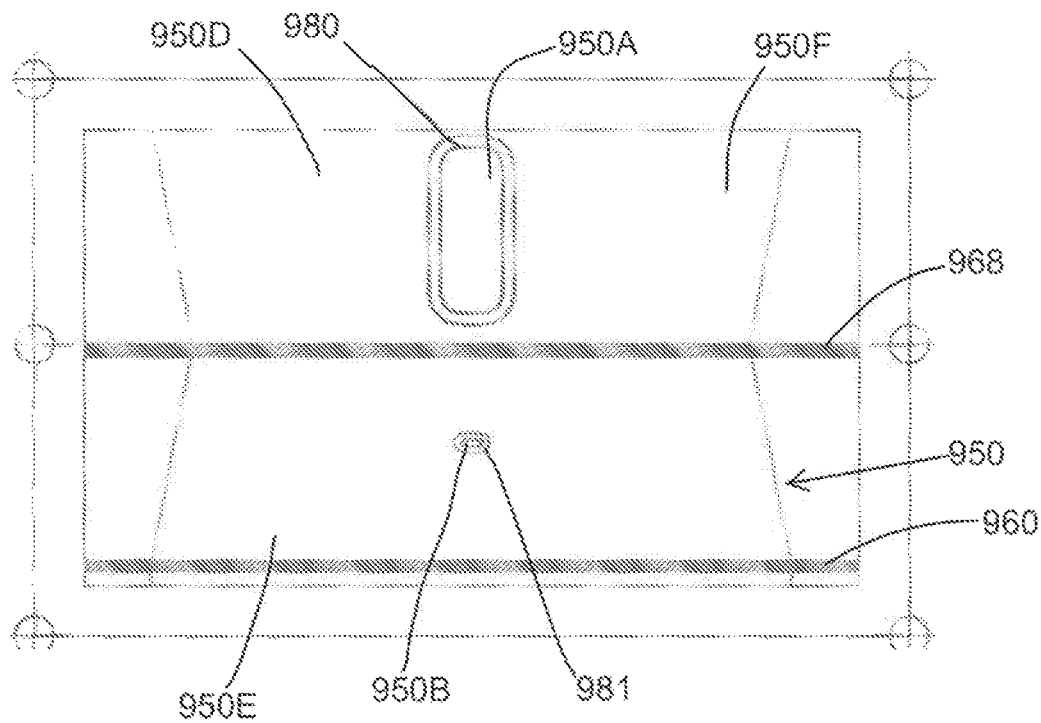

As shown in FIG. 35, an frame bond 980 is applied around the first hole 950A on the inside surface 950F of the first portion 950D and is configured for bonding to the flange 967 of the housing 963, and a light alignment bond 981 is applied around the second hole 950B on the inside surface 950F of the second portion 950E and is configured for bonding to the housing 963 around the window 946. In this configuration, the light alignment bond 981 resists displacement of the hole 950B with respect to the window 946, which may cover the window 946 and block light passage. Although the light alignment bond 981 is shown as being applied in FIG. 35, in one embodiment, the light alignment bond 981 may be applied at the stage illustrated in FIG. 38, immediately before folding the inner and outer portions 950D-E together. These bonds 980, 981 may initially be lightly bonded by slight application of heat and pressure in one embodiment, to hold the components in place during assembly, and then may be normally bonded later during assembly. A strip 960 of bonding material is also placed across the edge of the inside surface 950F of the outer portion 950E of the main body piece 950, configured to bond the edges of the inner and outer sides 950D-E together after folding, as shown in FIG. 35. Another bonding strip 968 may also be placed on the inside surface 950F along the central fold line, in order to provide additional strength and structural support to the bottom end 924 of the finished band 920, as also shown in FIG. 35.

Figure 36:
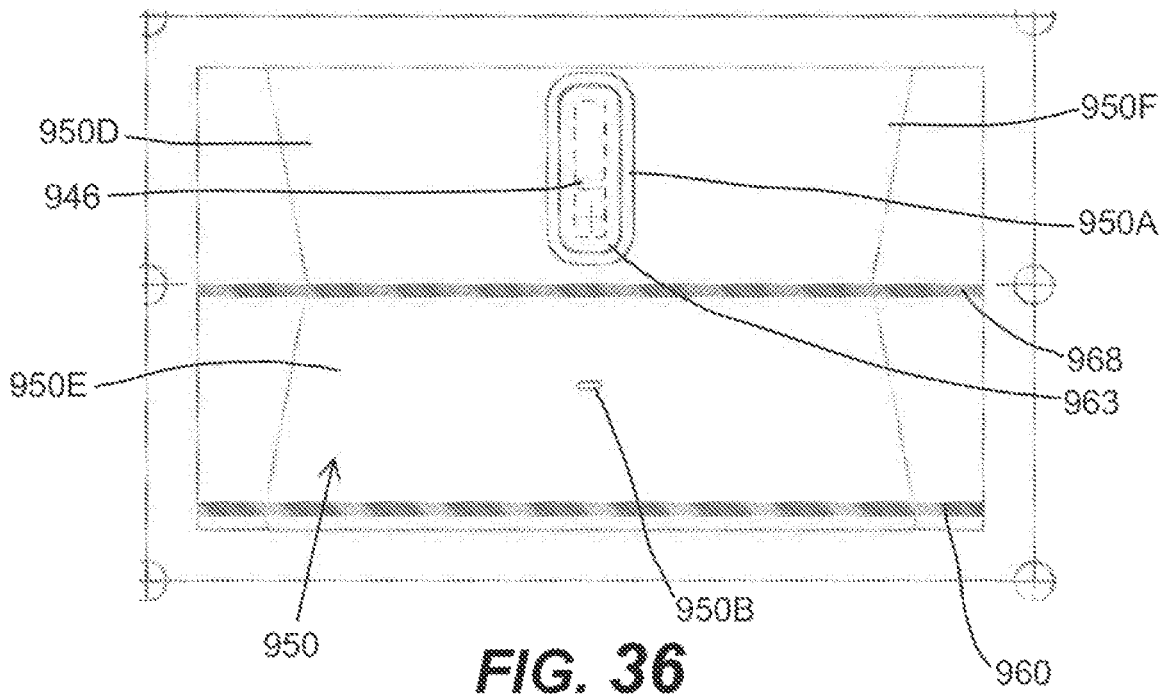
Figure 37:
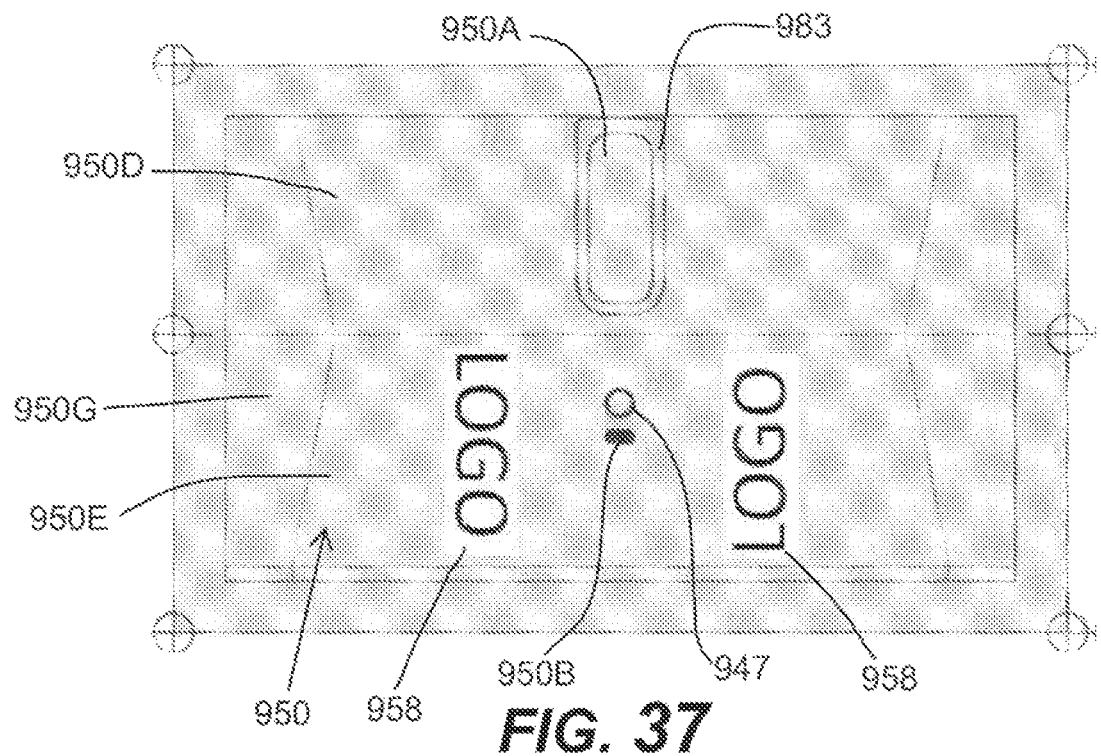

The housing 963 may then be connected to the band 920, such that the flange 967 sits around the periphery of the hole 950A and the portion of the housing 963 including the opening 942 projects through the hole 950A, as shown in FIG. 36. The flange 967 may be connected to the inside surface 950F of the main body piece 950 by stitching around part or all of the flange 967 and/or bonding to the frame bond 980 in one embodiment. As described above, in one embodiment, the flange 967 may be lightly bonded to the inside surface 950F by the frame bond 980 prior to stitching, and then more strongly bonded later on during assembly. After the housing 963 is connected to the band 920, a trim piece 983 may be connected on the outside surface 950G of the inner portion 950D of the main body portion 950, as shown in FIG. 37. This trim piece 983 forms part of the inner surface 927 of the band 920 and covers the connection between the housing 963 and the main body portion 950. The trim piece 983 may be formed of a heat-activated material as described herein and may be heat pressed into place in one embodiment, and the trim piece 983 may be lightly pressed at first and then more strongly pressed at a later time, or may be fully pressed initially, in various embodiments.

Figure 22:
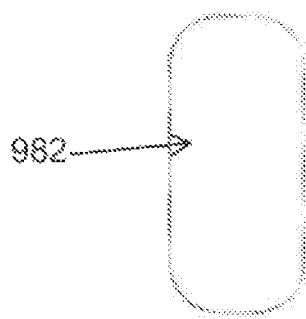
Figure 23:
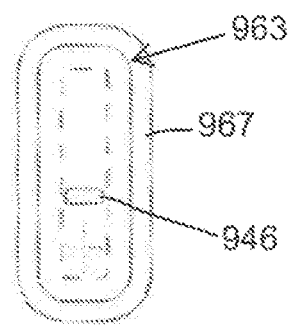
FIG. 23 is a top view of a housing of the band as shown in FIGS. 15-19.
Figure 24:
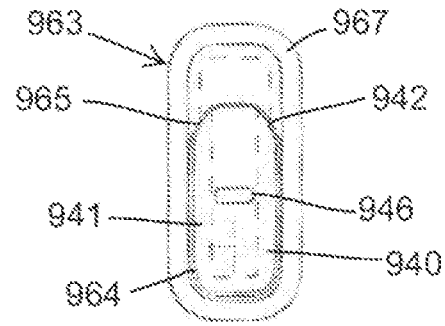
FIG. 24 is a bottom view of the housing of FIG. 23.
Figure 25:
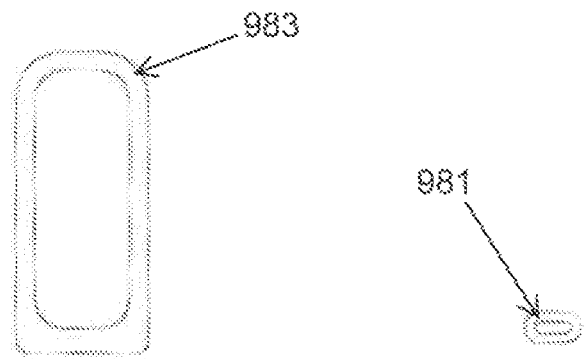
FIGS. 25-26 are top views of additional components for manufacturing the band as shown in FIGS. 15-19.
Figure 26:
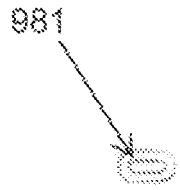

In one embodiment, a support piece 982 as shown in FIG. 22 may also be positioned between the housing 963 and the inside surface 950F of the outer portion 950E of the main body piece 950 prior to folding of the main body piece 950. The method illustrated in FIGS. 32-40 does not include this support piece 982, and the support piece 982 (if used) may be connected to the housing 963 and the main body piece 950 between the steps in FIGS. 37-38 in one embodiment. The support piece 982 may be formed of a heat-activated material as described herein and may be heat pressed into place. The support piece 982 may have a hole (not shown) cut in alignment with the window 946. This support piece 982 may be included if graphics are printed on or around the areas of the band 920 located over the pocket 940 and housing 963, to resist stretching or distortion of the graphics. If no graphics are printed in this location, the support piece 982 may not be included.

Figure 43:
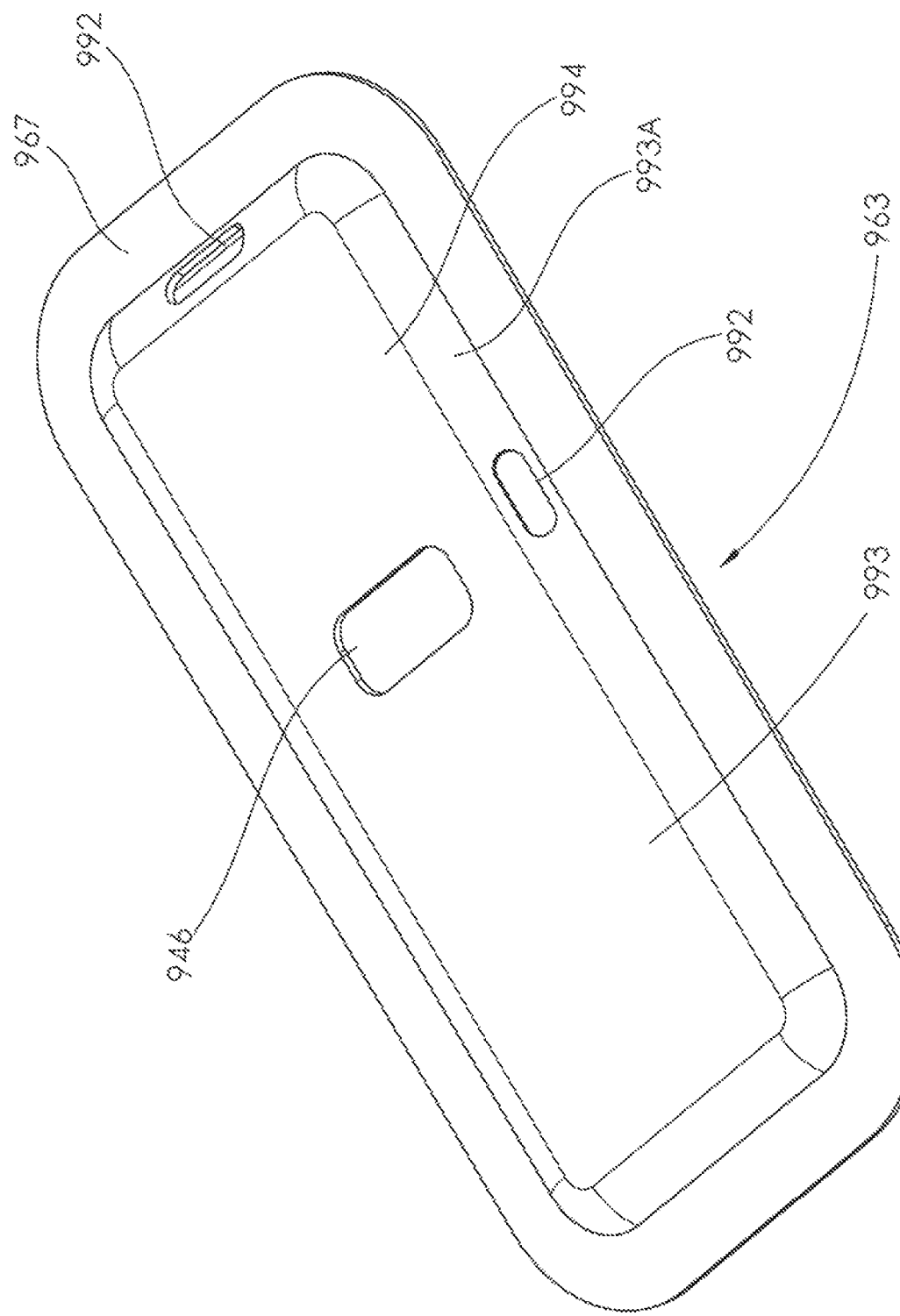
FIG. 43 is a top perspective view of another embodiment of a housing usable in manufacturing a band according to aspects of the disclosure.
Figure 44:
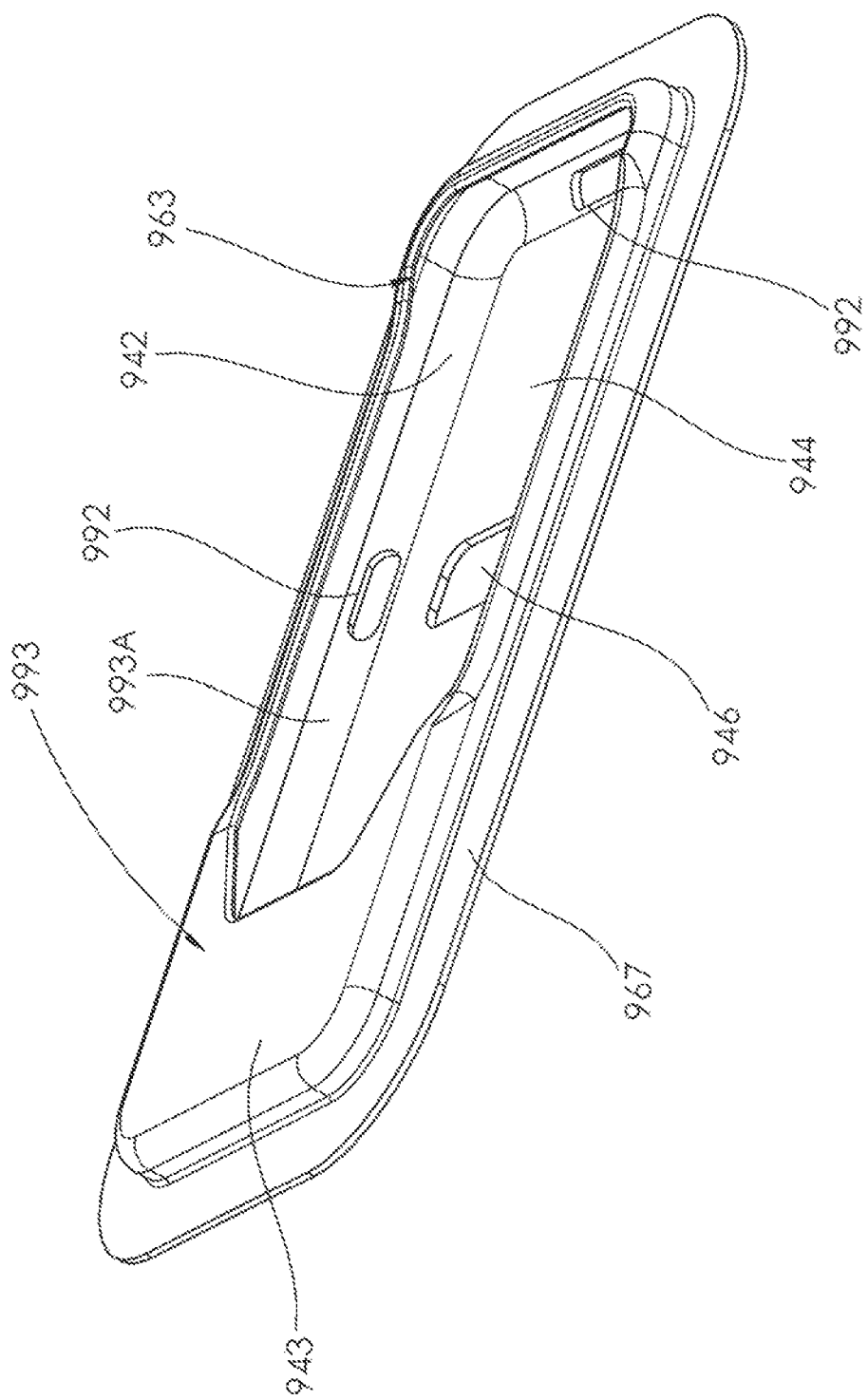
FIG. 44 is a bottom perspective view of the housing of FIG. 43.
Figure 45:
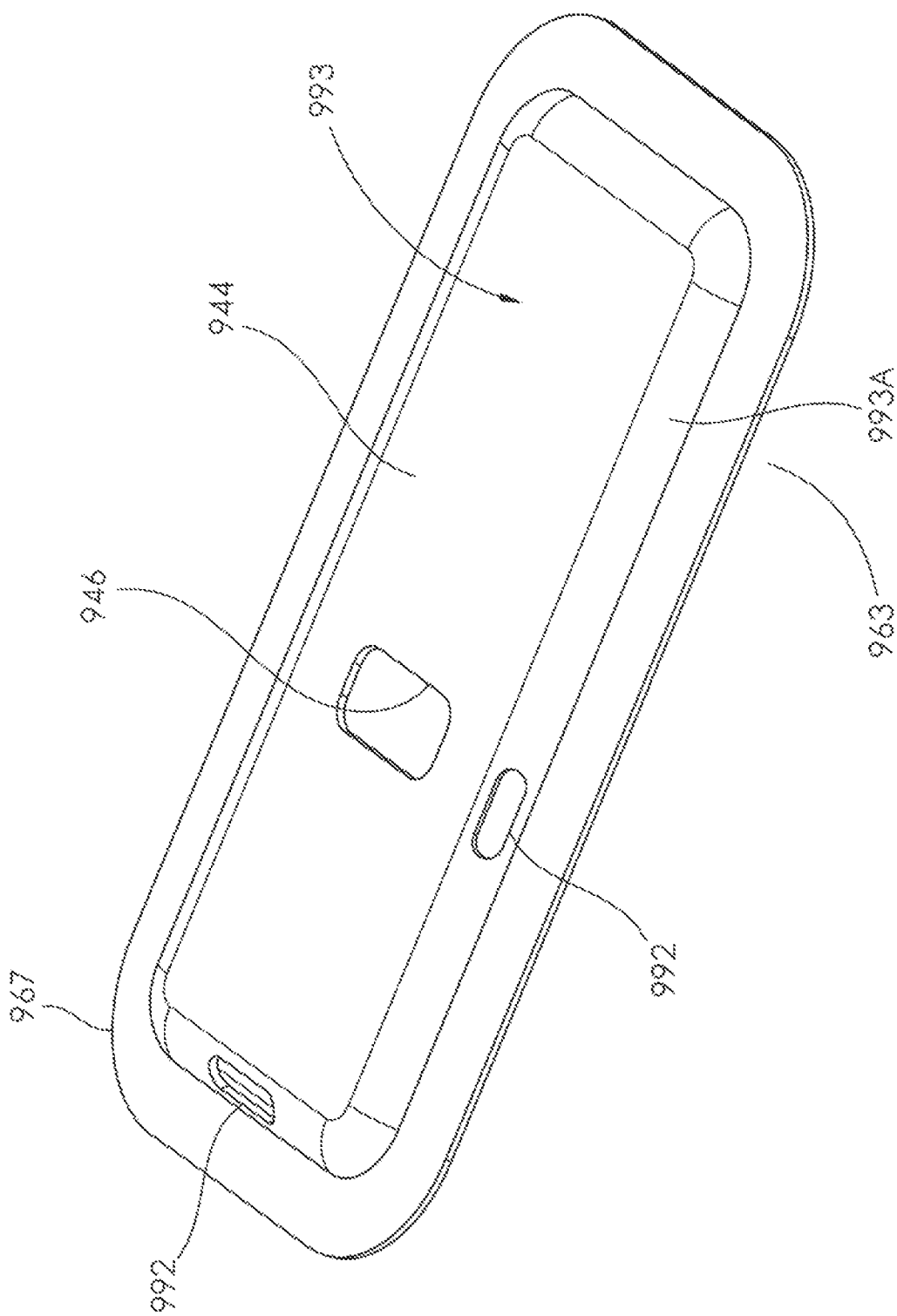
FIG. 45 is a top perspective view of the housing of FIG. 43.
Figure 46:
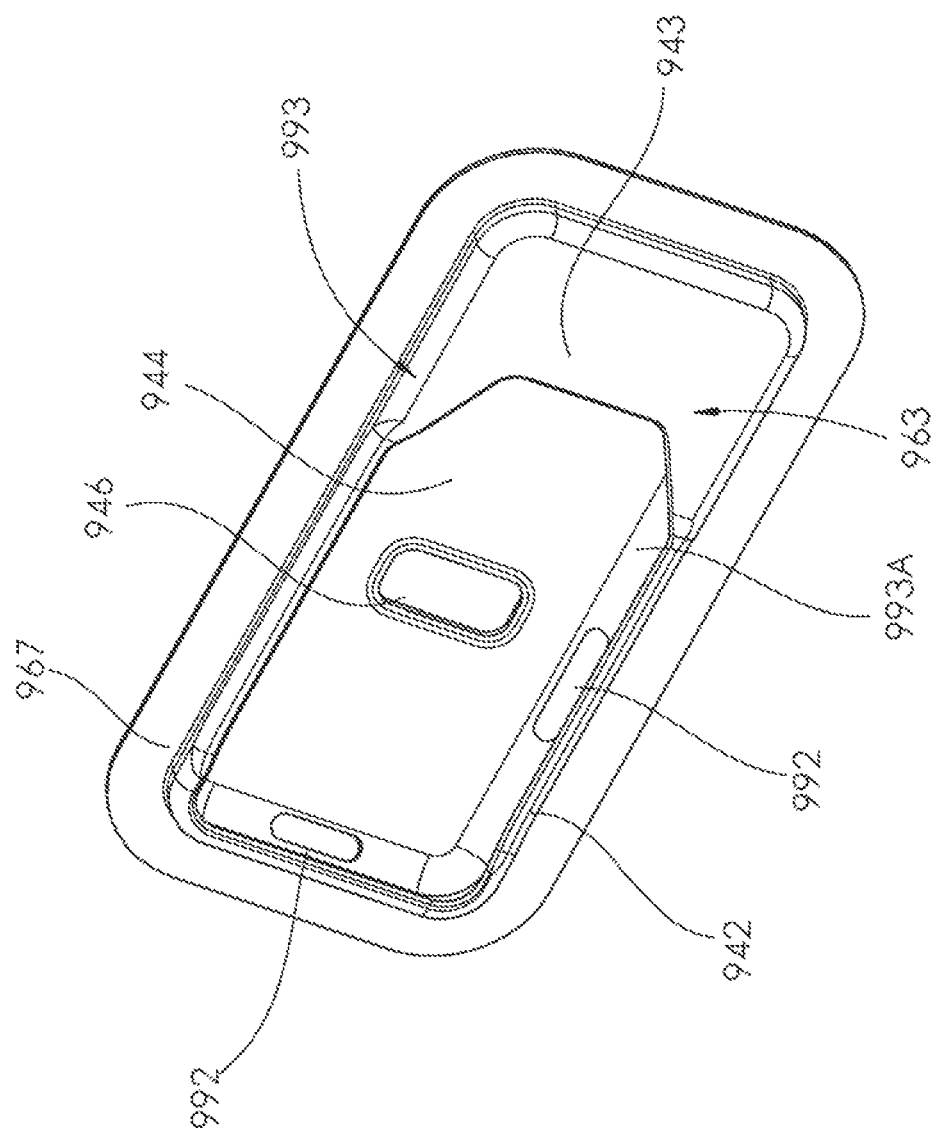
FIG. 46 is a bottom perspective view of another embodiment of a housing usable in manufacturing a band according to aspects of the disclosure.
Figure 47:
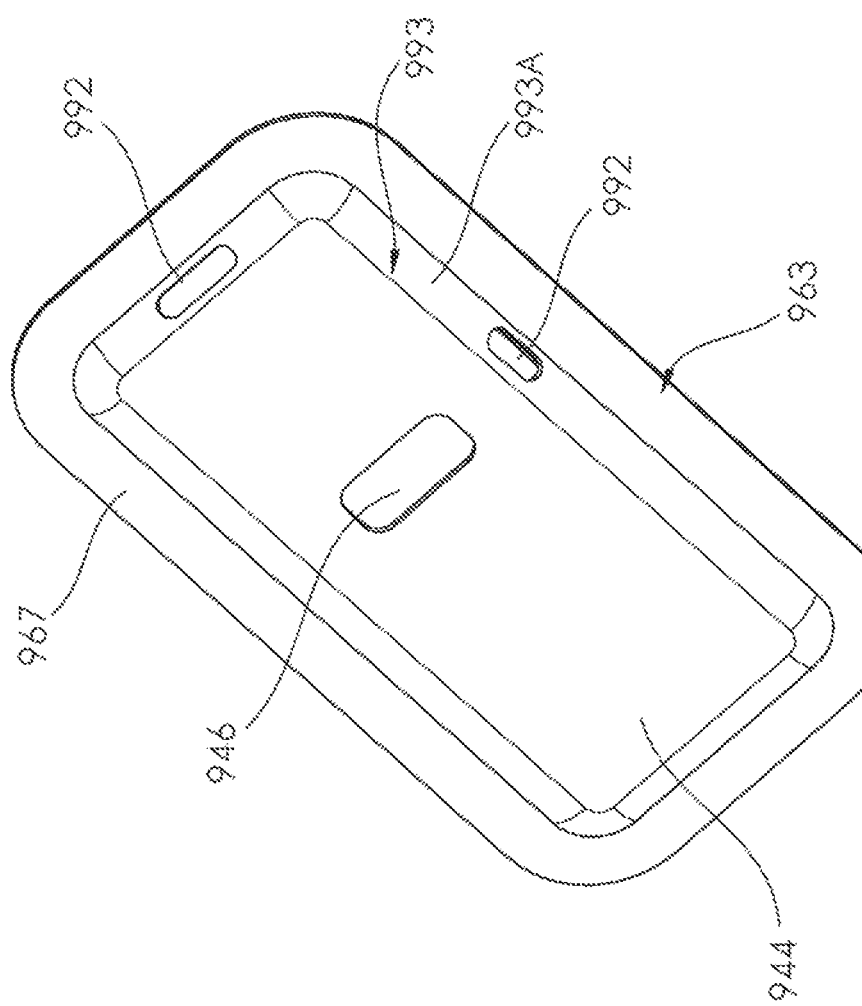
FIG. 47 is a top perspective view of the housing of FIG. 46.

FIGS. 43-45 illustrate an embodiment of a housing 963 that is usable in manufacturing a band 920 according to various embodiments described herein. FIGS. 46-47 illustrate another embodiment of a housing 963 that is configured in a similar manner to the housing 963 in FIGS. 43-45, and the descriptions herein with respect to FIGS. 43-45 apply equally to FIGS. 46-47 unless stated otherwise. The housing 963 in FIGS. 43-45 includes one or more slots 992 extending through one or more of the walls 993 of the housing 963. It is understood that the walls 993 of the housing 963 define the cavity 941 and may include the outer wall 943, the inner wall 944, and potentially other walls as well.

The slots 992 may help avoid accumulation of moisture (e.g., sweat) within the housing 963 during use, by allowing the moisture to escape easily from the housing 963. In one embodiment, the housing 963 may include at least one slot 992 that is located at the end of the housing 963 positioned closest to the bottom end 924 of the band 920, i.e., the end of the housing 963 that is configured to be at the bottom when the band 920 is worn on a user's arm in a normal standing position. The housing 963 in FIGS. 43-45 has a slot 992 on the bottom end of the outer wall 943 in this position, when the housing 963 is mounted on the band 920 in the orientation shown in FIGS. 16-17 and 40. In this position, the downward-facing slot 992 promotes increased moisture passage, because gravity tends to force moisture toward the slot 992. Centrifugal force generated by swinging the arm during exercise may also force moisture toward the downward-facing slot 992. The housing 963 may also have one or more additional slots 992 in other locations in various embodiments. For example, the housing 963 may also have slots 992 in one or both of the left and right sides of the inner wall 944, as in the embodiment of FIGS. 43-45. These side slots 992 may also promote increased moisture passage through gravity and/or centrifugal force, as one of these slots 992 will be downward-facing when the user's arm is bent at a 90° angle, as is common during running and many other exercises.

The housing 992 may have additional slots 992 and/or slots 992 located in different positions in other embodiments, which may or may not be positioned in locations where gravity and/or centrifugal force promote flow of moisture. For example, if the housing 963 is positioned in a different orientation in another embodiment, then the end of the housing 963 that is downward-facing may be different. In such an embodiment, the slot(s) 992 may be located differently, in order to promote increased moisture passage, e.g., by having a slot 992 at the opposite end of the housing 963 as the end slot 992 in FIGS. 43-45. In a further embodiment, the housing 963 may have slots 992 located at the bottom-left and bottom-right corners. Still further configurations may be used in other embodiments.

The slots 992 in the embodiment of FIGS. 43-45 are formed in the outer wall 943 of the housing 963. These slots 992 may be considered to be formed at least partially or entirely in side walls 993A of the housing 963 that form part of the outer wall 943 and extend transversely to the flange 967. In this position, the slots 992 are positioned only on the portions of the housing 963 that are located outwardly (toward the outer side 928 of the band 920) from the flange 967. This configuration permits moisture to pass from inside the housing 963 to the exterior of the housing and to be absorbed by the material of the band 920. In other embodiments, the slots 992 may additionally or alternately be located elsewhere. For example, the housing 963 may include one or more slots 992 in the inner wall 944 that allow moisture to pass to the exterior the band 920, or the housing 963 may have other exposed surfaces (such as in a differently-configured band 920) that may have slots 992 therein. Additionally, the size(s) of the slot(s) 992 may affect the moisture passage properties, as larger slots 992 can assist in breaking any meniscus that may form from moisture accumulation. In one embodiment, the slot 992 at the end of the housing 963 may be at least 50% of the width of the wall 993 in which it is located (i.e., not including the flange 967), and the slot(s) 992 on the side walls 993 of the housing 963 may each be at least 20% of the length of the side wall 993 in which it is located. Further, the housing 963 may have a surfactant applied to the inner surfaces of the housing 963, in order to enhance the ability of moisture to travel toward the holes and break up any meniscus that may form. The use of a surfactant may enable the use of smaller slots 992.

The slots 992 may be formed using any of a number of different forming techniques, in various embodiments. For example, in one embodiment, the slot(s) 992 may be formed in the housing 963 after the housing is formed, such as by using laser cutting, mechanical cutting, thermal cutting, or other cutting techniques; machining techniques; or other material removal techniques. In another embodiment, the slot(s) 992 may be formed as part of the forming process, such as by pressing or molding the material of the housing 963 with a tool configured to form the slot(s) 992. For example, a single-piece, injection molded TPU housing 963 as described above may be injection molded into a cavity that forms the slot(s) 992. Other techniques known in the art may be used as well.

Figure 41:
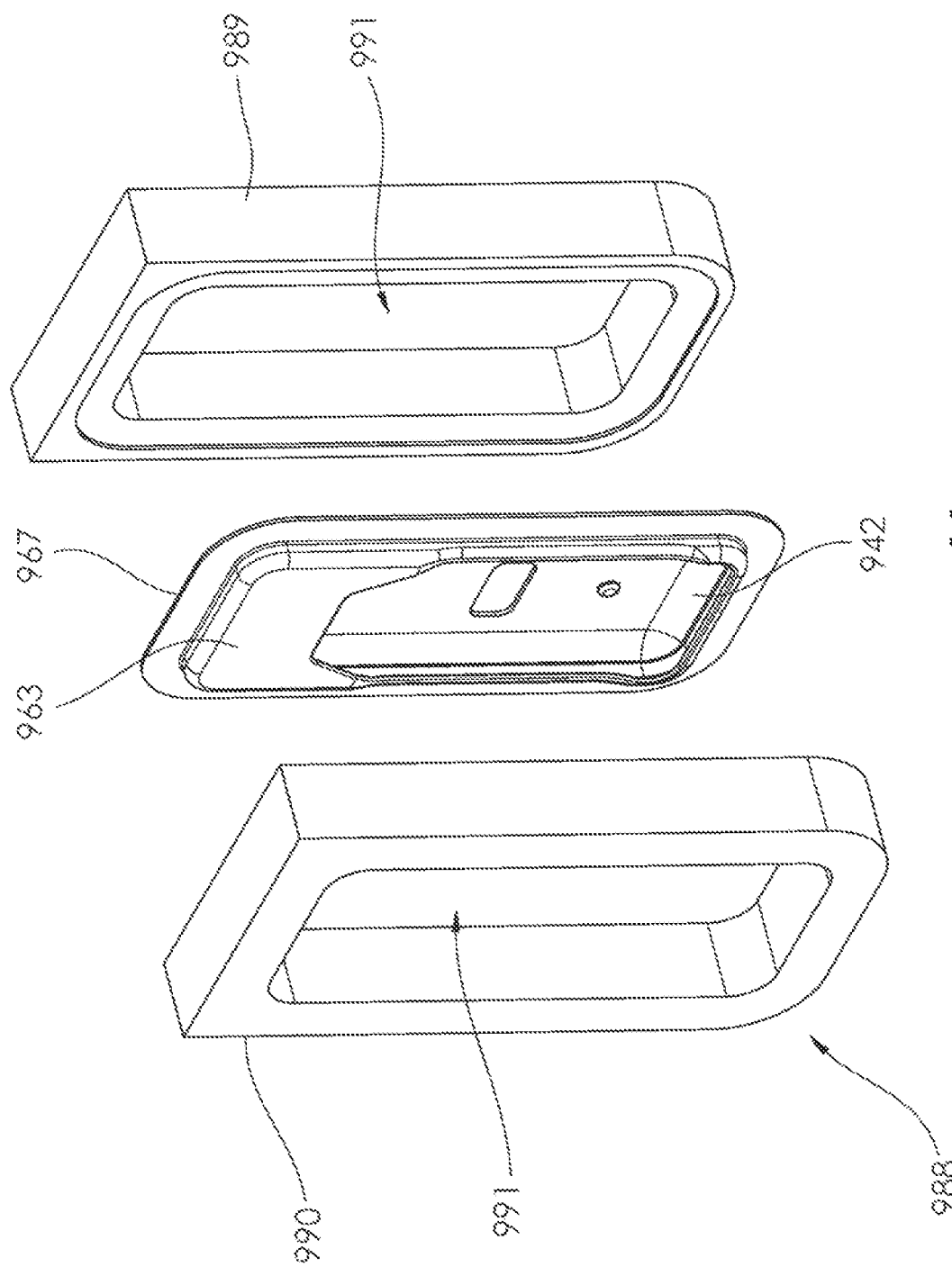
FIG. 41 is a perspective view schematically illustrating one embodiment of a mold for heat pressing a portion of a band according to aspects of the disclosure, along with the housing of FIG. 23, which is usable in connection with the method of FIGS. 32-40.
Figure 42:
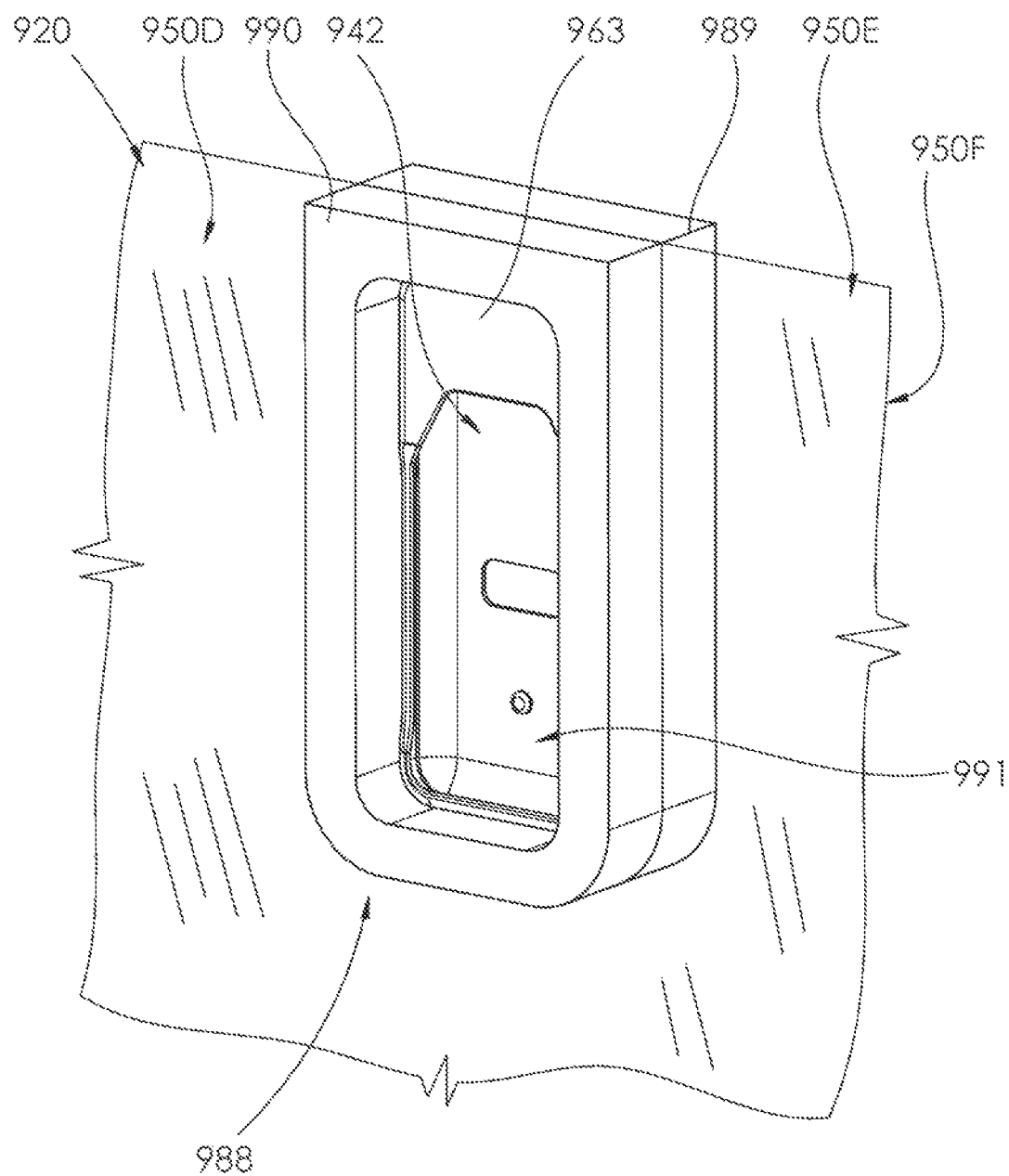
FIG. 42 is a perspective view schematically illustrating use of the mold of FIG. 41 in operation.

FIGS. 41-42 illustrate one embodiment of a heat press assembly 988 configured for heat pressing around the flange 967 of the housing 963 after the housing 963 is connected to the band 920, e.g., by stitching, as described herein with respect to FIG. 36. The heat press assembly 988 as shown in FIGS. 41-42 includes two opposed mold pieces 989, 990 that are configured for heat pressing around the flange 967 of the housing 963. The band 920 is illustrated schematically in FIG. 42, to show that the heat press assembly 988 is configured for heat pressing the band 920 along with the housing 963. In operation, the first mold piece 989 is positioned on the inside surface 950F of the inner portion 950D of the main body piece 950, and the second mold piece 989 is positioned on the outside surface 950G of the inner portion 950D of the main body piece 950. The mold pieces 989, 990 are annular in shape, each having an internal opening 991, so that the mold pieces 989, 990 are configured to press only around the flange 967 of the housing 963. In this configuration, the main body of the housing 963 is received within the opening 991, so that the mold pieces 989, 990 do not press the main body of the housing 963 or the adjacent portions of the band 920, which localizes the heat application and avoids creating unwanted marks or discolorations on the non-pressed portions of the band 920 and housing 963. The trim piece 983 shown in FIG. 37 may be applied prior to operation of the heat press assembly 988 in one embodiment, and the shapes of the mold pieces 988, 989 conform to the shape of the trim piece 983 as shown. The heat press assembly 988 may be applied to the band 920 and housing 963 following the assembly steps shown in FIGS. 36 and 37, and before the band 920 is folded over in FIG. 38 (discussed below). Additional pieces of heat-sealable material may be used in various positions, in connection with the heat press assembly 988. For example, the support piece 982 in FIG. 22 may also be applied before operation of the heat press assembly 988, as discussed herein. It is understood that the configuration of the mold pieces 988, 989 may vary depending on the shapes and configurations of the housing 963 and the trim piece 983 (or other pieces of heat sealable material that may be used).

Figure 38:
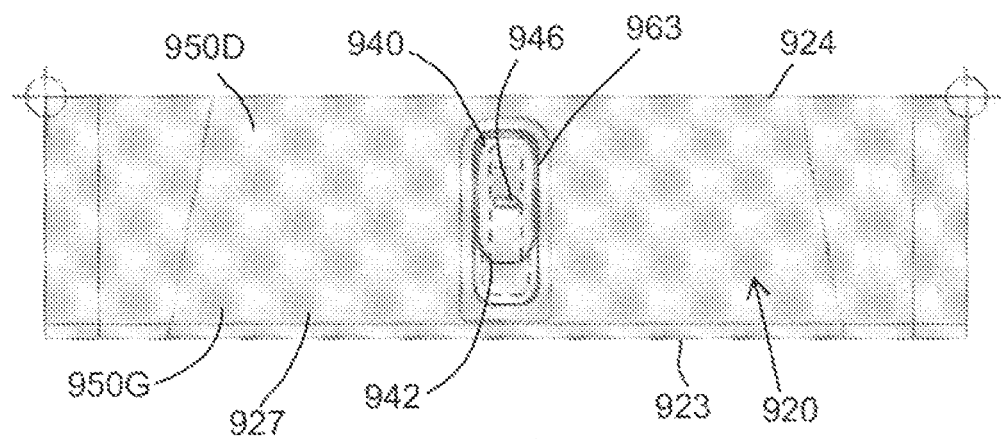
Figure 39:
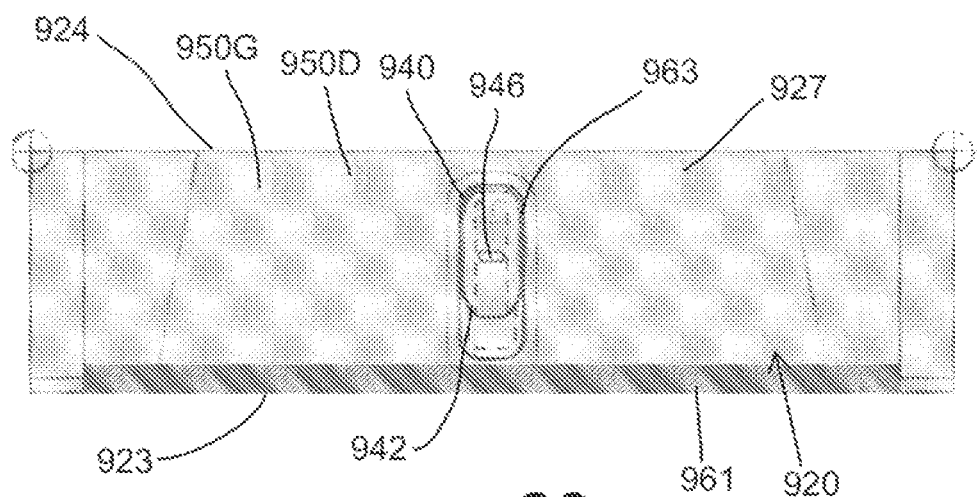
Figure 40:
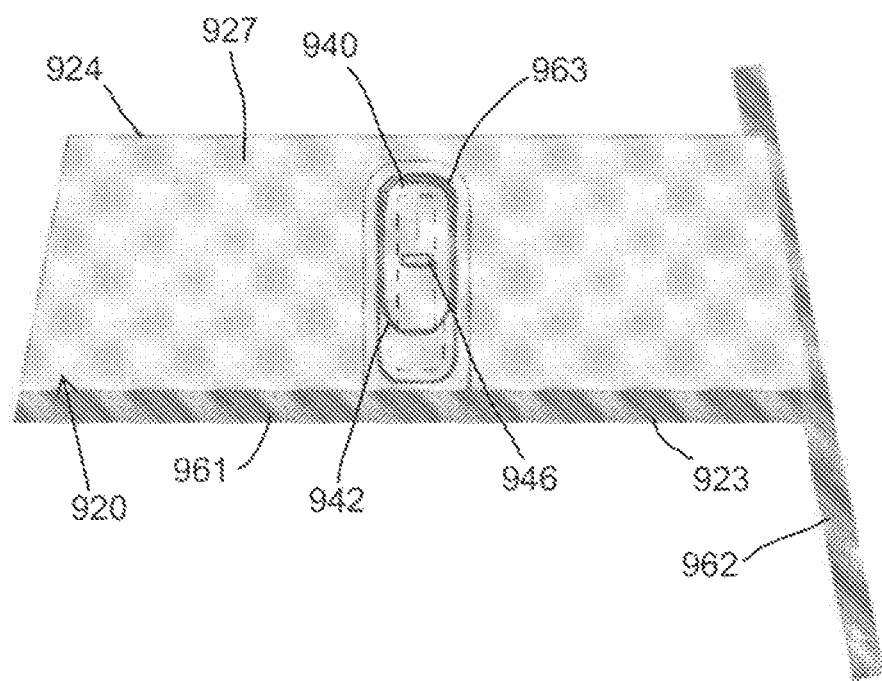

The main body piece 950 is then folded over so that the inner and outer portions 950D-E confront each other, as shown in FIG. 38. The outside surface 950G of the inner and outer portions 950D-E forms the inner and outer surfaces 927, 928 of the band 920, respectively, and the inside surface 950F is located internally within the band 920 in this configuration. A seam bonding strip 961 is placed along the edge where the folded ends of the inner and outer portions 950D-E meet, in order to cover the edges, as shown in FIG. 39. In one embodiment, the strips 960, 961, 968, frame bond 980, the trim piece 983, the light alignment bond 981, and optionally the support piece 982 (if present) may be bonded completely at this point in the process, such as by localized bonding techniques. For example, the bonding may be accomplished by bonding each piece individually and sequentially, or by a heat press with tool surfaces configured to press the desired pieces at the desired locations and not to press other locations of the band 920. The main body portion 950 may be cut to size at this point in the process, such as by cutting the ends 950 of the main body piece 950 to form angled edges, as seen in FIG. 40. A band closure trim strip 962 may be used to bond the ends of the main body piece 950 together to form the tubular body 921, as shown in FIG. 40. In one embodiment, the ends of the main body piece 950 are first wrapped to form the tubular body 921 and then stitched together along the seam, then the band closure trim strip 962 is applied to cover the stitching and secure the connection. The band closure trim strip 962 wraps around both the inner and outer surfaces 927, 928 of the band 920 when assembled, and one embodiment of the band closure strip can be seen in greater detail in FIG. 19. In one embodiment, the closure trim strip 962 is locally heat pressed subsequent to the additional heat pressing operation described above. After stitching and connection of the trim strip 962, the final structure of the band 920 is formed, with the pocket 940 defined on the inner surface 927.

Figure 8:
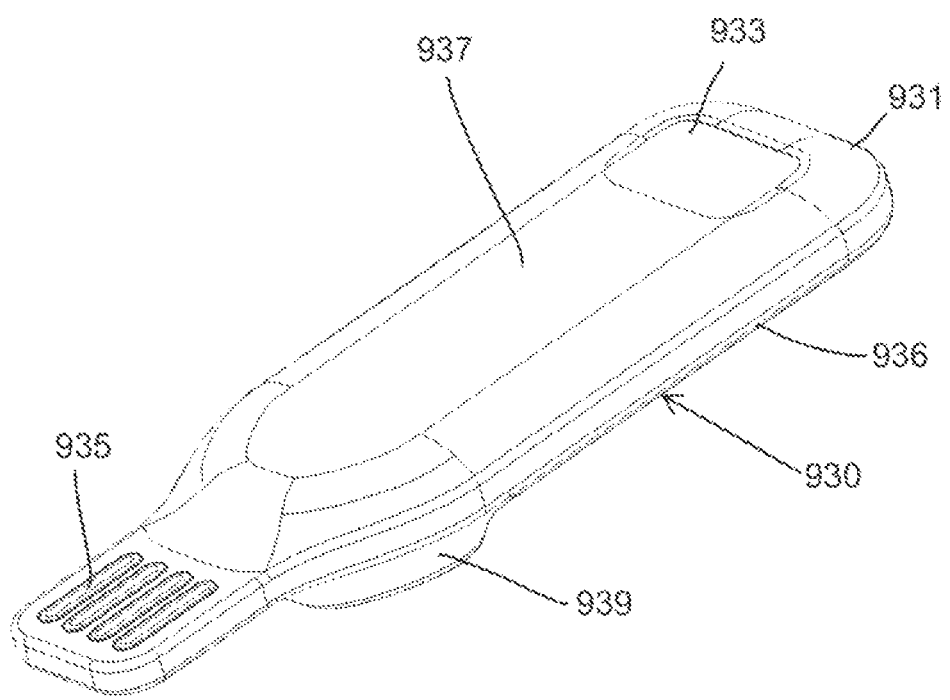
FIG. 8 is a top perspective view of another embodiment of a module according to aspects of the disclosure.
Figure 9:
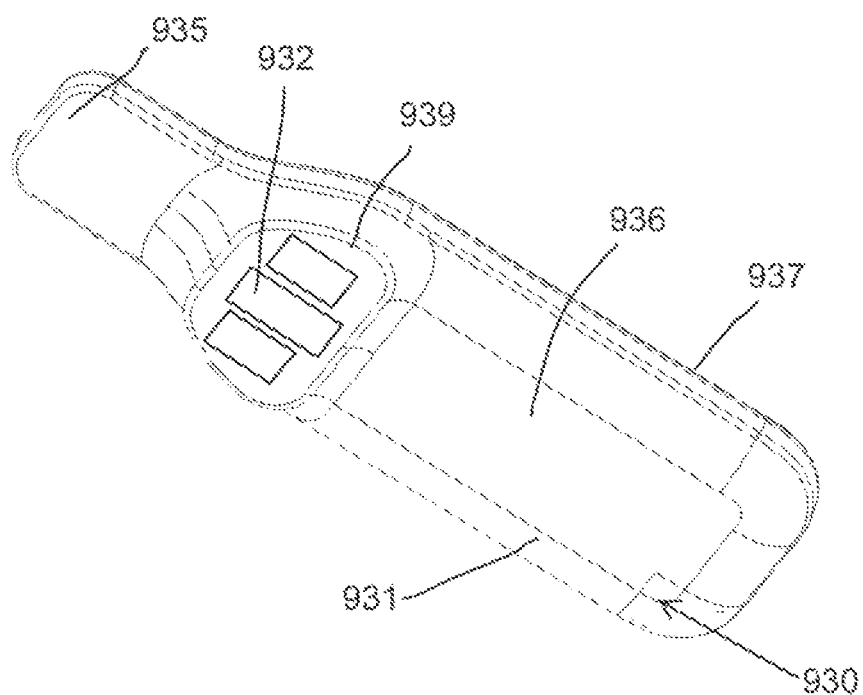
FIG. 9 is a bottom perspective view of the module of FIG. 7.
Figure 10:
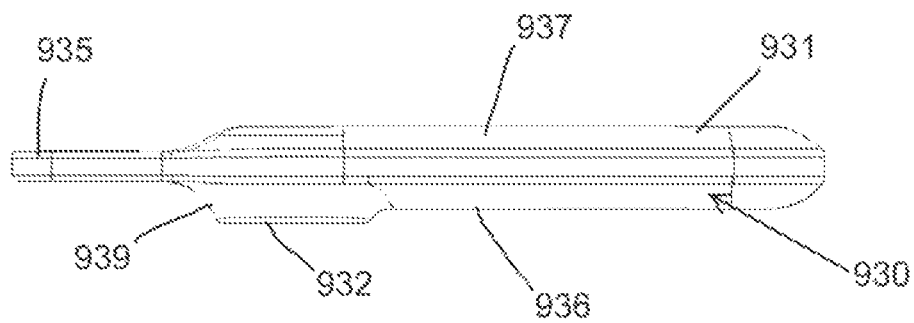
FIG. 10 is a side view of the module of FIG. 7.
Figure 11:
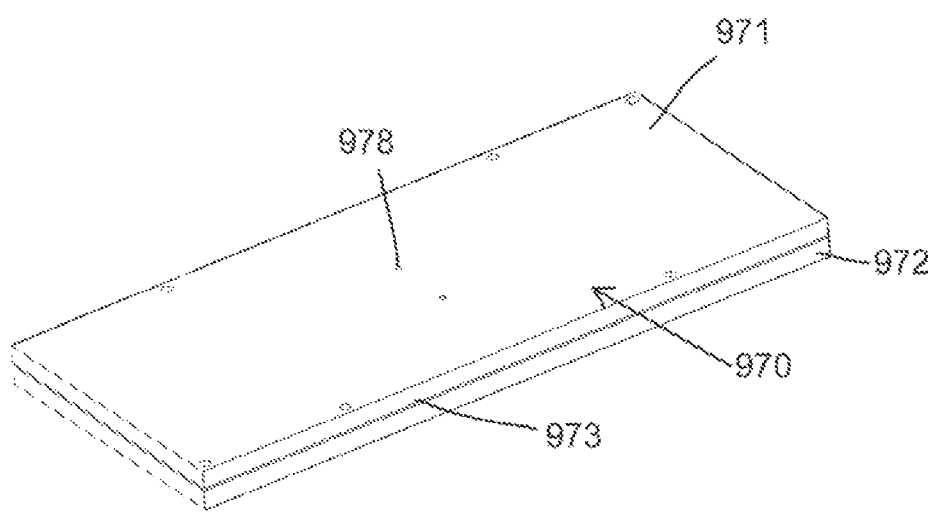
FIG. 11 is a perspective view of one embodiment of a mold for manufacturing a band according to aspects of the disclosure.

FIGS. 8-10 show an example of a module 930 that may be used in association with apparel or other devices, such as being insertable within an armband that may be used during intense physical activity. Module 930 may include one or more mechanical, electric, and/or electro-mechanical components, such as computer components, that are described elsewhere herein, as well as a casing 931 forming a structural configuration for the module 930. Module 930 may comprise at least one of a processor, a non-transitory computer-readable medium, sensor and/or a transceiver. One or more components may be similar to and/or identical to any component shown and described above in FIGS. 1-5. Those skilled in the art will appreciate that module 930 and the casing 931 may have multiple different structural configurations and the illustrations are merely exemplary.

In the embodiment of FIGS. 8-10, the module 930 has at least one sensor 932, which may be in the form of, for example, a heart rate sensor or other sensor for sensing another physiological parameter of the user. Module 930 may be configured to contact the skin of the user during wear while the module 930 is secured within the band or apparatus. For example, the heart rate sensor 932 in this illustrated embodiment is an optical sensor that works best in contact or close proximity with the skin. As shown in FIGS. 8-10, the casing 931 of module 930 has a projection 939 on the underside 936, and the sensor 932 is mounted on the end of the projection 939. The projection 939 extends the sensor 932 farther away from the surrounding surfaces of the casing 931, permitting greater capability for forming continuous contact with the user's body. Band 920 may have an aperture that allows a front surface of the protrusion to contact the user's skin, however, the remainder of underside 938 is held within the band 920 or at least is separated from the user's skin by at least one layer of a material. In one embodiment, the layer of material may be configured to wick away moisture (e.g., such as sweat) away from the sensing surface on the user's skin. In other embodiments, it may be configured to prevent moisture, light, and/or physical materials from contacting the sensing surface or location during the physical activity. In one embodiment, it may selectively block light of certain wavelengths. In certain embodiments, at least 95% of ambient light is blocked within the immediate vicinity of the sensing surface. In another embodiment, at least 99% of the ambient light is blocked. This may be advantageous for optical sensors, such as optical heart rate sensors. Those skilled in the art will appreciate that other sensors, including those sensors described above in relation to FIGS. 1-5, may be used—either alone in combination with each other or other sensors—without departing from the scope of this disclosure.

In one general embodiment, the module 930 may include one or more user input interfaces, such as for example, buttons 933 to provide user-actuated input. An example user input interface may consist of single mechanical button, e.g., button 933, which is shown on the top side 937 opposite the underside 936. Yet in other embodiments, display feature 934 may be configured as a user-input interface. Those skilled in the art will appreciate that one or more user-actuated inputs may also be received through one or more transceivers of the module 930. For example, a system may be configured such that a user may be able to enter a user input onto an electronic mobile device which may mimic using buttons 933 or, alternatively, perform different functions than available in a specific instance of actuating buttons 933. Module 933 may further comprise one or more display features 934.

In one embodiment, the pocket 940 of the band or apparatus may be configured to receive module 930 having a display feature 934 on surface that provides at least one visual indicia to a user. Display features 934 may be a simple light source, such as a light emitting diode. In a specific embodiment, the color, intensity, or pattern of illumination of at least one light source in display features may be used to provide a visual indication to the user. Those skilled in the art will further appreciate that more complex display devices, such as LED, OLED, LCD, etc. may be utilized. Other output mechanisms, such as audible and tactile are within the scope of this disclosure.

Module 930 may further include one or more connectors 935 for charging and/or connection to an external device. In one embodiment, connectors 935 may include a serial bus connection, such as that may comply with one or more Universal Serial Bus (USB) standards. In one embodiment, connectors 935 may be configured to provide at least of the same electronic information to an external device that may be transmitted via one or more transceivers of the module 930.

When the module 930 in the embodiment of FIGS. 8-10 is received within the pocket 940 illustrated in FIG. 6-7 or 15-19, connector 935 is received within the shell 948 (FIGS. 6-7) or the end of the housing 963 (FIGS. 15-19), the underside 936 of the casing 931 is positioned in contact with the inner wall 944 of the pocket 940, and the top side 937 of the casing 931 is positioned in contact with the outer wall 943 of the pocket 940. In this arrangement, the projection 939 extends through the sensor opening 945 to place the sensor 932 in closer proximity with the user's body, the button 933 is positioned adjacent the button portion 947 on the outer wall 943, and the light 934 is positioned in alignment with the window 946 to permit viewing of the light 934 through the outer wall 943. The projection 939 extending through the sensor opening 945 and also in certain embodiments may assist in holding the module 930 in place. In this configuration the end of the module 930 opposite the connector 935 protrudes slightly from the access opening 942, in order to facilitate gripping for removal of the module 930.

The casing 931 may have a structural configuration to increase comfort of wearing the module 930 in close proximity to the user's skin. For example, the casing 931 has a flat configuration to create a thin profile, making the module 930 less noticeable when being worn on the user's body. As another example, the casing 931 may have curved contours on the underside 936 and the top side 937, as well as curved or beveled edges, in order to enhance comfort. The casing 931 of the module 930 in the embodiment of FIGS. 8-10 has curved or beveled edges, in order to enhance comfort. It is understood that this module 930 may be utilized as described herein, and may have additional or alternate features as described herein. The housing 963 of the band 920 as illustrated in FIGS. 15-19 and 27-31 is configured to fit the module 930 illustrated in FIGS. 8-10.

In certain embodiments, computer-executable instructions may be used to calibrate a device or system, such as to account for the location, orientation, or configuration of a sensor or group of sensors. As one example, module 930 may include a heart rate sensor. The heart rate sensor may be configured such that when correctly orientated on or in the band, the heart rate sensor is located or oriented a certain way with respect to the user. For example, if the heart rate sensor is an optical heart rate sensor, it may be within a distance range to the skin (with respect to multiple axes and location). Further, one or more sensors may be configured such that when correctly oriented within the band (e.g., placed within the pocket, a contact of a sensor is configured to be in communication with the user (e.g., their skin or alternatively their clothing). Too much variance with respect to the orientation or location of the sensor may result in inaccurate and/or imprecise data. In certain embodiments, one or more sensor measurements, either raw or calculated, may be utilized to determine a proper or preferred orientation(s) or location(s) of the sensor(s).

FIGS. 48-57 illustrate embodiments for use with a band 920 that includes some or all of the features of the band 920 illustrated in FIGS. 15-19, and may be manufactured in a manner similar to the method illustrated in FIGS. 20-40. Thus, the features and manufacturing techniques of the band 920 of FIGS. 48-57 that are similar to those already described will not necessarily be described again for the sake of brevity. Similar components described already may be referred to using similar reference numbers.

Figure 57:
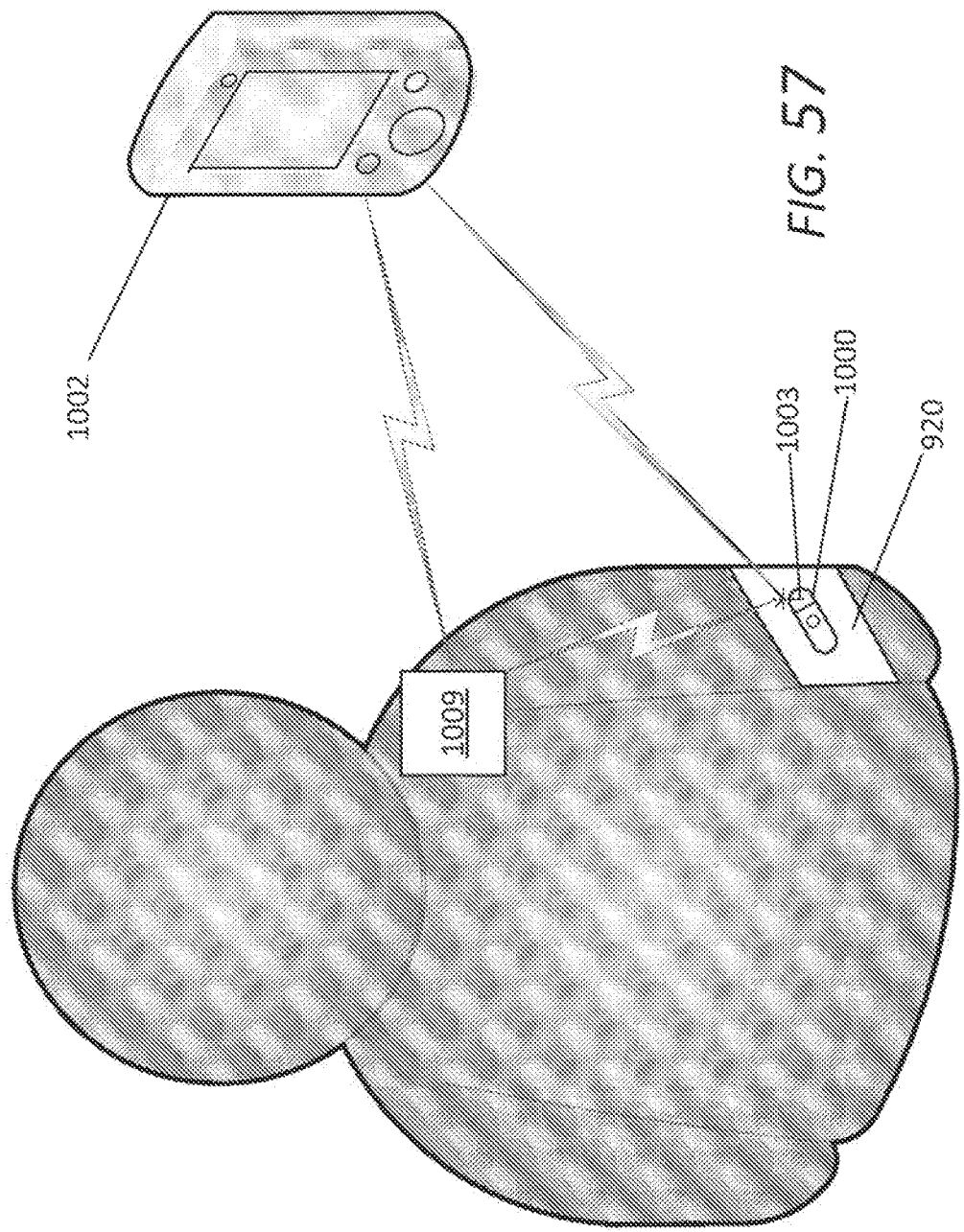
FIG. 57 is a schematic view illustrating another embodiment of a band with an additional input device connected to the band, with the band being worn on an arm of a user, and with the additional input device being in communication with one or more external devices.
Figure 58:
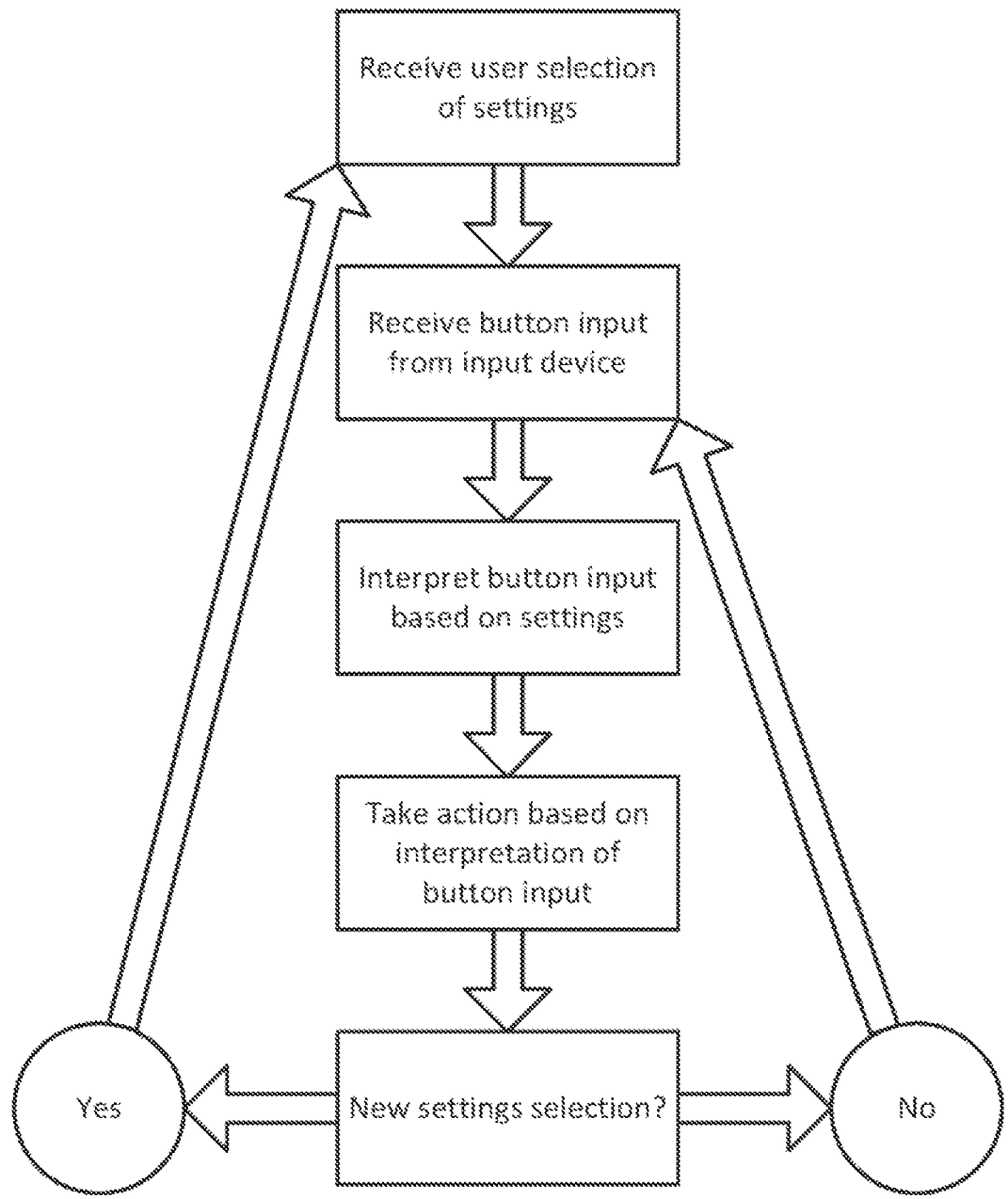
FIG. 58 is a flowchart showing one embodiment of a method of operation that can be used in connection with an external device and an additional input device according to aspects of the disclosure.
Figure 59:
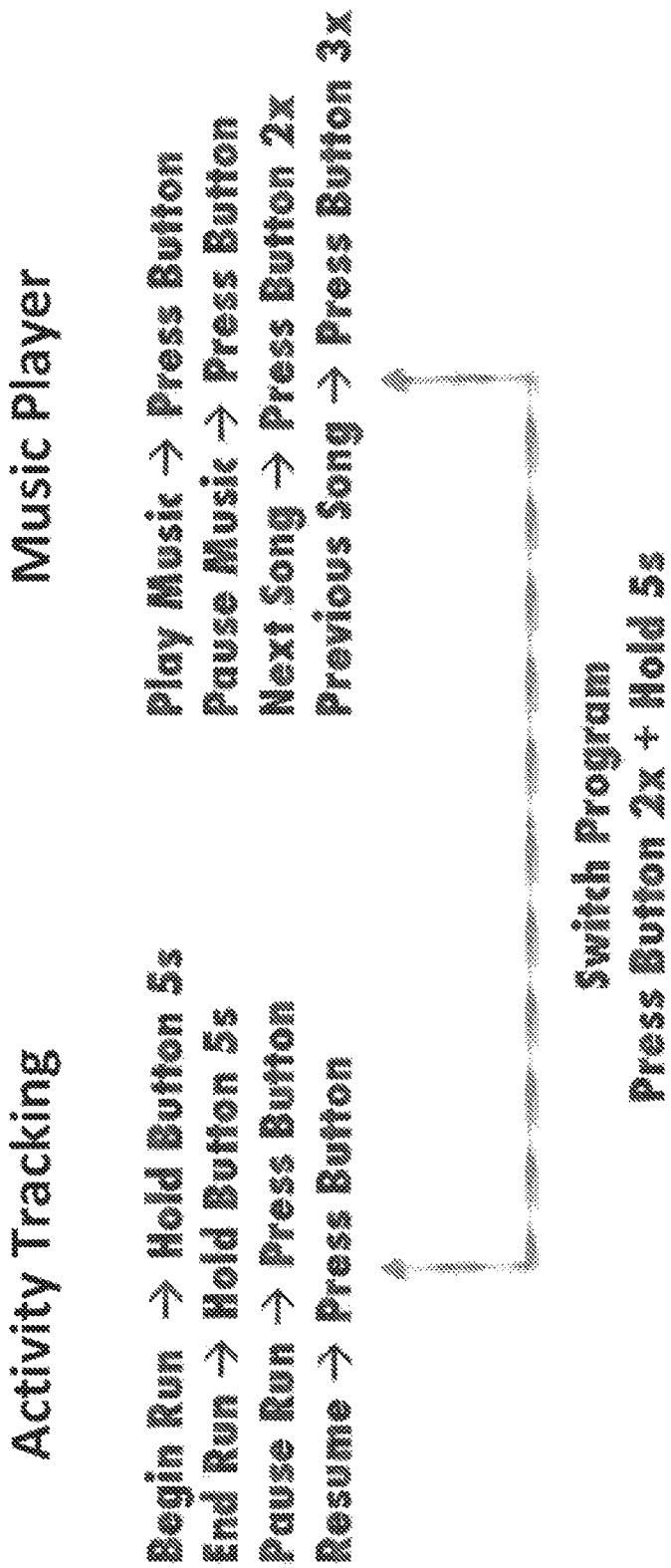
FIG. 59 is a flowchart showing another embodiment of a method of operation that can be used in connection with an external device and an additional input device according to aspects of the disclosure.
Figure 60:
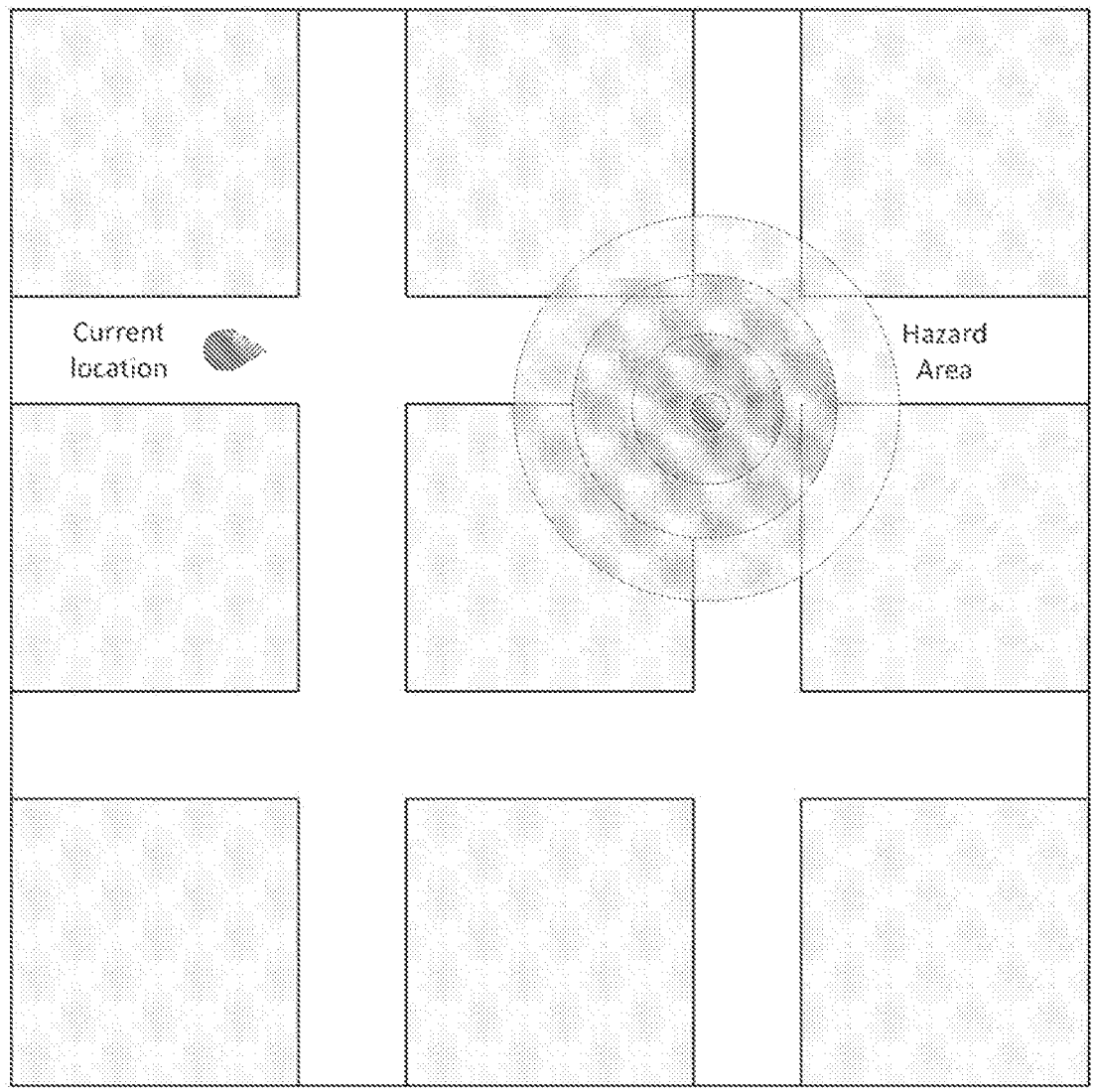
FIG. 60 illustrates one embodiment of a display of an external device being operated in conjunction with an additional input device according to aspects of the disclosure.
Figure 61:
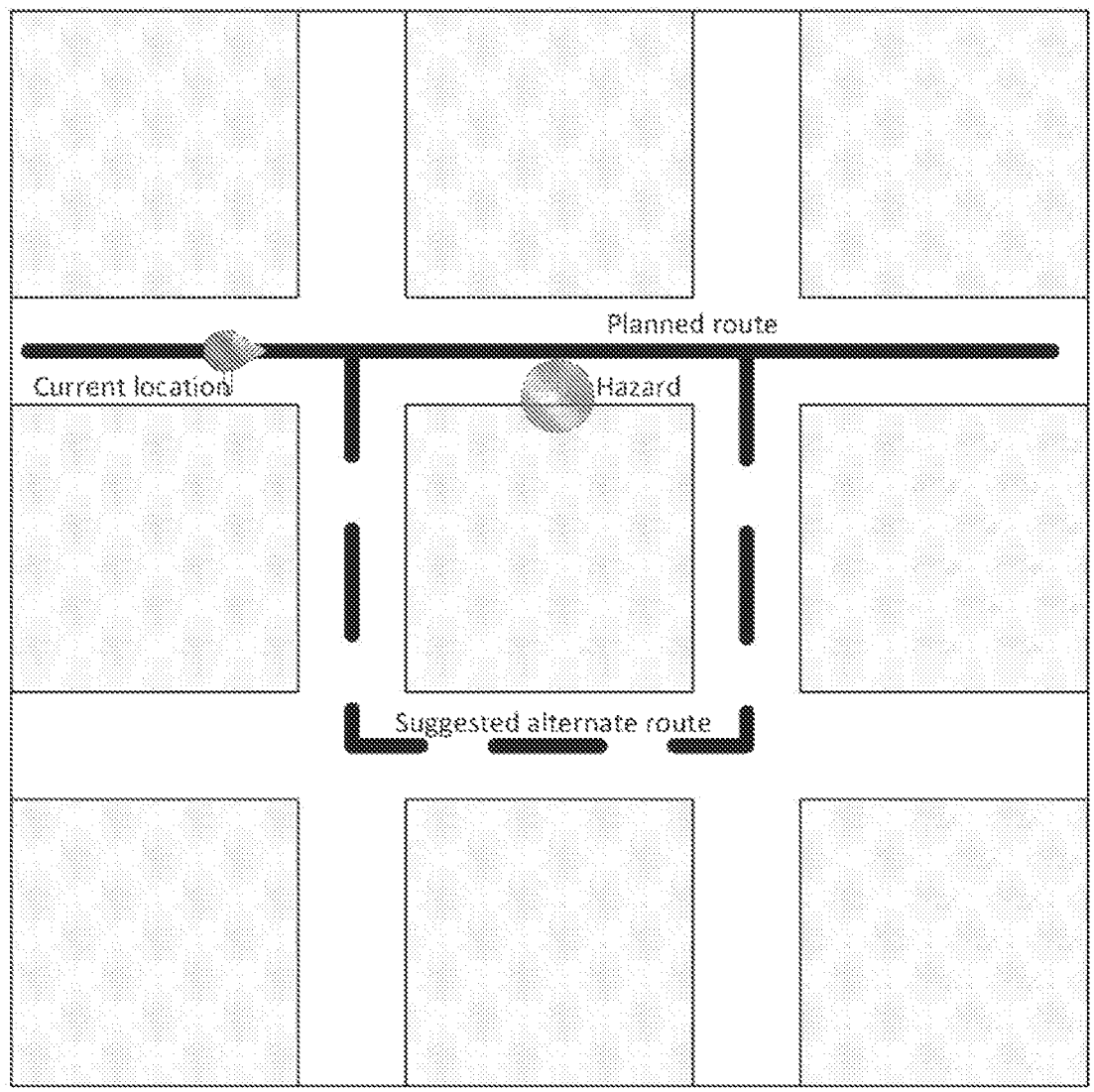
FIG. 61 illustrates another embodiment of a display of an external device being operated in conjunction with an additional input device according to aspects of the disclosure.
Figure 62:
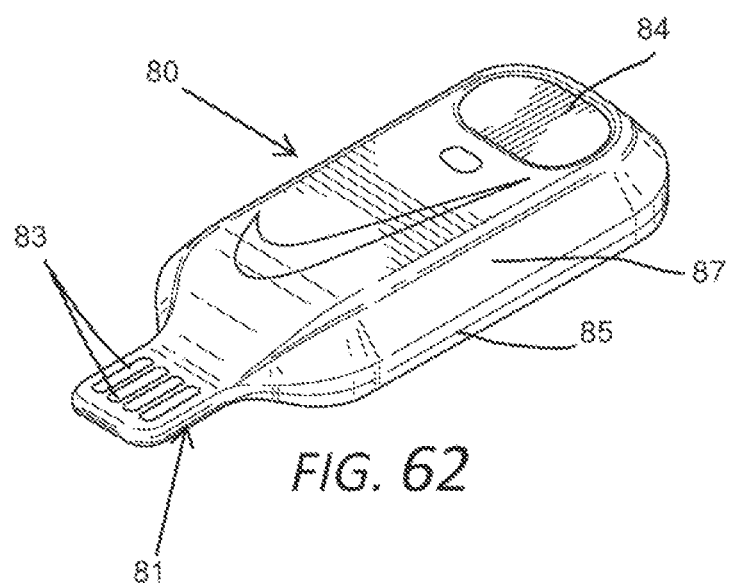
FIG. 62 is a top front perspective view of one embodiment of an electronic module according to aspects of the present disclosure.

In the embodiments of FIGS. 48-57, the band 920 includes a input device 1000 connected to the housing 963 and/or otherwise received within the pocket 940 and configured for connection to the module 930 when the module 930 is received within the pocket 940. The input device 1000 has one or more buttons 1001 thereon that are accessible from the outer surface 928 of the band 920, such as through the outer wall 943 of the band 920. The input device 1000 is configured for communication with an external device 1002, as shown in FIG. 57, and may have any of the components of the computer device 200 described above. In one embodiment, the input device 1000 includes a wireless transmitter 1003 (which may be part of a transceiver) configured for communication with the external device 1002, a port 1004 for connection to the connector 935 of the module 930, and potentially a small memory and/or processor for operation of the button(s) 1001, transmitter 1003, and port 1004. In one embodiment, the input device 1000 may include no internal operating system or significant software, and the input device 1000 may be configured to simply transmit a signal that the button 1001 was pressed, along with the sequence and/or length of the button press(es) 1001.

The button(s) 1001 of the input device 1000 may be one of a number of different types, including a tactile/mechanical button, a touchscreen, a heat-sensitive button, or other device capable of registering a touch by the user. It is understood that some types of buttons 1001 may require a window or other passage through the outer wall 943 of the band 920 for operation. In the embodiments of FIGS. 48-57, the input device 1000 includes tactile buttons 1001. The input device 1000 may include one or more additional buttons 1001, as illustrated in FIGS. 48-56 and described below. For example, each of the embodiments in FIGS. 48-55 has a main button 1001A and an optional additional volume control button 1001B. Various techniques and methods of operation of the button(s) 1001 are also described below. The band 920 may also have indicia 1008 on the outer surface 928 to inform the user where to press to activate the button(s) 1001, as shown in FIG. 55.

The transmitter 1003, which may be part of a transceiver as stated above, is configured for wireless communication with one or more external devices 1002, as illustrated in FIG. 57. It is understood that any of the embodiments of FIGS. 48-57 may have such a transmitter 1003. In one embodiment, the transmitter 1003 may be a Bluetooth or Bluetooth Low Energy (BTLE) transmitter. In other embodiments, the transmitter 1003 may use different transmissions, frequencies, protocols, etc., such as a Wi-Fi transmitter.

The port 1004 may include any connecting structure, and the configuration of the port 1004 may depend on the configuration of the module 930 to which it is connected. In the embodiment of FIGS. 48-57, the port 1004 is a USB or USB-compatible port configured to connect with the USB connector 935 on the module 930 of FIGS. 7-10. It is understood that the port 1004 may not include all of the hardware of a typical USB port in one embodiment, as the port 1004 may be configured only to draw power from the module 930 for operation of the input device 1000, and not to exchange data with the module 930. In another embodiment, the input device 1000 may be configured to operate as a wireless communications interface between the module 930 and the external device 1002, e.g., by receiving and/or transmitting data from/to the module 930 through the port 1004 and receiving and/or transmitting data from/to the external device 1002 through the transmitter 1003.

The input device 1000 may further include haptic feedback features, such as a vibration motor or other haptic feedback mechanism 1009 (shown schematically in FIG. 52), to communicate various signals (e.g., alerts) to the user. The input device 1000 may be configured for providing different types of haptic feedbacks, such as a steady vibration, pulsed vibration, etc. The input device 1000 may receive signals from the external device 1002 to generate specific haptic feedback. In one embodiment, the resolution of when to generate haptic feedback and which haptic feedback to generate is performed by the external device 1002, such that the input device needs only to receive the signal and generate the haptic feedback. The external device 1002 may utilize user settings for providing specific haptic feedback in the event of a specific occurrence, e.g., an incoming phone call, an emergency alert, an activity milestone reached, or other event. Haptic feedback may be used in connection with the various applications and functions described below.

Figure 48:
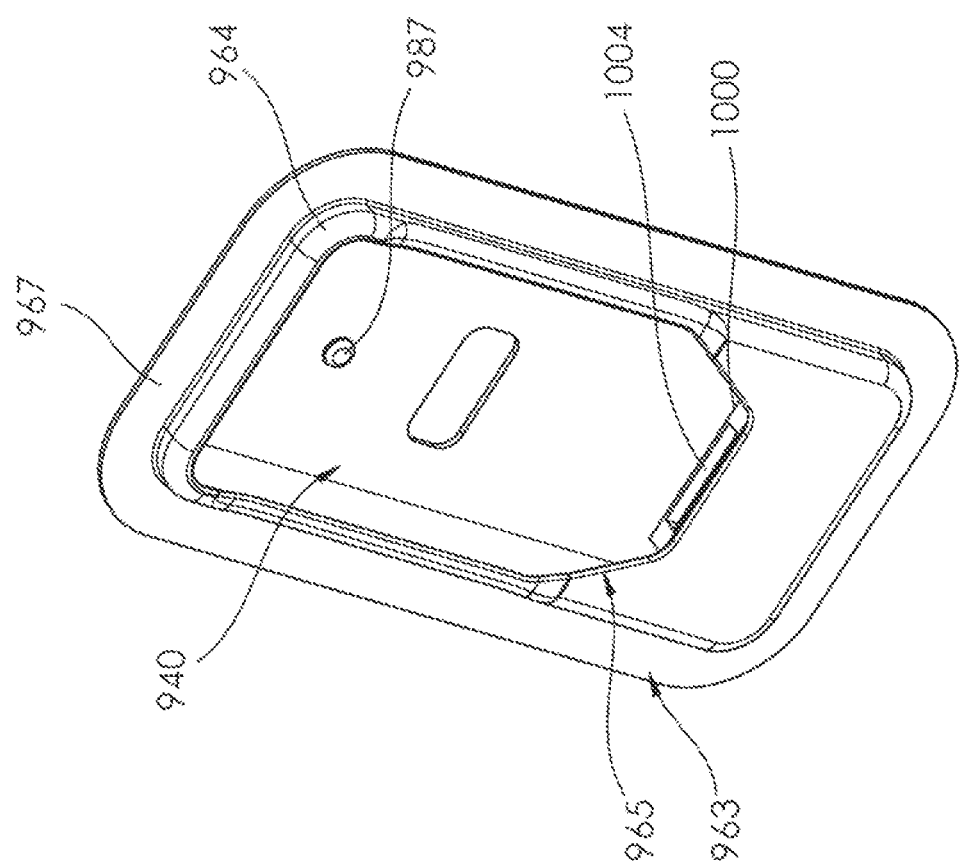
FIG. 48 is a bottom perspective view of one embodiment of a housing and additional input device that is usable in connection with a band and module according to aspects of the disclosure.
Figure 49:
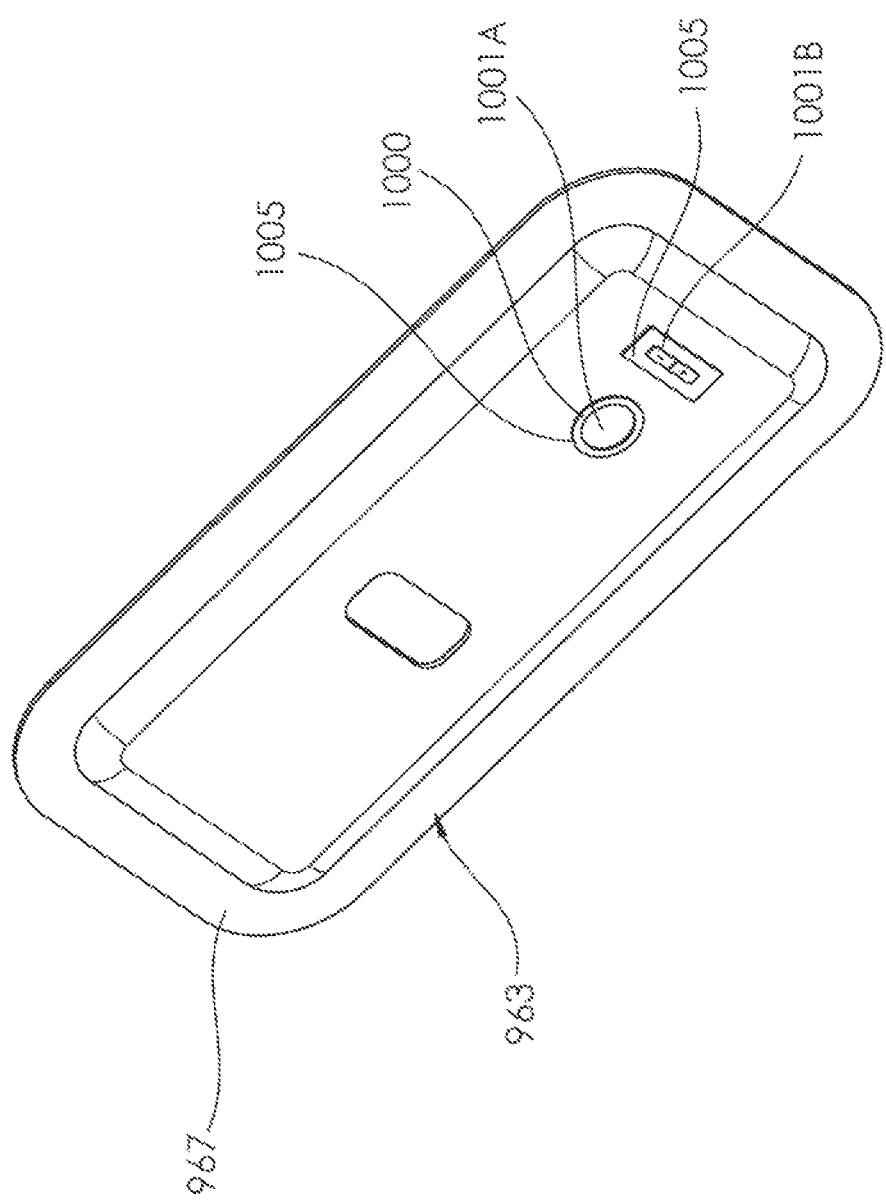
FIG. 49 is a top perspective view of the housing and additional input device of FIG. 48.

The input device 1000 may be positioned within the pocket 940 and/or the housing 963, may be positioned adjacent the pocket 940 and/or the housing 963, may form a part of the pocket 940 and/or the housing 963, or may be a separate element connected to the module 930, in various embodiments. In the embodiment of FIGS. 48-49, the input device 1000 is a separate device that is permanently or removably connected within the housing 963. The input device 1000 in this embodiment is in the form of a casing positioned within the end of the housing 963, proximate the narrowed portion 965 of the opening 942 (i.e., where the connector 935 of the module 930 is received), with the port 1004 having an opening facing into the pocket 940 defined by the housing 963. In this position, the module 930 can be inserted into the housing 963 so that the connector 935 is received within the port 1004, as shown schematically in FIG. 53. The input device 1000 may be permanently connected within the housing 963, such as by adhesive or other bonding technique, fasteners, integral forming, or other techniques, in one embodiment.

The input device 1000 may be removably connected within the housing 963 in another embodiment. Such a removable input device 1000 may be removed from the housing for connection or disconnection with the module 930, as shown in FIGS. 53-56 and described below. Alternately, such a removable input device 1000 may be retained within the housing 963 as the module 930 is connected and disconnected, such as by a releasable retaining structure on the input device 1000 and/or the housing 963, a high-friction fit that is sufficient to retain the input device 1000 in place during activity or removing the module 930 from the port 1004, or other removable configuration. The housing 963 may also have features to facilitate access to the buttons 1001. For example, as shown in FIG. 49, the housing 963 has one or more openings 1005 on the outer wall 943 to permit access to the button(s) 1001. In another embodiment, the housing 963 may have one or more protrusions on the inner surface of the outer wall 943 adjacent to the button(s) 1001, so that force exerted on the housing 963 can reliably activate the button(s) 1001, similar to the protrusion 987 described above.

Figure 50:
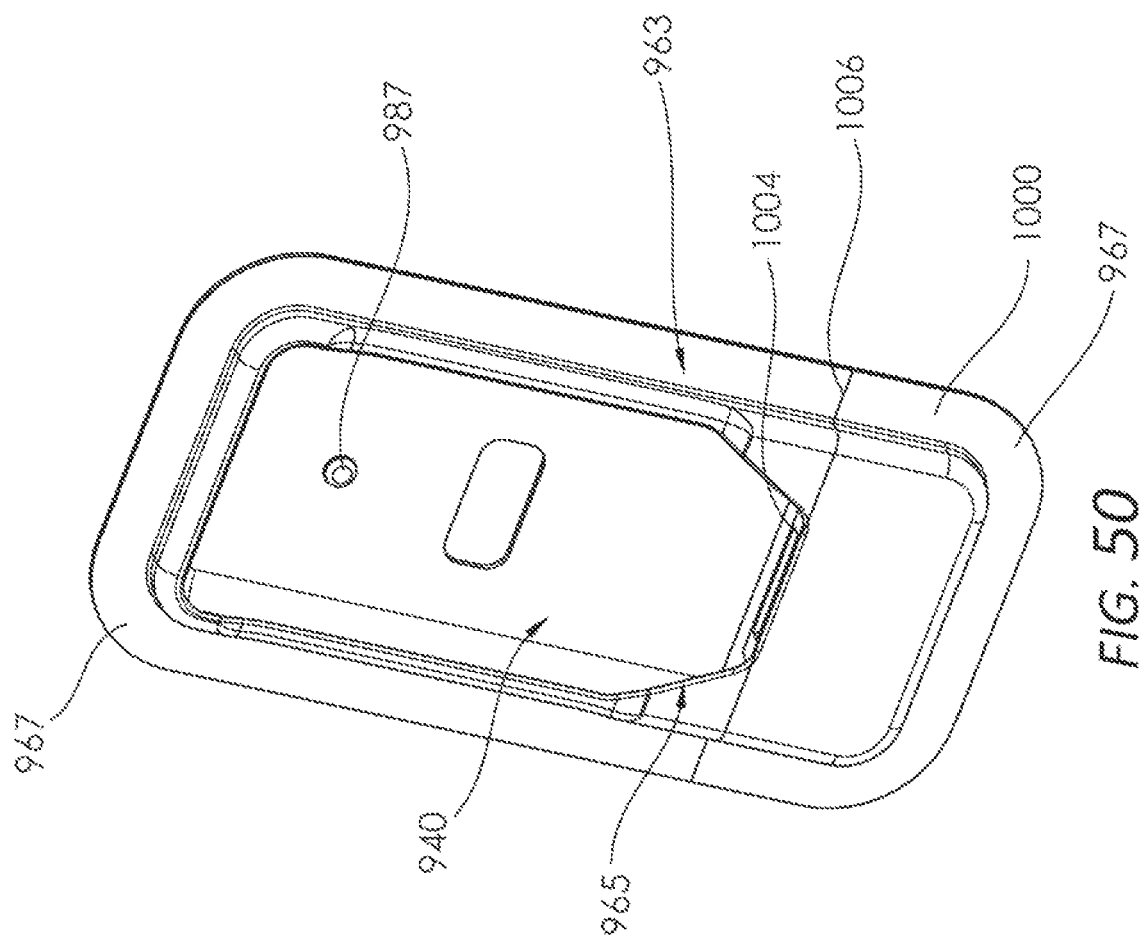
FIG. 50 is a bottom perspective view of one embodiment of a housing and additional input device that is usable in connection with a band and module according to aspects of the disclosure.
Figure 51:
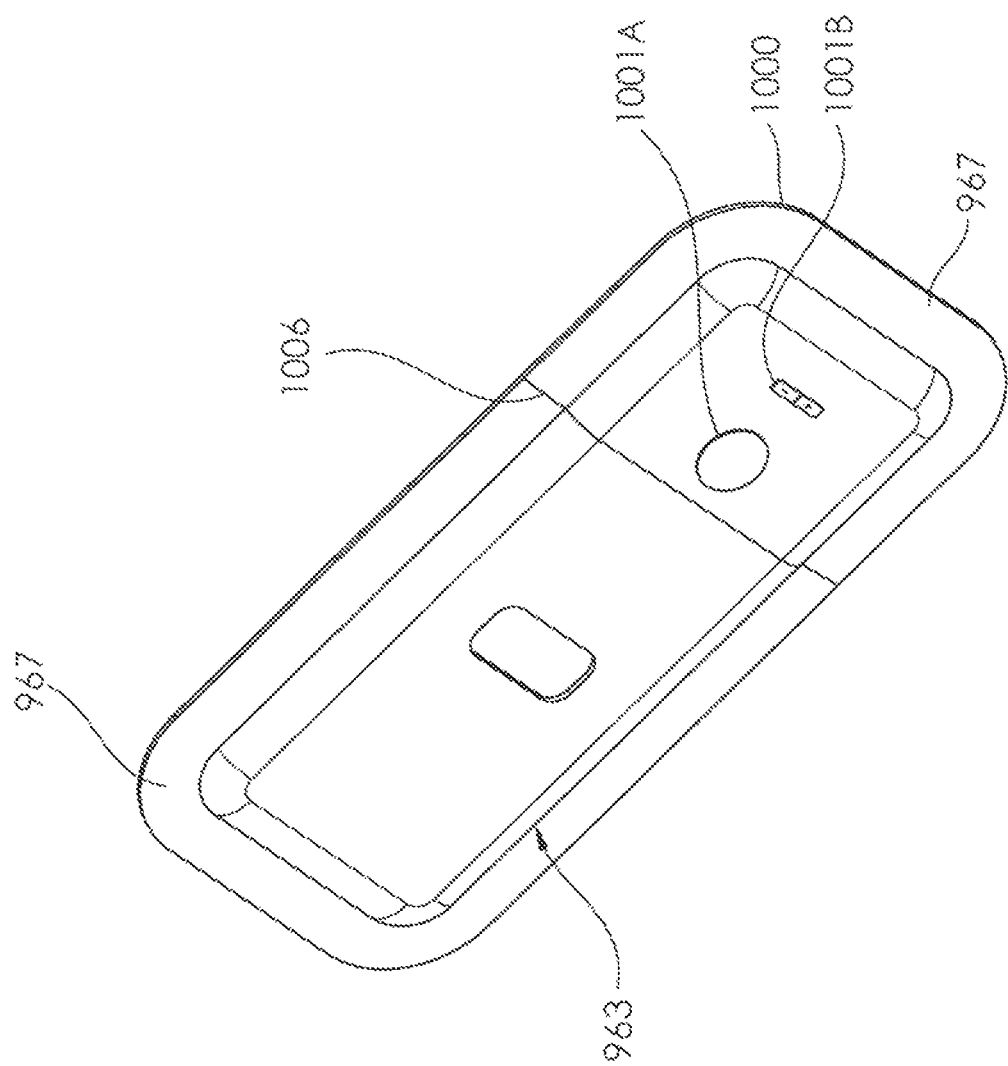
FIG. 51 is a top perspective view of the housing and additional input device of FIG. 50.
Figure 52:
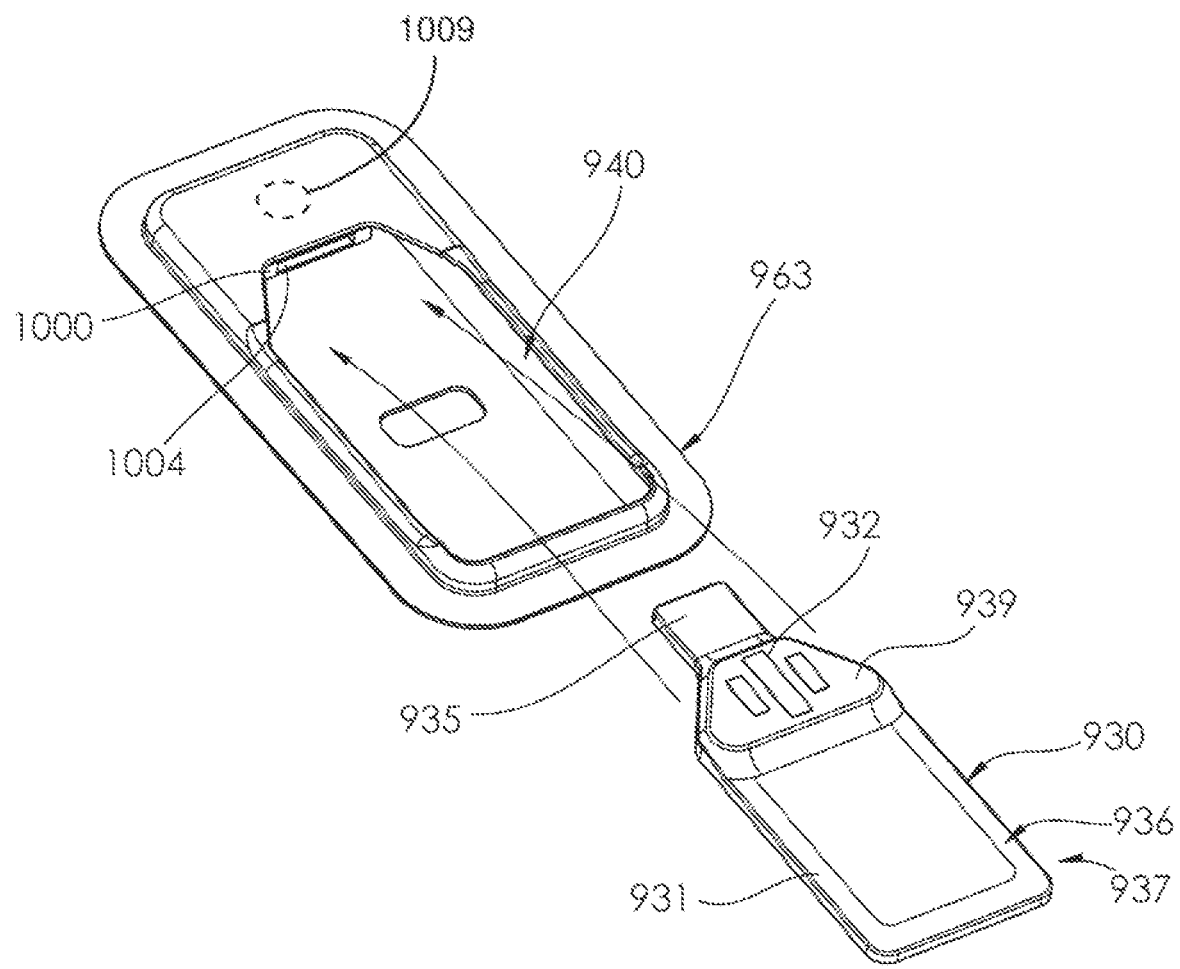
FIG. 52 is a bottom perspective view of the housing of FIG. 48 and the module of FIG. 7 being inserted into the housing.

In the embodiment of FIGS. 50-51, the input device 1000 forms a part of the housing 963 or forms part of a unitary structure with the housing 963. The input device 1000 in this embodiment forms an end of the housing 963 proximate the narrowed portion 965 of the opening 942, and has an outer shape and contour that are substantially contiguous with those of the housing 963. As shown in FIGS. 50-51, the input device 1000 has a flange 967 that is continuous with the flange 967 of the housing 963. The input device 1000 joins with the housing 963, and the housing 963 has an open end 1006 adjacent the input device 1000 in communication with the pocket 940, such that the port 1004 of the input device 1000 is placed in communication with the pocket 940 defined by the housing 963. In this configuration, the connector 935 of the module 930 is received within the port 1004 when the module 930 is inserted into the housing 963, as shown schematically in FIG. 52. The input device 1000 may be permanently connected within the housing 963 in one embodiment, or may be removably connected within the housing 963 in another embodiment, for example, by using one of the permanent or removable connection techniques described elsewhere herein. In this embodiment, the button(s) 1001 may be positioned on the outer surface of the input device 1000, as shown in FIG. 51.

Figure 53:
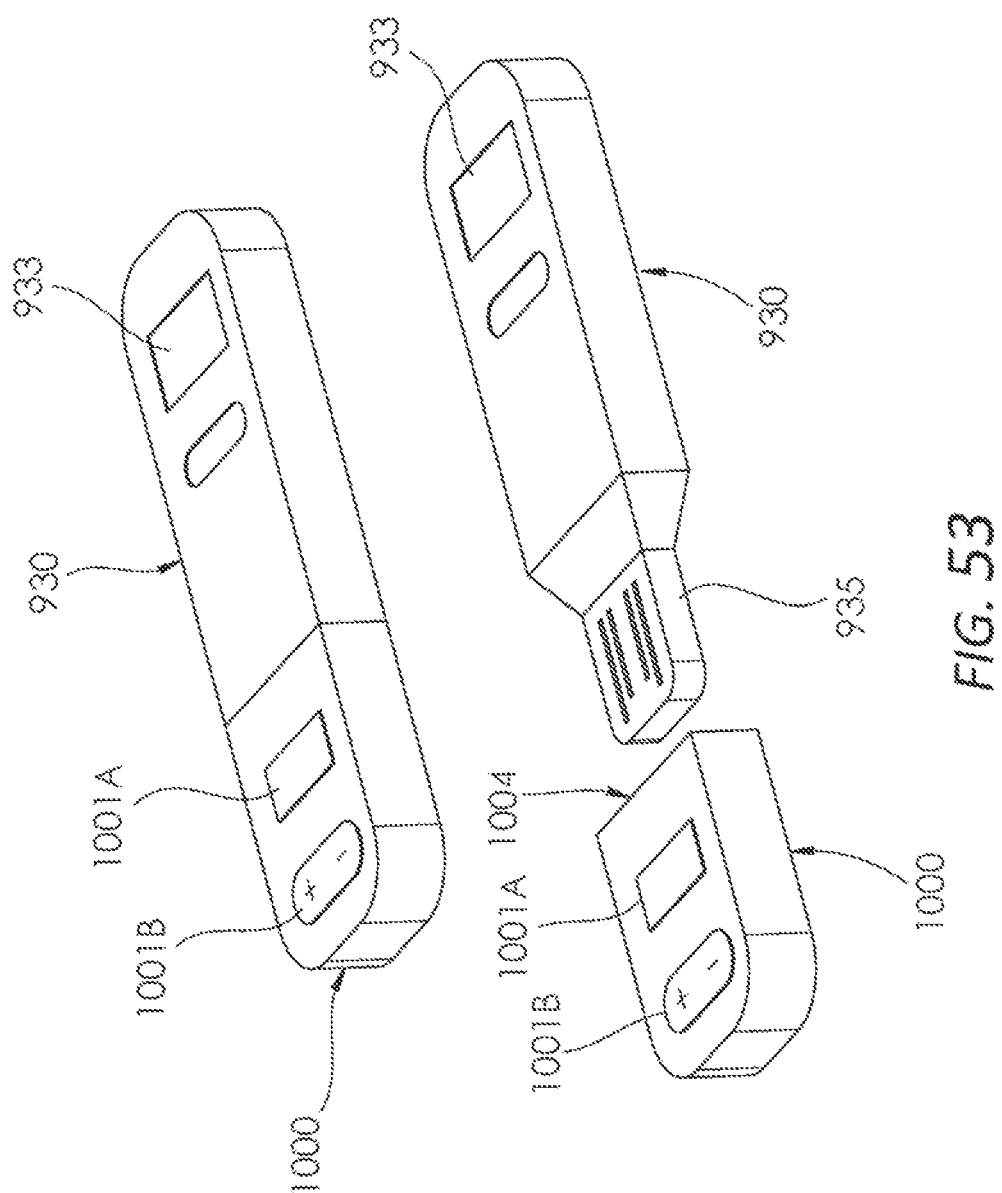
FIG. 53 is a perspective view and an exploded perspective view of another embodiment of an additional input device and a module according to aspects of the disclosure, showing a connection between the additional input device and the module.
Figure 54:
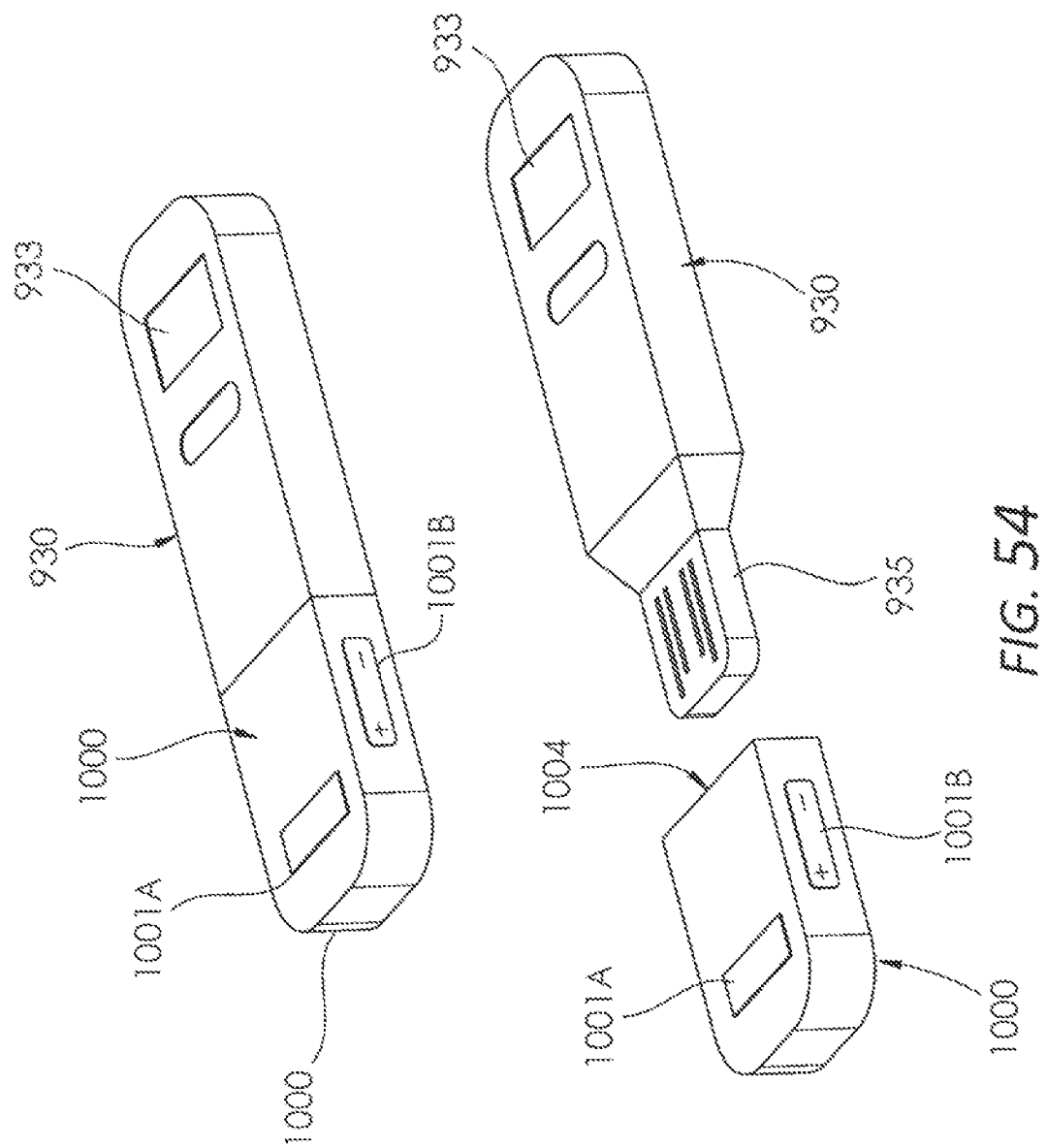
FIG. 54 is a perspective view and an exploded perspective view of another embodiment of an additional input device and a module according to aspects of the disclosure, showing a connection between the additional input device and the module.
Figure 55:
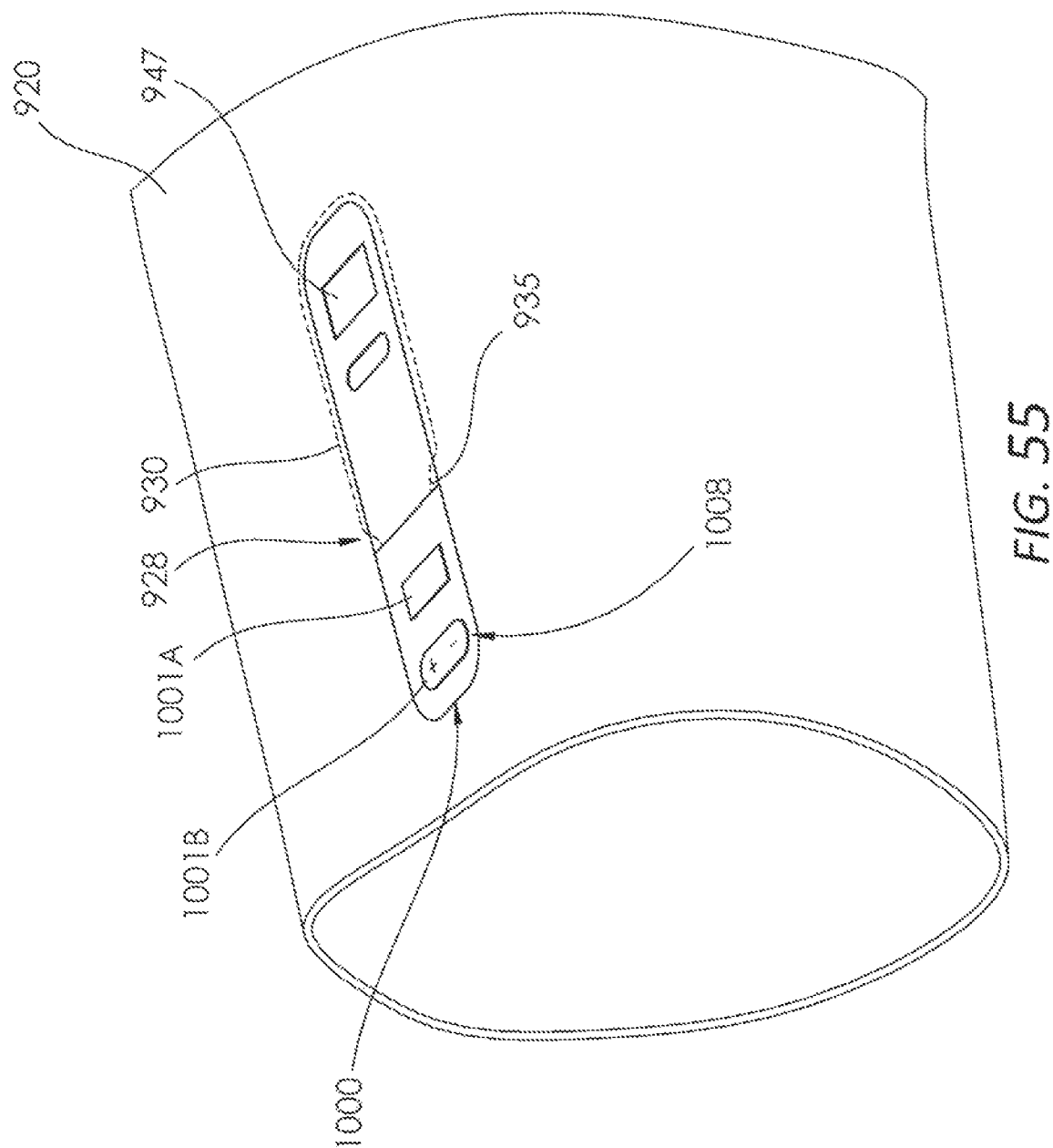
FIG. 55 is a perspective view of one embodiment of a band having an additional input device connected to the band, according to aspects of the disclosure.
Figure 56:
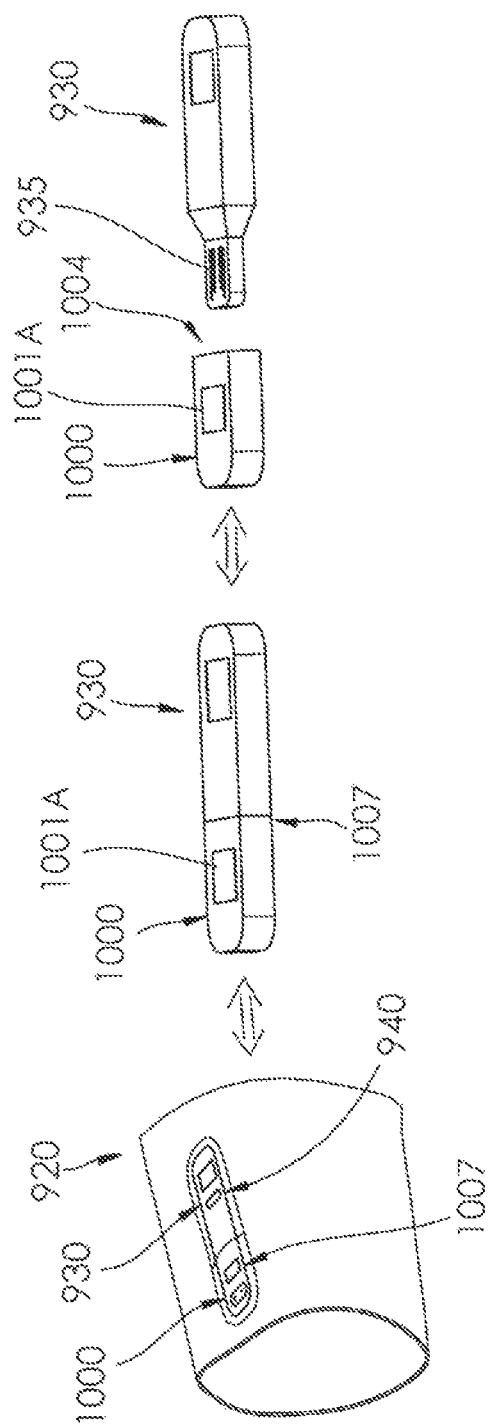
FIG. 56 is a schematic perspective view of another embodiment of a module, an additional input device, and a band according to aspects of the disclosure, showing the module being connected to the additional input device and then being connected to the band.

In the embodiments of FIGS. 53-54, the input device 1000 is a separate device that is configured for insertion into and removal from the housing 963 and the pocket 940 along with the module 930. The input device 1000 in each of these embodiments is in the form of a casing that is connected to the module 930 by inserting the connector 935 of the module 930 into the port 1004 outside the housing 963, and then inserting the module 930 and the input device 1000 simultaneously into the housing 963. Once inserted, the input device 1000 is positioned within the end of the housing 963, proximate the narrowed portion 965 of the opening 942, similar to the position shown in FIG. 48. Connection of the module 930 to the input device 1000 to form a connected structure 1007 and insertion of the connected structure 1007 into the pocket 940 defined by the housing 963 is shown schematically in FIG. 56. The input device 1000 of FIG. 53 differs from the input device 1000 of FIG. 54 primarily in the location of the volume control button 1001B, which is located on the top surface of the input device 1000 in the embodiment of FIG. 53 and is located on the side surface of the input device 1000 in the embodiment of FIG. 54. It is understood that the housing 963 and/or the band 920 may be configured for use with either of the input devices 1000 of FIGS. 53-54, such as by effective location of features for operating the button(s) 1001, including openings 1005, protrusions 987, indicia 1008, etc.

The input devices 1000 in FIGS. 48-56 are shown and described as being usable in connection with a band 920 as illustrated in FIGS. 15-19 and manufactured as illustrated in FIGS. 20-40. In other embodiments, the various embodiments of input devices 1000 described herein may be utilized with other embodiments of bands 920 as described herein, for example, the bands 920 shown in FIGS. 6-7 and manufactured as described herein. It is understood that the input device 1000 and/or the band 920 may be modified to provide suitable functionality for such a combination.

As described above, the input device 1000 is configured for communication with an external device 1002 through the transmitter 1003, as shown in FIG. 57. The external device 1002 may include any components of the computer device 200 described above, and may be a mobile phone or other mobile device that can be carried by or positioned near a user during physical activity. As also described above, the input device 1000 may be configured to transmit signals to the external device with button input indicating the activation of the button(s) 1001, which includes the sequence and/or length of the button press(es) 1001. The external device 1002 may include software configured to receive the button input as input and take further action based on the button input. For example, the software on the external device 1002 may interpret specific sequences of button 1001 presses (e.g., a single, double, or triple-tap) as different input signals, and/or may interpret long-hold button 1001 presses as different from button taps. Further, the external device 1002 can be programmed to interpret and use the button input as different inputs for different purposes, and the device 1002 may include various preprogrammed and/or user-selected settings governing the interpretation of the button input. The external device 1002 may include various applications and functionality that are controlled and/or influenced by the button input, according to the settings.

The input device 1000 may be in communication with multiple external devices 1002, either simultaneously or alternatively, and the module 930 may be in communication with the input device 1000 and/or the external device 1002. The input device 1000 and/or the external device 1002 may also be in communication with an external camera 1008, such as a body-mounted camera that may be capable of video and/or still photo capture. The input device 1000 and/or the external device 1002 may also be in communication with one or more assemblies such as the assemblies 400, 304 shown in FIGS. 4-5 and described herein, for collection and/or communication of additional data. It is understood that the external device 1002 may receive button input from a different type of input device, for example, the module 930, an assembly 400 as shown in FIG. 4 or other wearable assembly (e.g., a smart watch), and that the methods, functions, and operation of the external device 1002 as described herein are not limited to use with an input device 1000 according to the embodiments described herein. Examples of functions and applications that may be operated by the external device 1002 without input from the input device 1000 or any other input device include (without limitation): storing or deleting information; sending a signal to one or more other devices; initiating, answering, or ending a phone call; sending a text, picture, or video message; posting information to a website, social media outlet, blog, RSS feed, etc.; sharing information with a specified group of people and/or other devices; transmitting a location signal; controlling music and/or video being played by the external device 1002; controlling a camera associated with the external device 1002, including an integral camera of the external device 1002 or an external camera; interacting with the module 930; transmitting data received from the module 930; powering the external device 1002 and/or the input device 1000 on or off; as well as other functions. The functioning of the input device 1000 relative to the external device 1002 may be governed by settings on the external device 1002. Still further, it is understood that some processing of information performed by the external device 1002 may include sending the information to another device (e.g., a server) for processing and receiving further information from the other device.

Figure 78:
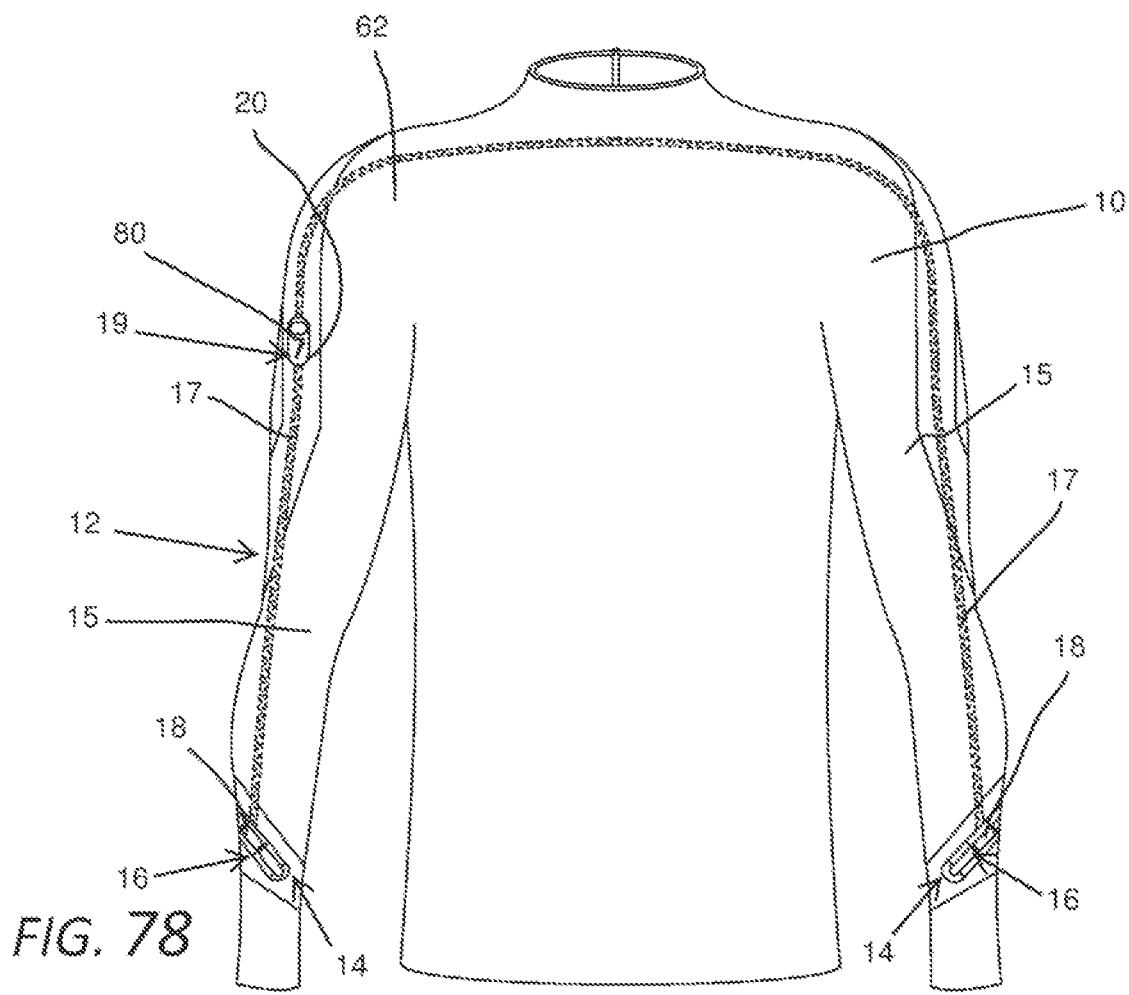
FIG. 78 is a rear view of one embodiment of a wearable article in the form of a shirt or jacket having a housing assembly connected thereto, according to aspects of the present disclosure, showing an exterior of the article.
Figure 79:
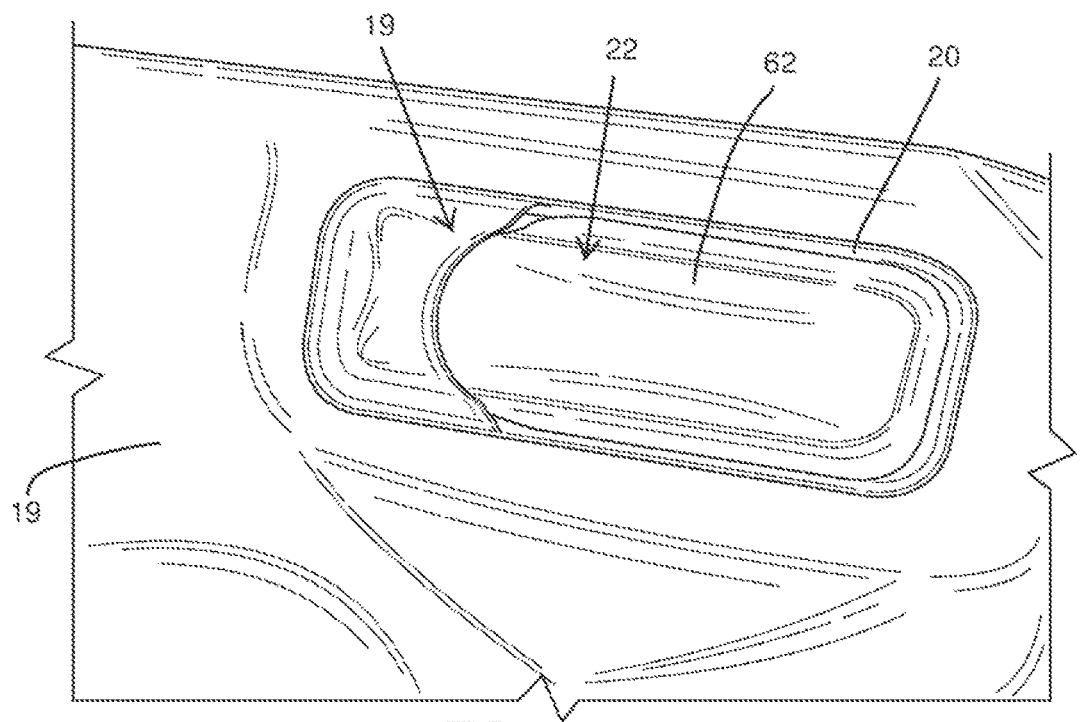
FIG. 79 is a plan view of the housing assembly and a portion of the exterior of the wearable article of FIG. 78.
Figure 80:
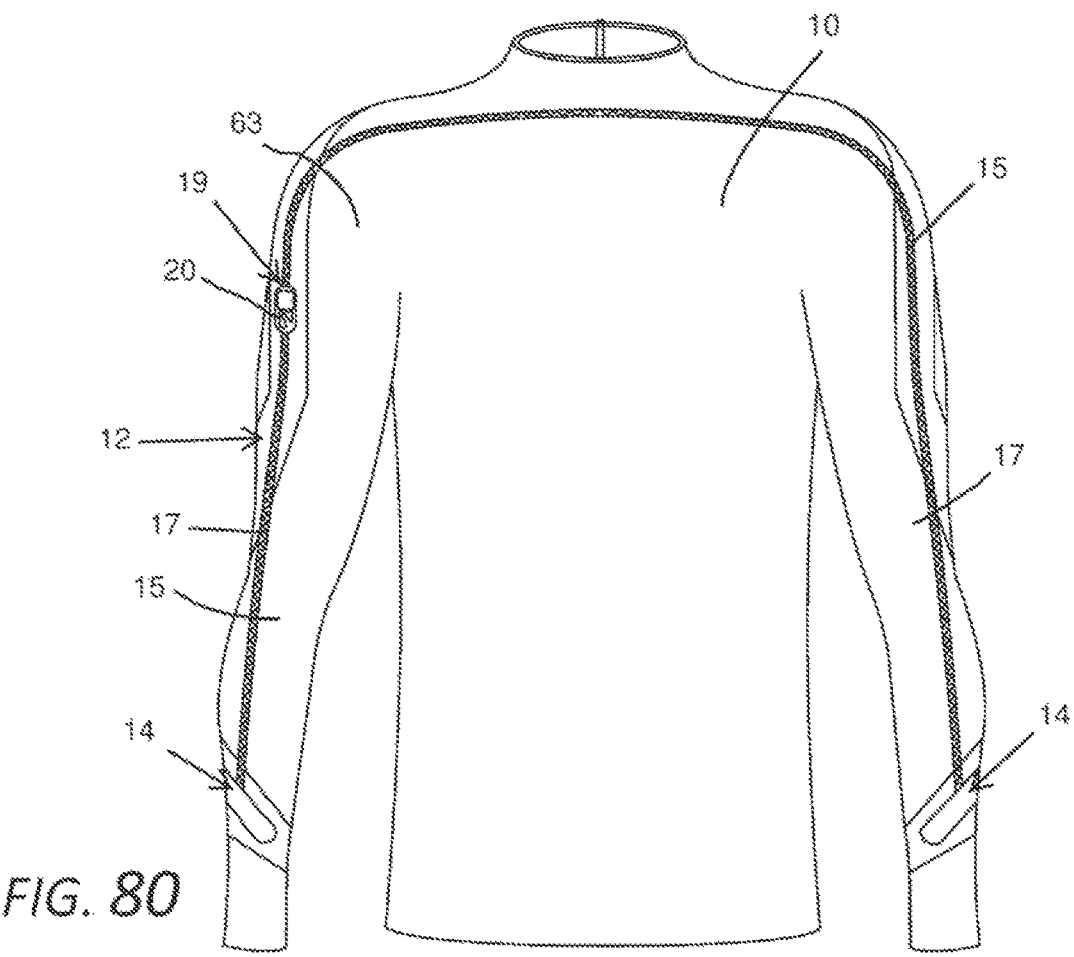
FIG. 80 is a rear view of the wearable article and the housing assembly of FIG. 78, shown inside out to illustrate an interior of the article.

In other embodiments, aspects of the structures and methods described herein may be used and/or adapted in connection with articles of apparel or other wearable articles beyond a band as described herein. For example, as illustrated in FIGS. 78-80, a housing 20 may be connected to an article of apparel 10 in the form of a shirt or jacket. The housing 20 is configured to engage an electronic module 80 that may include at least some of the aspects of the module 930 described herein, and which may be configured to achieve any functionality described above and to operate within the various network environments described above. In one embodiment, the article of apparel 10 includes one or more electrically-powered components 14, and the functionality of the electronic module 80 includes powering the electrically-powered component(s) 14. The housing 20 and/or the article of apparel 10 in this embodiment include various connection structures to establish an electrical connection between the housing 20 and the electrically-powered component(s) 14 to allow the module 80 to power the component(s) 14 when engaged with the housing 20.

An example of an article of apparel 10 is shown in FIGS. 78-80 in the form of an upper body garment (e.g., a shirt or jacket) having the housing 20 mounted on the article 10 and positioned in the shoulder region. It is understood that the housing 20 and other aspects described herein may be used with any article of apparel 10, including traditional articles of apparel such as shirts, pants, bodysuits, outerwear, footwear, hats, gloves, belts, etc., or specialized articles of apparel that are designed specifically to support the housing 20, such as armbands, waistbands, harnesses, or other wearable articles. In one embodiment, the article 10 has at least one electrically-powered component 14 connected thereto. The article 10 illustrated in FIGS. 78-80 includes an electrically-powered component 14 in the form of one or more arrays 16 of light emitting devices 18, e.g., light-emitting diodes (LEDs) or other devices. The article 10 has arrays 16 located on the forearm area of each arm portion 15 in FIGS. 78-80. A pair of conductive leads 17 (e.g., +/− or power/ground) are connected to each array 16 and are configured to supply power to all of the light emitting devices 18 of the array 16. The leads 17 in the embodiment of FIGS. 78-80 are configured in a wave or zig-zag pattern and are mounted on an elastically deformable material. This configuration permits stretching and flexing of the leads 17 without damage, which is advantageous when the leads 17 extend across an area of the article 10 that moves or flexes during use. The leads 17 extend to a power source for powering the array 16 or other electrically-powered component 14, and in the embodiment of FIGS. 78-80, the leads 17 extend to the housing 20 to permit the module 80 to serve as the power supply. It is understood that the article of apparel 10 may be considered to be part of an assembly including the article 10 as well as the component 14, the housing 20, and other features.

One example embodiment of the housing 20 is illustrated in FIGS. 63-75. The housing 20 is formed separately from the article 10 and is connected to the article 10, such as by bonding, mechanical connections, or combinations thereof. The housing 20 is configured for engaging and retaining the module 80 and may be provided as part of a housing assembly 19 that includes the housing 20 along with electrical connecting structure 30 that forms an interface 31 configured for electronic connection to the module 80 when the module 80 is engaged with the housing 20. In the embodiment of FIGS. 63-75, the housing 20 comprises a receptacle 21 that defines a chamber 22 configured for receiving the module 80, but the housing 20 may engage and retain the module 80 using a different structure in another embodiment. The housing 20 may be made of a thermoplastic polyurethane (TPU) material and formed by injection molding in one embodiment, but may be partially or completely made from other materials and/or other techniques in other embodiments. In one embodiment, the receptacle 21 is formed of a single piece by injection molding. The receptacle 21 in this embodiment is a moderately rigid shell that has walls 23 defining the chamber 22 and also has an access opening 24 providing access to the chamber 22. In one embodiment, the rigidity of the receptacle 21 may be sufficient to protect the module 80. The rigidity of the material forming the receptacle 21 may be greater than the rigidity of the material forming the article 10. As shown in FIGS. 63-66, the receptacle 21 in the illustrated embodiment has a lip 25 that extends inwardly around at least a portion of the access opening 24 and functions to retain the module 80 within the chamber 22. The walls 23 of the receptacle 21 are configured to enclose and hold a portion of the module 80 (e.g., a connector 81), as described in greater detail herein. In the embodiment of FIGS. 63-66, a one of the walls 23 extends over the top side 27 of the receptacle 21 to form this enclosure, such that the wall 23 and the lip 25 define the access opening 24 on the top side 27.

In one embodiment, the housing 20 further has a flange 26 that extends outwardly around at least a portion of the periphery of the receptacle 21 and is configured for connection to the article 10. In the embodiment shown in FIGS. 63-75, the flange 26 extends generally in a single plane around the entire periphery of the receptacle 21. In other embodiments, the flange 26 may have a different configuration (e.g., intermittent), or may not be present. Generally, the exterior surfaces of the housing 20 shown in FIGS. 63-75 are smoothly contoured, both for aesthetics and for increased comfort when the housing 20 engages the user's body. The housing 20 also has a bottom side 28 opposite the top side 27. In the embodiment of FIGS. 63-75, a wall 23 forms the majority of the bottom side 28 with a second opening or cavity opening 29 defined in the bottom side to permit the electrical connecting structure 30 to enter the housing 20 to connect with the interface 31.

Figure 73:
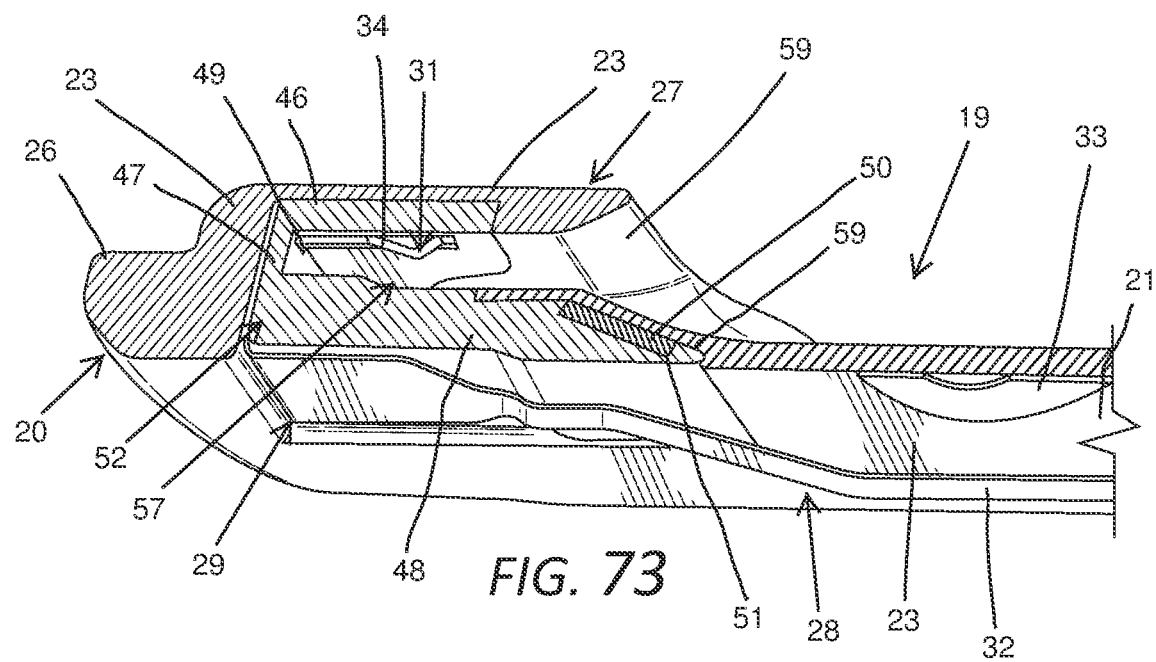
FIG. 73 is a partial longitudinal cross-sectional view of the housing assembly of FIG. 67.
Figure 74:
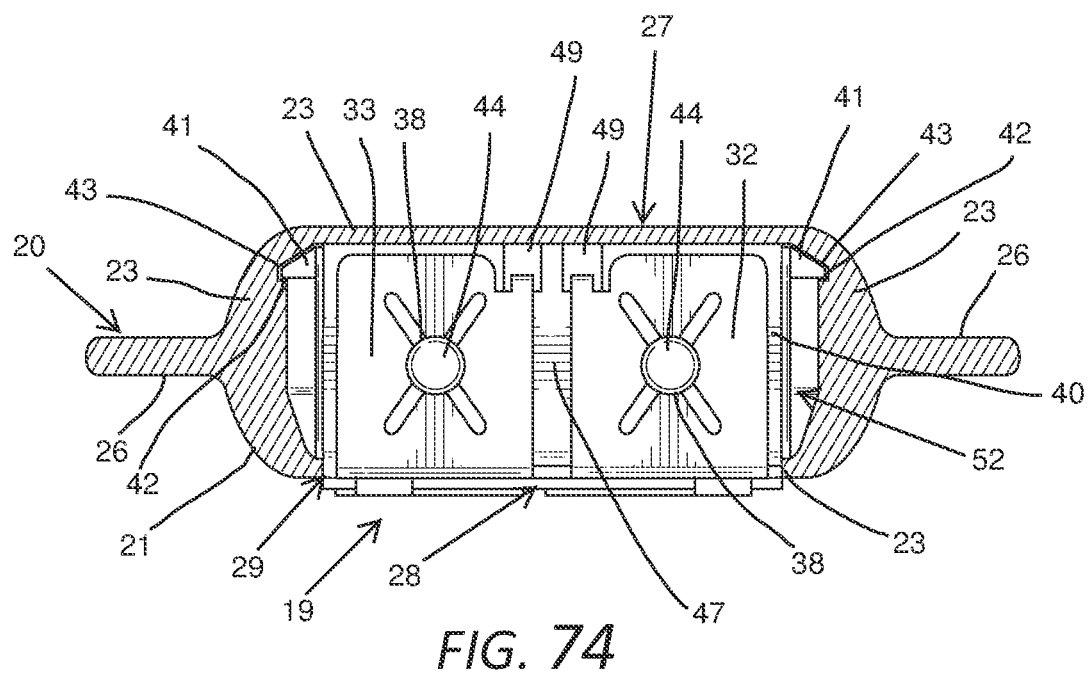
FIG. 74 is a lateral cross-sectional view of the housing assembly of FIG. 67.

In one embodiment, the housing 20 further includes a carrier 40 that is connected to the receptacle 21 and holds and supports a portion of the electrical connecting structure 30 to be exposed to the chamber 22 to form the interface 31. The carrier 40 is formed as a separate piece from the receptacle 21 in the embodiment of FIGS. 63-75, and is connected to the receptacle 21 by a mechanical engaging structure. The carrier 40 in this embodiment has two retaining tabs 41 that extend outwardly from the lateral sides of the carrier 40 and engage engagement surfaces 42 located on the inner sides of the walls 23 on the lateral sides of the receptacle 21 to retain the carrier 40 in connection with the receptacle 21. This engagement is shown in FIG. 74, where the engagement surfaces 42 are defined within slots 43 on the walls 23 of the receptacle 21, in which the tabs 41 are received. In this embodiment, the carrier 40 is inserted through the cavity opening 29 on the bottom side 28 of the receptacle 21 until the tabs 41 are received in the slots 43, and the tabs 41 have ramped surfaces to aid this insertion. It is understood that additional connecting structures may be used in this embodiment, including other mechanical engaging structures (including separate connectors or fasteners) and/or other types of connecting structures, such as welding, bonding, etc. In other embodiments, the carrier 40 may be connected to the receptacle 21 using a different connecting structure and/or technique, including any structure described above or combinations of such structures.

Figure 71:
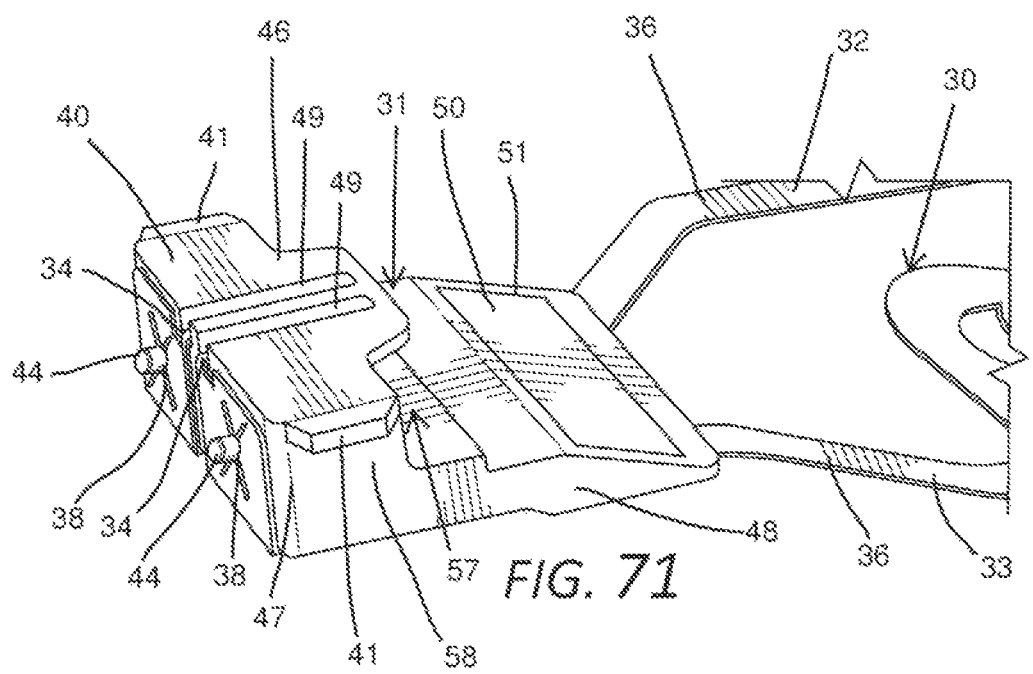
FIG. 71 is a partial top front perspective view of the carrier and the contact members of FIG. 69.
Figure 72:
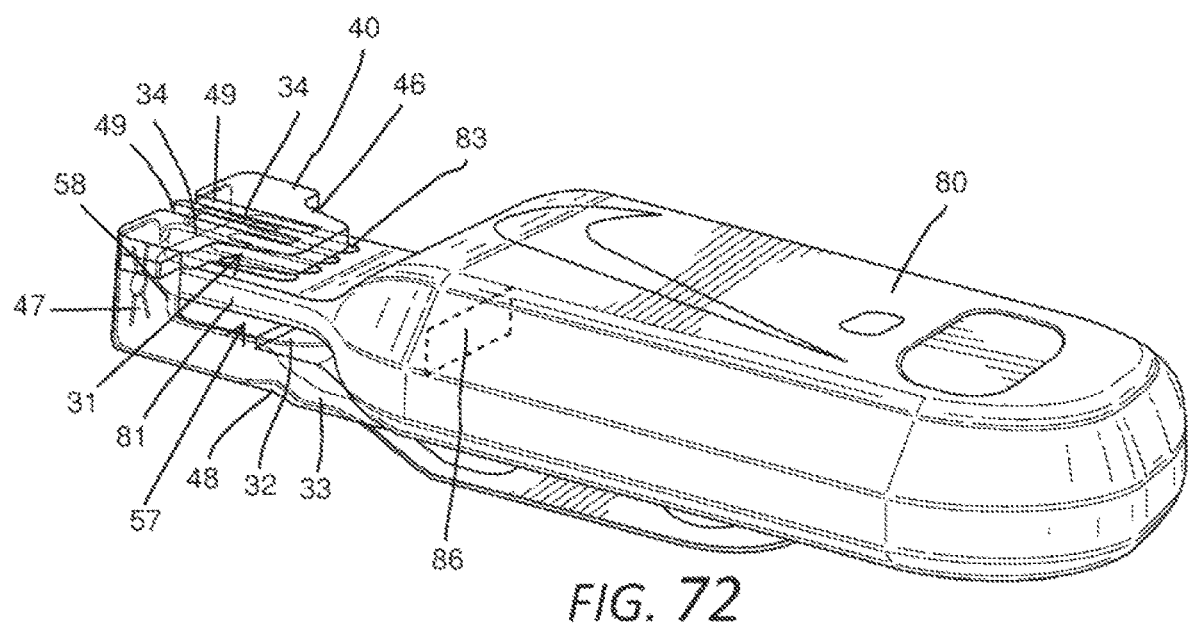
FIG. 72 is a top rear perspective view of the module of FIG. 62 engaged with the carrier and contact members of FIG. 69, with the carrier and the contact members being shown partially transparent.

The carrier 40 is at least partially received in a cavity 52 inside the receptacle 21 that is in communication with the chamber 22, permitting the carrier 40 to position the electrical contacts 34 to be exposed to the chamber. The structure of the carrier 40 includes a shelf 46 that extends into the chamber 22, with the carrier 40 having slots 49 that extend through the shelf 46 to accommodate the electrical contacts 34. The carrier 40 also includes a column 47 that depends from the rear end of the shelf 46 and a base 48 that extends forward from the column 47, such that the carrier 40 has a C-shape, as shown in FIGS. 71-73. The connector 81 of the module 80 may be received between the shelf 46 and the base 48 when the module 80 is received in the chamber 22 in one embodiment, as illustrated in FIG. 72. Additionally, a portion of the base 48 in the embodiment of FIGS. 63-75 extends farther forward and fits with the receptacle 21 to extend below a wall of the receptacle 21, as shown in FIG. 73. This configuration creates a more balanced and multi-point connection between the carrier 40 and the receptacle 21. In further embodiments, the carrier 40 may have a different structure, and/or the carrier 40 may be integrally formed with the receptacle 21 or with a portion of the receptacle 21, such that the carrier 40 is not a separate piece. Further structure of the carrier 40 for supporting portions of the electrical connecting structure 30 is described in greater detail below.

The electrical connecting structure 30 generally creates a pathway for electrical connection of an external component (e.g., the electrically powered component 14 and/or the leads 17) to the module 80 when the module 80 is engaged with the housing 20. In the embodiment of FIGS. 63-75, the electrical connecting structure 30 includes two contact members 32, 33 that are separate from each other and have portions exposed within the chamber 22 to form electrical contacts 34 of the interface 31. It is understood that the number of contact member 32, 33 may be the same as the number of active terminals 83 on the module 80. For example, the interface 31 in FIGS. 63-75 has two electrical contacts 34 (power/ground or +/−), and the connector 81 has two active terminals 83, as described in greater detail below. The contact members 32, 33 illustrated in FIGS. 63-75 each includes a contact pad 35 configured to be connected to an external component (e.g., the leads 17) and an arm 36 that extends from the contact pad 35 into the chamber 22 to form an electrical contact 34. In one embodiment, the arms 36 and the contact members 32, 33 themselves each form a 180° bend between the contact pads 35 and the electrical contacts 34, as shown in FIGS. 68-69, where the arms 36 extend along the bottom side 28 of the receptacle 21, then upward into the receptacle 21, and then back into the chamber 22 to form the electrical contacts 34. The contacts 34 in this embodiment are configured as contact springs that extend into the chamber 22 and exert a downward force on the connector 81 to maintain secure contact, while being able to flex upward to accommodate the shape of the connector 81, but may be differently configured in other embodiments. The contact members 32, 33 in one embodiment may each be made from a single blank of sheet metal material, which is formed into the contact member 32, 33 by various forming operations, such as cutting, stamping, punching, bending, etc. This enables the contact members 32, 33 to be manufactured quickly and easily at low cost. In other embodiments, the contact members 32, 33 may be formed of a different material and/or by a different technique.

Figure 67:
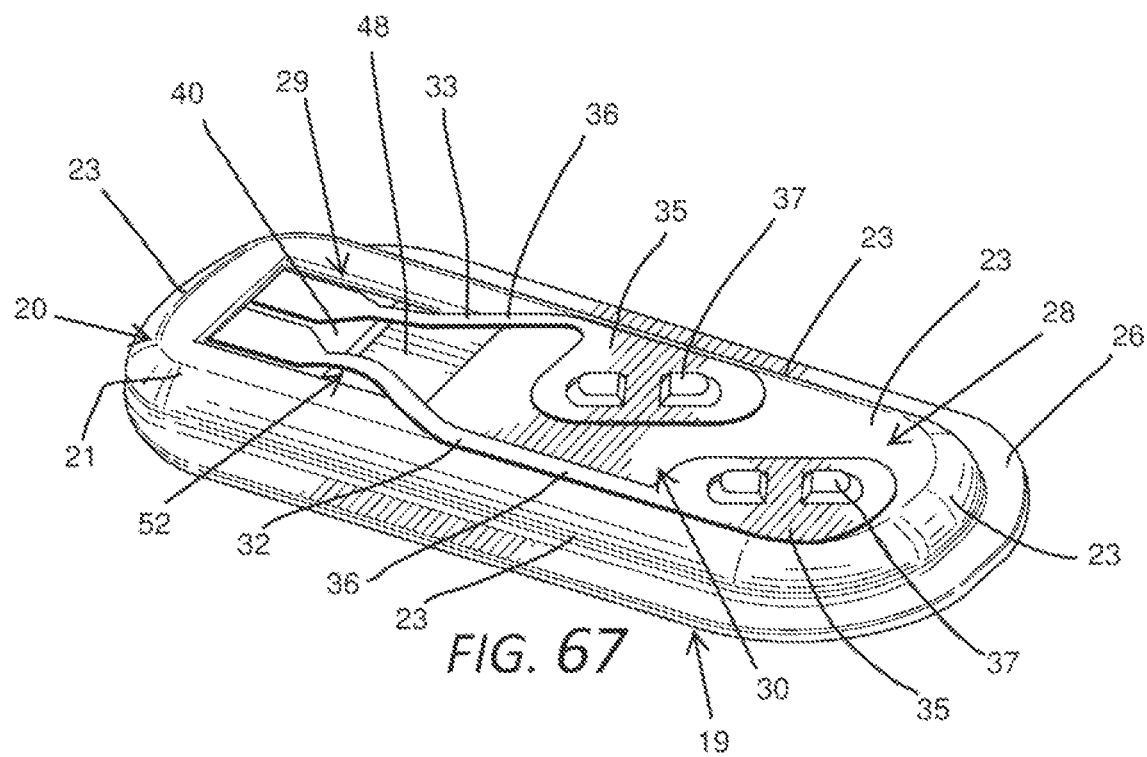
FIG. 67 is a bottom rear perspective view of one embodiment of a housing assembly including the housing of FIG. 63, according to aspects of the present disclosure.
Figure 68:
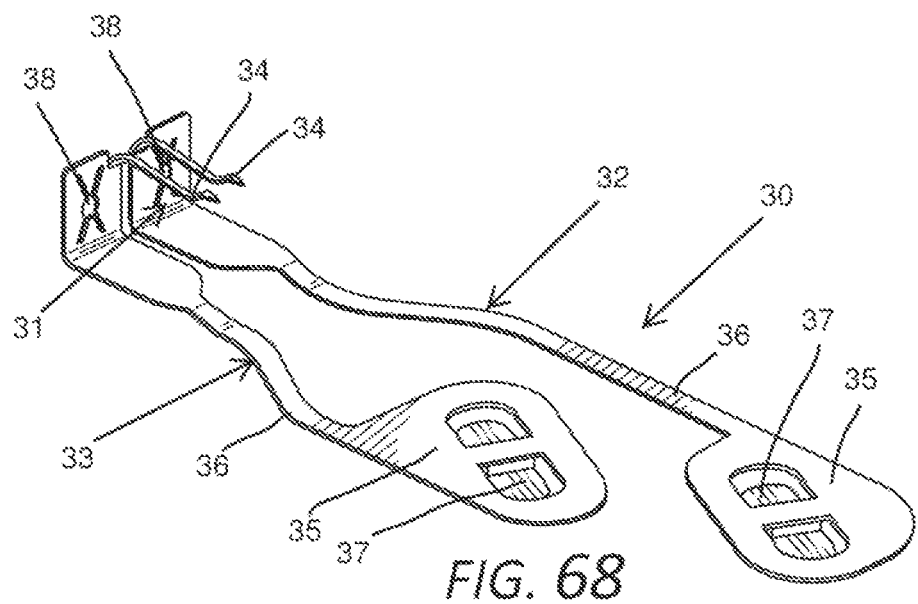
FIG. 68 is a top rear perspective view of one embodiment of a pair of electrical contact members of the housing assembly of FIG. 67, according to aspects of the present disclosure.
Figure 69:
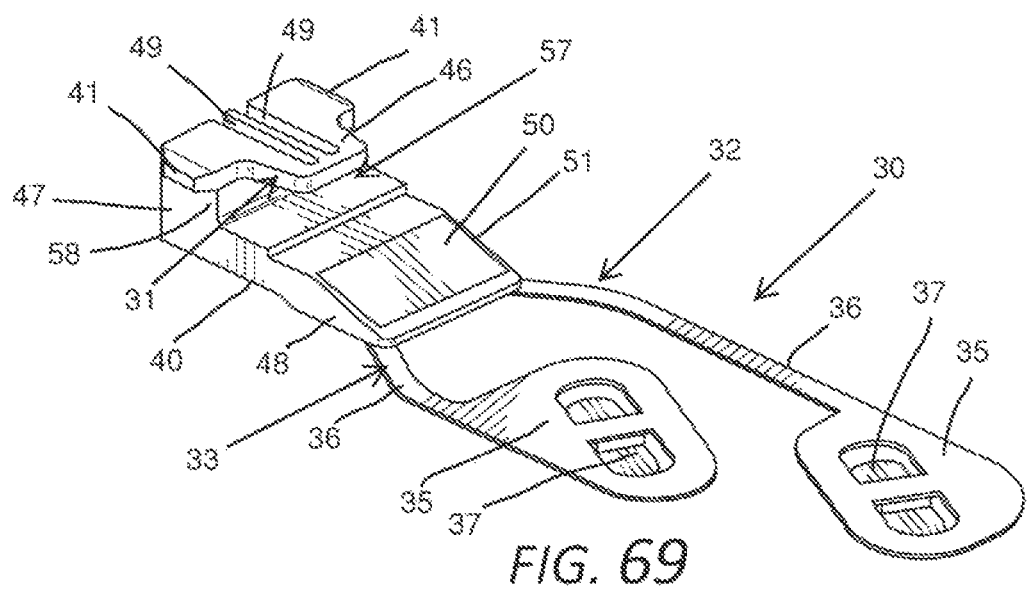
FIG. 69 is a top rear perspective view of one embodiment of a carrier of the housing assembly of FIG. 67 engaged with the contact members, according to aspects of the present disclosure.
Figure 70:
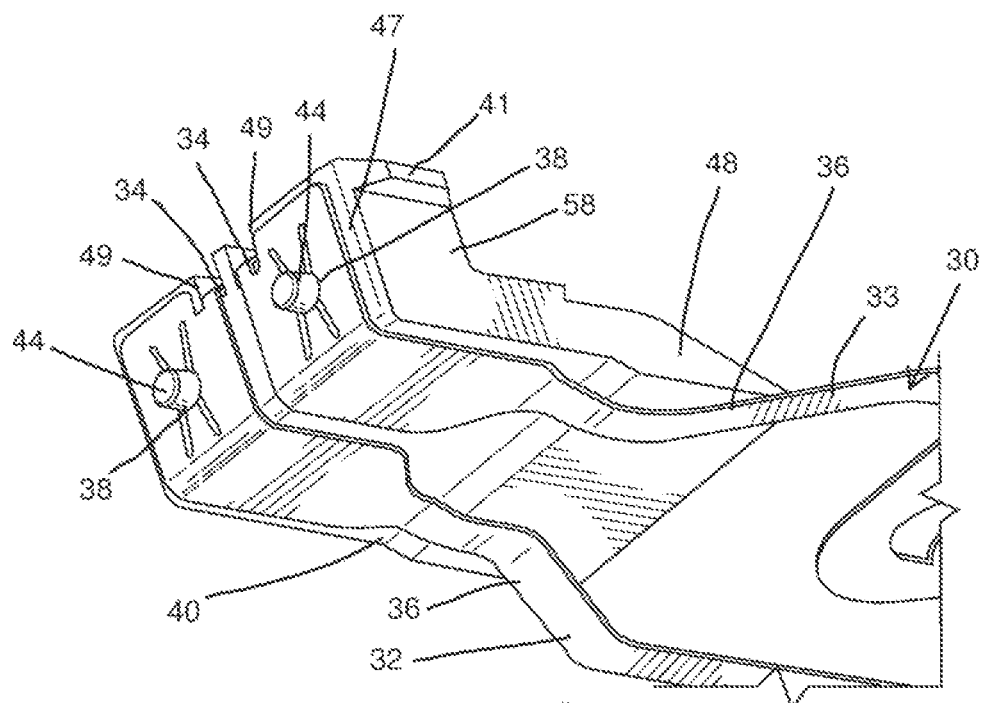
FIG. 70 is a partial bottom front perspective view of the carrier and the contact members of FIG. 69.

The contact pads 35 are shown in FIGS. 67-69 as having enlarged widths relative to the arms 36, providing a large surface for connection of a lead 17 or other external component. Connection of the leads 17 to the contact pads 35 places the leads 17 and the component(s) to which the leads 17 are connected in communication with the contact members 32, 33, and thereby in communication with the interface 31. As shown in FIG. 67, the contact pads 35 may have a width that is greater than half the width of the bottom side 28 of the receptacle 21, and the contact pads 35 are staggered with overlapping widths and have structure (e.g., angled surfaces) to provide maximum contact area within the boundaries of the bottom side 28 of the receptacle 21.

Figure 76:
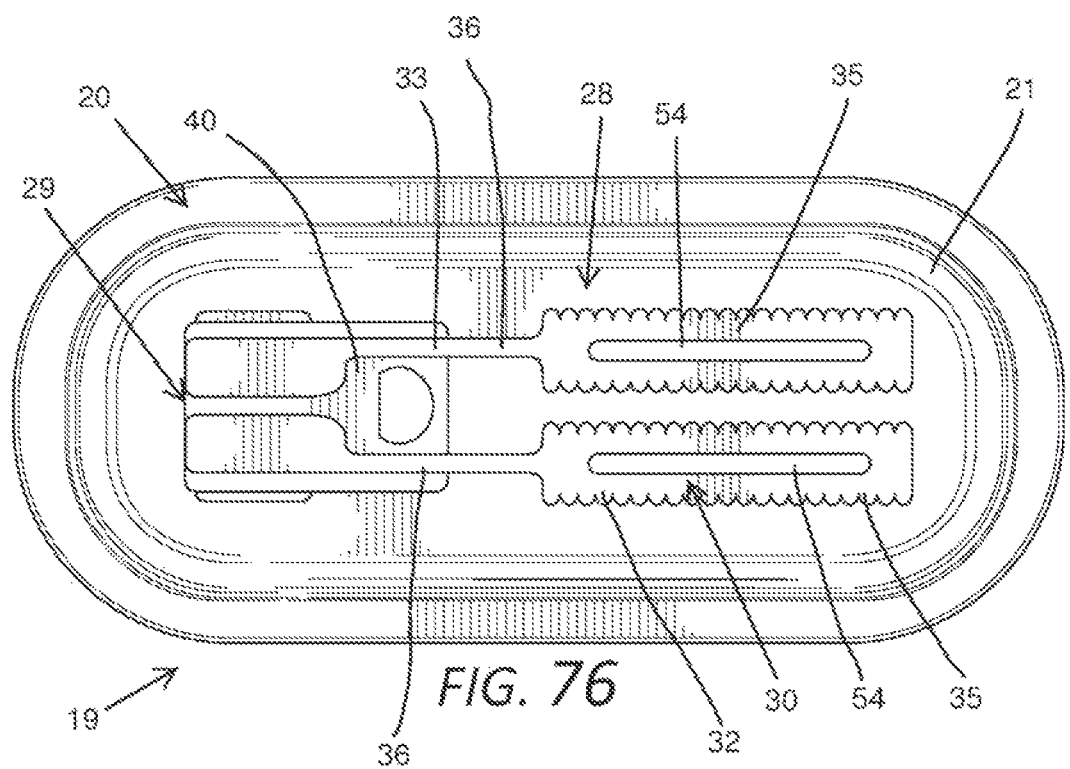
FIG. 76 is a bottom view of another embodiment of a housing assembly according to aspects of the present disclosure.
Figure 77:
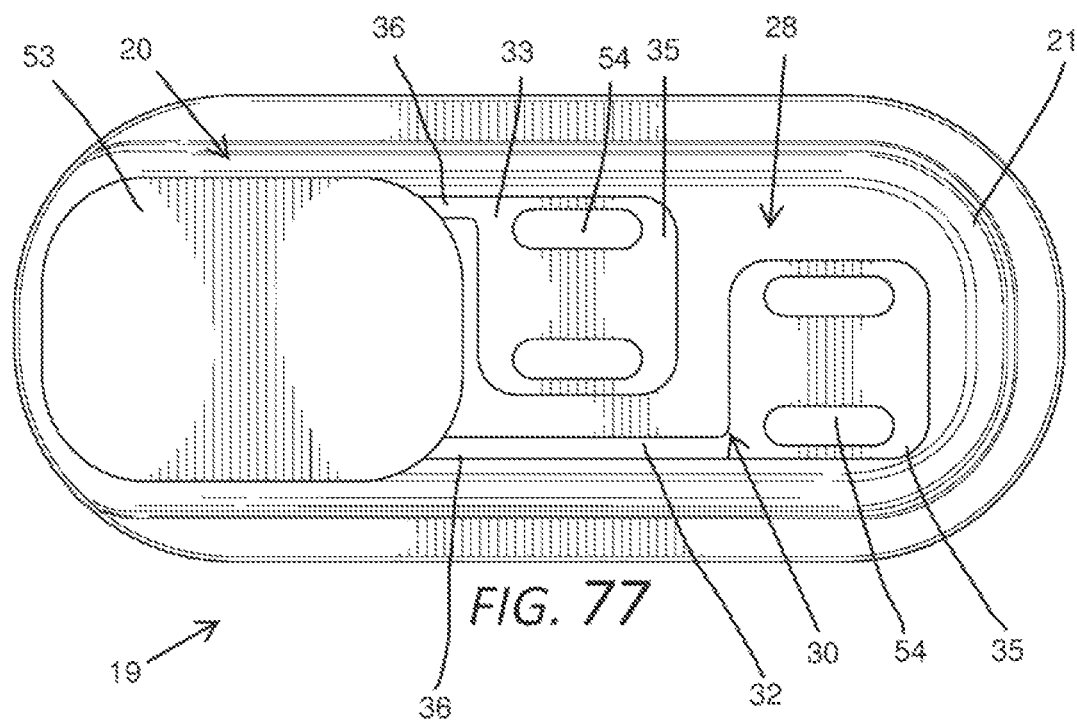
FIG. 77 is a bottom view of another embodiment of a housing assembly according to aspects of the present disclosure.
Figure 81:
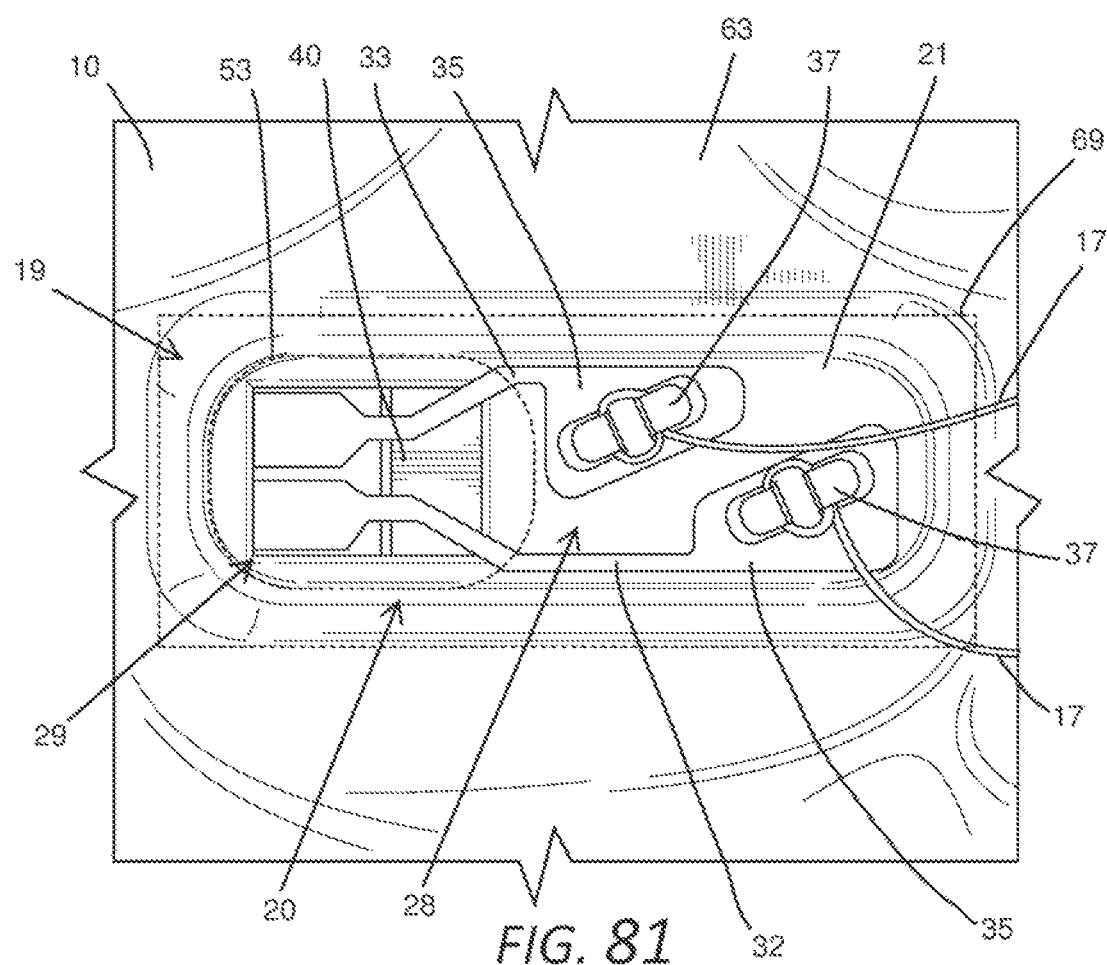
FIG. 81 is a plan view of the housing assembly and a portion of the interior of the wearable article of FIG. 78, with conductive leads connected to the housing assembly.
Figure 88:
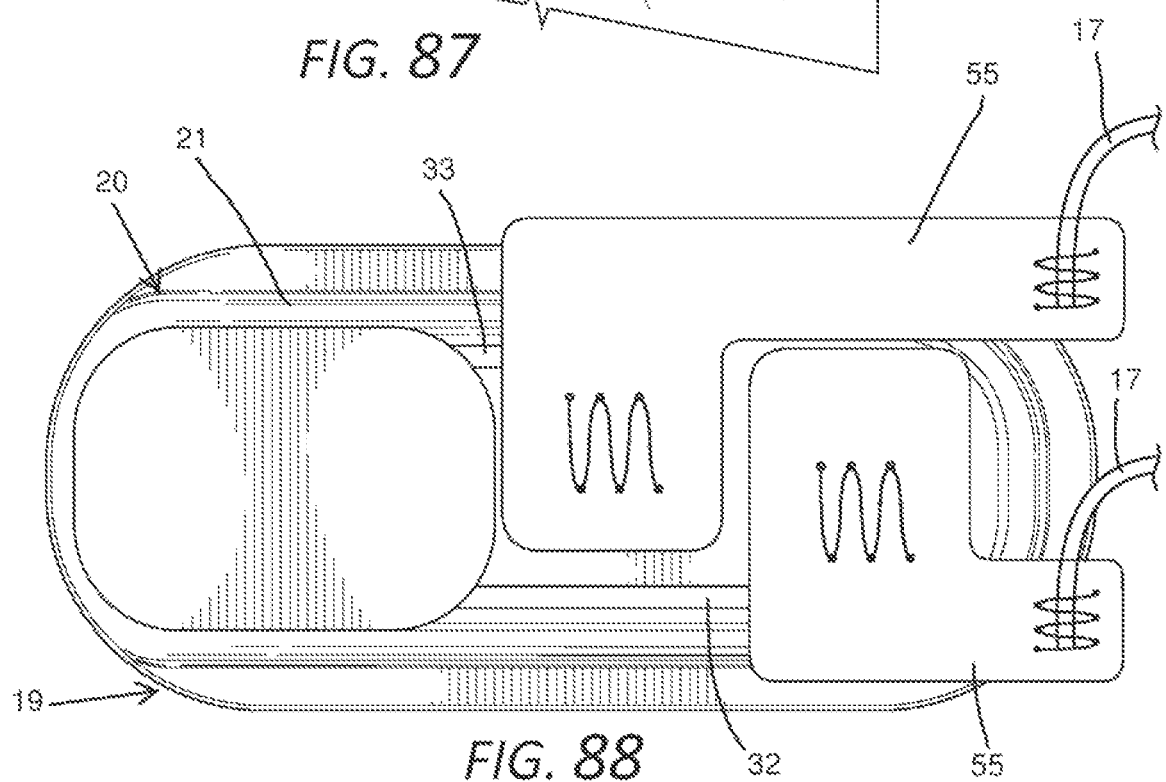
FIG. 88 is a bottom view of another embodiment of a housing assembly according to aspects of the present disclosure, with conductive leads connected to the housing assembly.

The contact pads 35 may be configured for connection to the leads 17 using various different structures, which may be more particularly suited to connection to a specific type of lead 17 (e.g., wire, fabric, thread, conductive trace, etc.). The contact pads 35 may each have at least one projection 37 for connection of a lead 17 by winding around the projection(s) 37 in one embodiment. In the embodiment of FIGS. 63-75, each contact pad 35 has two projections 37, and the leads 17 are connected by winding around both projections 37, as shown in FIG. 81. In other embodiments, the contact pads 35 may be located in a different location and may have any structure that functions to form a connection with an external component. For example, the contact pads 35 in FIG. 76 have a ridged structure with a central slot 54, which permits winding of leads 17 around the exterior (e.g., wire leads) or threading of the leads 17 through the slot 54 (e.g., sewing conductive thread leads). As another example, the contact pads 35 in FIG. 77 have a pair of slots 54, which can permit winding of the leads 17 between the slots 54 or threading the leads 17 through both slots 54. As a further example, the leads 17 can be connected to intermediate conductors 55, as shown in FIG. 88, which are then connected to the contact members 32, 33. In the embodiment of FIG. 88, the leads 17 are conductive thread leads, and the intermediate conductors 55 are pieces of a conductive fabric. The leads 17 in this configuration are sewn/stitched to the intermediate conductors 55, which are then sewn/stitched to the contact pads 35 of the two contact members 32, 33, which may be configured as shown in FIG. 77. In other embodiments, other types and configurations of intermediate conductors 55 may be used, including in connection with leads 17 and/or contact members 32, 33 that are differently configured. It is understood that the contact members 32, 33 in the embodiments of FIGS. 76-77 and 26 may be otherwise configured substantially similarly to the contact members 32, 33 in FIGS. 63-75 or according to any other embodiment described herein.

As illustrated in FIGS. 67 and 73, the contact pads 35 in this embodiment are external to the housing 20, being positioned adjacent the bottom side 28 of the receptacle 21, and the arms 36 extend from the exterior of the housing 20 through one of the walls 23 of the receptacle 21 (e.g., through the cavity opening 29) and into the chamber 22. Additionally, the contact members 32, 33 each have a mounting structure for connection to the housing 20 in one embodiment. As shown in the embodiment of FIGS. 68-74, the carrier 40 has two posts 44 on the rear surface, and the arms 36 of the contact members 32, 33 each have a receiver 38 that receives one of the posts 44. The portions of the arms 36 surrounding the receivers 38 are enlarged, and the receivers 38 are configured for receiving the posts 44 in a press-fit connection in this embodiment. It is understood that in one embodiment, the contact members 32, 33 may be provided with a greater number of connection and/or bracing points to hold the contact members 32, 33 in place after complete assembly, and that the mounting structure (e.g., posts 44 and receivers 38) may be used to connect the contact members 32, 33 to the carrier 40 during assembly and prior to connection of the carrier 40 to the receptacle 21 in one embodiment. The contact members 32, 33 may have additional or different mounting structure in other embodiments.

Figure 84:
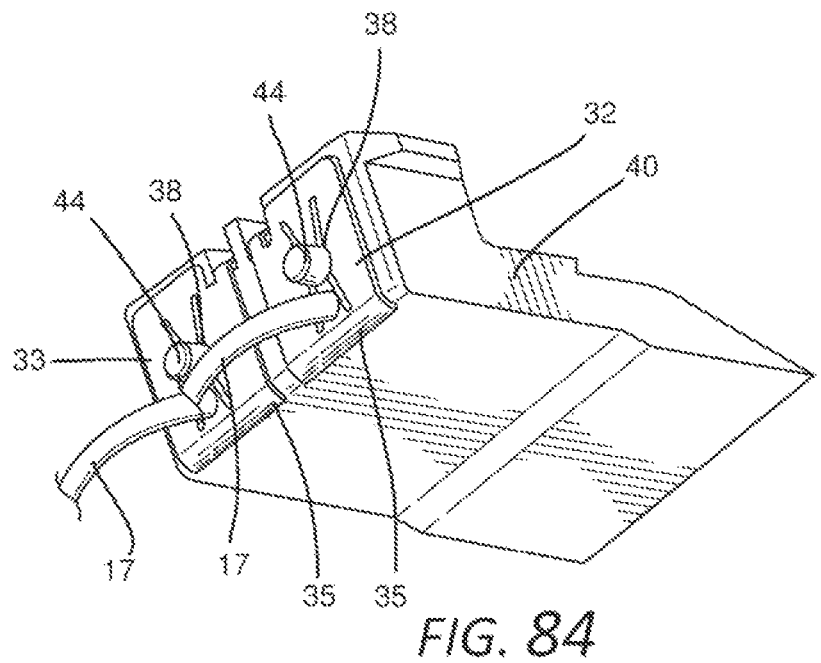
FIG. 84 is a bottom front perspective view of another embodiment of a carrier, contact members, and conductive leads according to aspects of the present disclosure.

In another embodiment, illustrated in FIG. 84, the contact members 32, 33 may have contact pads 35 that are not located on the exterior of the housing 20. In this embodiment, the contact pads 35 are located along the back wall of the carrier 40 and within the cavity 52 after assembly. As shown in FIG. 84, the electrical contacts 34 extend directly from the contact pads 35 in this embodiment. The leads 17 are shown as being welded to the contact pads 35 in FIG. 84, but the contact pads 35 may be provided with other connecting structure in other embodiments. The contact pads 35 in FIG. 84 further include mounting structure 38 for connection to the carrier 40, as described in greater detail below.

The carrier 40 is configured for positioning the electrical contacts 34 of the contact members 32, 33 in a position to be exposed to the chamber 22 of the housing 20 for connection to the module 80, in addition to the mounting structure 38, 44. In one embodiment 3, the electrical contacts 34 are received within the slots 49 in the carrier 40, as shown in FIGS. 69-74. The arms 36 of the contact members 32, 33 in this embodiment extend along the rear surface of the carrier 40 as described above, and the slots 49 extend through to the rear of the carrier 40, such that the electrical contacts 34 extend forwardly into the slots 49 and are at least partially received in the slots 49. The slots 49 allow the electrical contacts 34 to be exposed to the chamber 22 below the shelf 46 of the carrier 40, while also providing room for the contacts 34 to flex upward if necessary when engaged by the module 80. The carrier 40 in this configuration provides both a positioning or registration function with respect to the module 80, positioning both the electrical contacts 34 and the module connector 81 in position for connection, as well as a protective function for the electrical contacts 34. The carrier 40 and/or the contact members 32, 33 may have different structures in other embodiments, and may have complementary structures to facilitate the positioning and protective functions.

In one example embodiment, the housing 20 includes a magnet 50 connected to the housing 20 and configured for interaction with the module 80 when the module 80 is engaged with the receptacle 21, as described in greater detail below. The magnet 50 is positioned so that the magnetic field of the magnet 50 penetrates the chamber 22. The housing 20 in the embodiment of FIGS. 63-75 includes a magnet 50 that is engaged with the carrier 40 and is received within a recess 51 on the carrier 40 adjacent to the chamber 22. The recess 51 is located on the distal end of the base 48, which is distal from the column 47 in the embodiment illustrated in FIGS. 69-73. The magnet 50 in this embodiment is embedded within the housing 20 and not physically exposed to the chamber 22, with one of the walls 23 of the receptacle 21 positioned between the magnet 50 and the chamber 22 and the magnet 50 being positioned on the outer surface of the wall 23, as illustrated in FIG. 73. The magnet 50 may be held within the recess 51 by engagement by both the carrier 40 and the adjacent wall 23 of the receptacle 21 in one embodiment. Additional or alternate retaining structures may be used in other embodiments, including a bonding material, mechanical retaining structures, fasteners, etc. In other embodiments, the magnet 50 may be integrally molded within the housing 20, such as within the carrier 40 or within a wall 23 of the receptacle 21, or the magnet 50 may be mounted on the carrier 40 using a different structure. In additional embodiments, the magnet 50 may be mounted on the receptacle 21 and/or the magnet 50 may be positioned so that at least a portion of the magnet 50 is physically exposed within the chamber 22.

Figure 75:
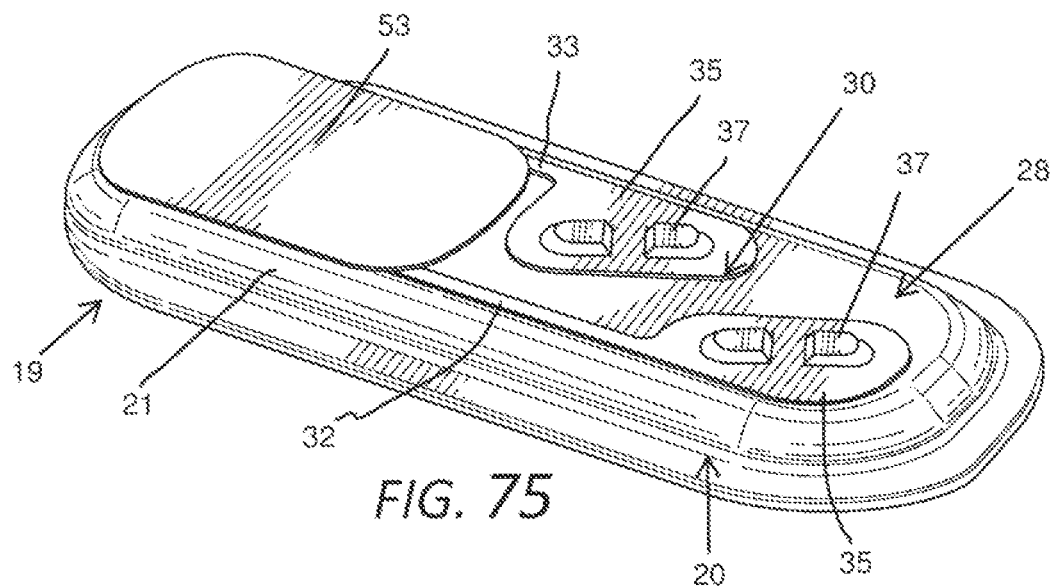
FIG. 75 is a bottom rear perspective view of the housing assembly of FIG. 67 with one embodiment of an insulative material covering a portion of the housing assembly according to aspects of the present disclosure.

The housing assembly 19 is assembled according to one embodiment by first connecting the contact members 32, 33 and the magnet 50 to the carrier 40. In the embodiment of FIGS. 63-75, the magnet 50 may be secured by placing the magnet 50 inside the recess 51, and applying any bonding material or other retaining structure. The contact members 32, 33 may be connected to the carrier 40 by placing the contact members 32, 33 in the positions shown in FIGS. 69-71, with the posts 44 received in the receivers 38 and the electrical contacts 34 received in the slots 49. The sub-assembly including the carrier 40, as well as the magnet 50 and the contact members 32, 33 connected to the carrier 40, can then be connected to the receptacle 21. This connection can be accomplished by inserting the carrier 40 into the cavity 52 in the receptacle 21. In the embodiment of FIGS. 63-75, the insertion of the carrier 40 causes the retaining tabs 41 to slide into the slots 43 and engage the engagement surfaces 42 to retain the carrier 40 within the cavity 52. When connected in this manner, portions of the contact members 32, 33 are engaged between the carrier 40 and the surfaces of the receptacle 21 that define the cavity 52, and the magnet 50 is engaged between the carrier 40 and the adjacent wall 23 of the receptacle, which adds stability to the connections between the carrier 40 and the magnet 50 and the contact members 32, 33. The bottom of the carrier 40 and the opening 29 of the cavity 52 may then be covered with a covering member 53, as shown in FIG. 75. The covering member 53 may be, e.g., a patch of material or an applied coating that adheres to the components of the housing assembly 19. Additionally, the covering member 53 may be moisture resistant and function to seal the cavity against ingress of moisture, dirt, or other contaminants and/or may be electrically insulative to insulate the contact members 32, 33 against shorting. The housing assembly 19 at this stage can then be connected to the wearable article 10.

Figure 82:
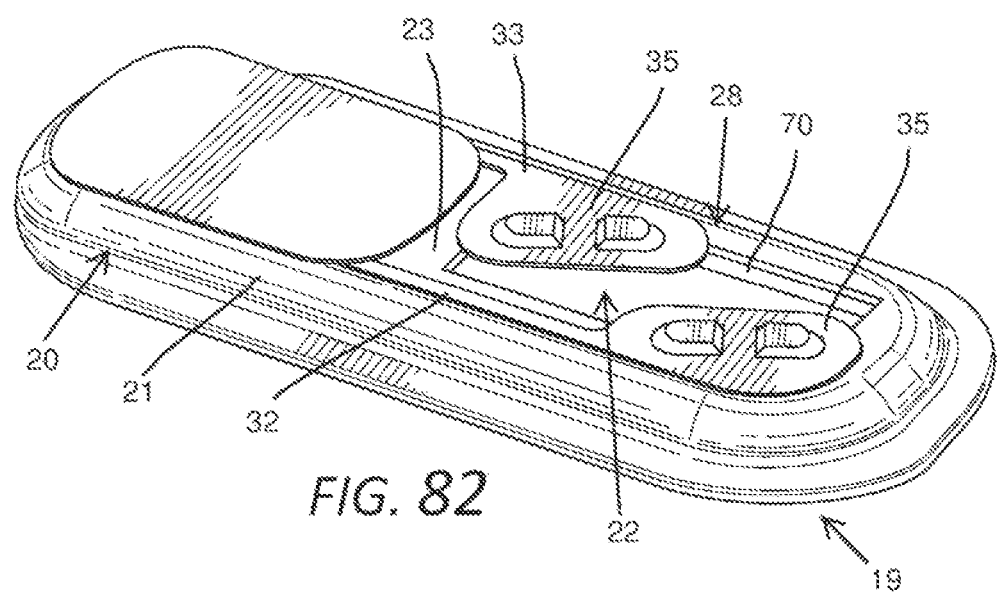
FIG. 82 is a bottom rear perspective view of another embodiment of a housing assembly according to aspects of the present disclosure.
Figure 83:
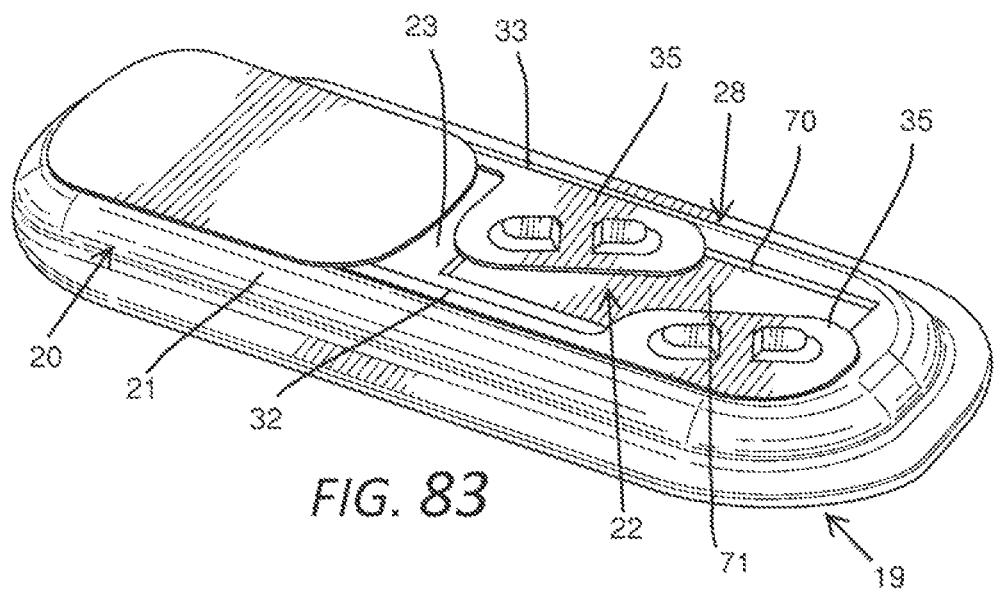
FIG. 83 is a bottom rear perspective view of the housing assembly of FIG. 82.

In one embodiment, the leads 17 are connected to the contact members 32, 33 prior to connection of the housing assembly 19 to the article 10. As discussed above, the leads 17 are connected to contact pads 35 on the contact members 32, 33 in one embodiment, and the leads 17 are connected by winding around projections 37 on the contact pads 35 in the embodiment shown in FIG. 81. In other embodiments, the leads 17 may be connected to the contact members 32, 33 in another configuration, such as the configurations shown in FIGS. 76-77, 84, and 88. Alternately, the leads 17 may be connected to the contact members 32, 33 after the housing assembly 19 is connected to the article 10. In another embodiment, the housing 20 may be provided with access features to access the leads 17 and the contact pads 35 after connection of the housing 20 to the article 10, such as shown in FIGS. 82-83. FIG. 82 illustrates a housing 20 where the receptacle 21 has an opening 70 that extends through the wall 23 forming the bottom side 28 of the receptacle 21, providing access to the leads 17 and the contact pads 35 from within the chamber 22. The opening 70 can be sealed with a cover 71 when the desired access is complete, in order to protect against shock and/or contamination. The cover 71 may be applied on the inner surface of the chamber 22, such as a liquid sealant, a filler resin, or a cover piece connected to the receptacle 21, and the cover 71 may be permanent or removable.

Figure 85:
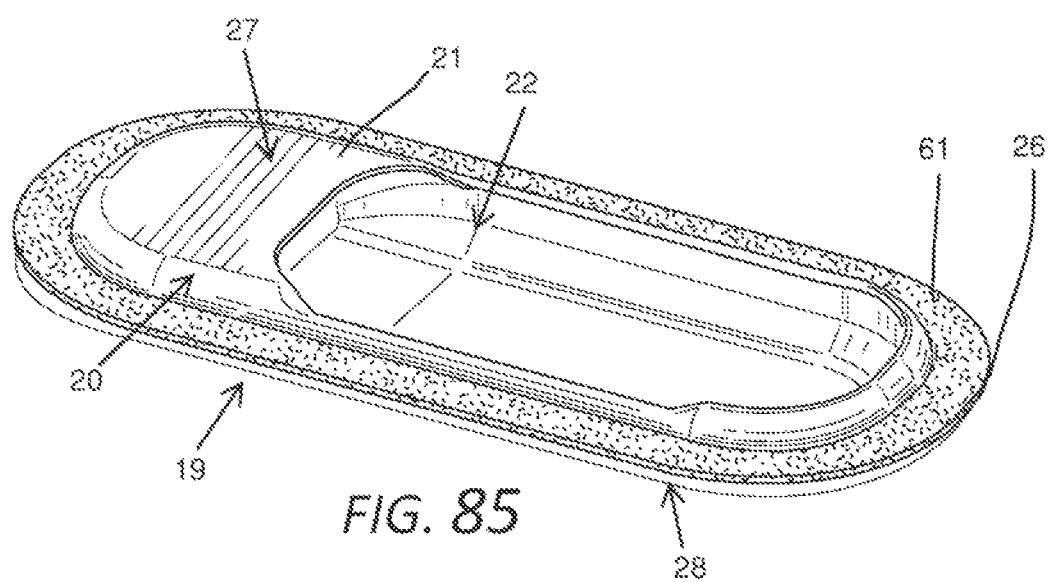
FIG. 85 is a top rear perspective view showing a step in one embodiment of a process for connecting the housing of FIG. 62 to a wearable article, according to aspects of the present disclosure.
Figure 86:
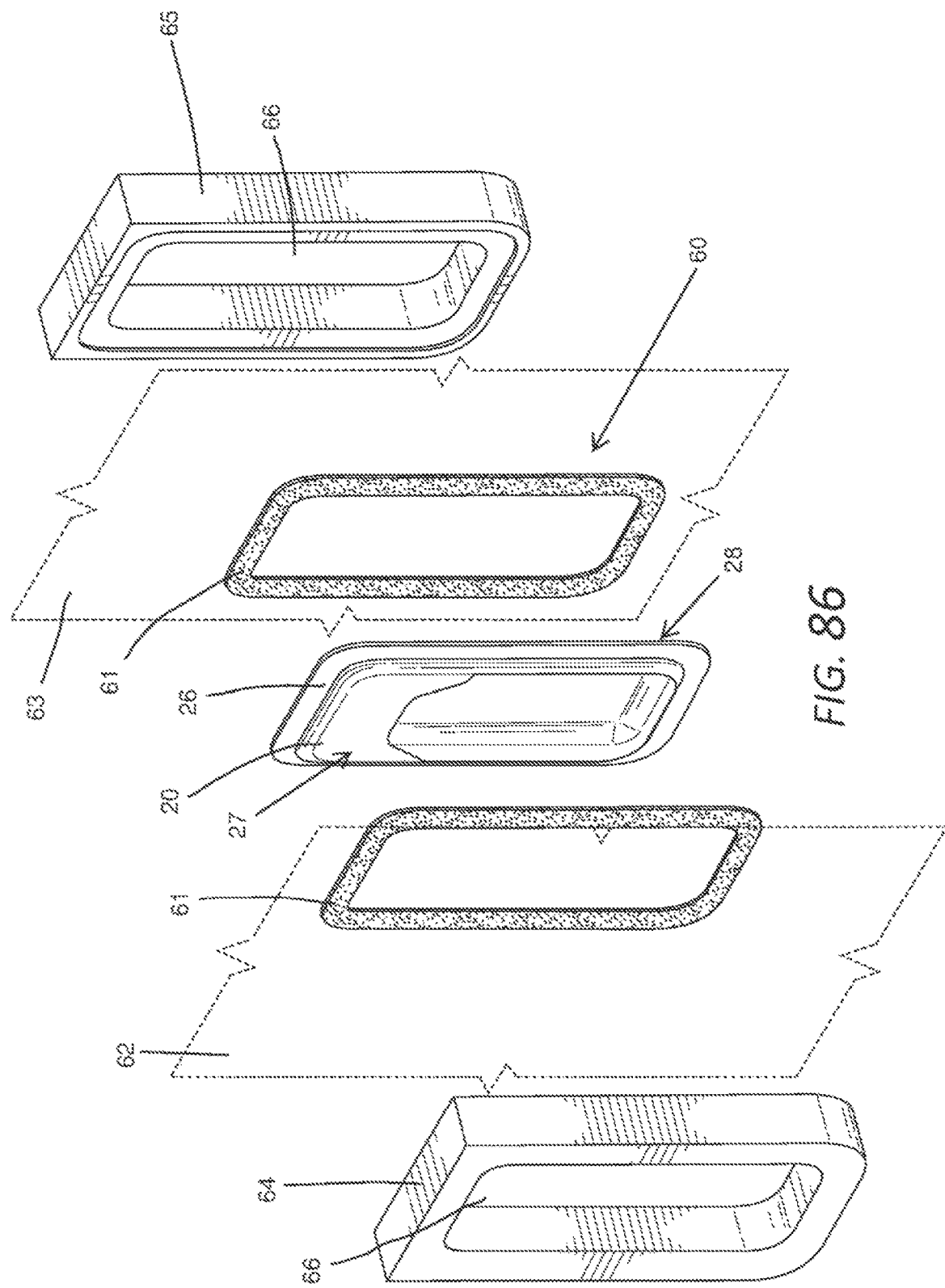
FIG. 86 is an exploded perspective view showing another step in the embodiment of the process for connecting the housing of FIG. 62 to the wearable article.
Figure 87:
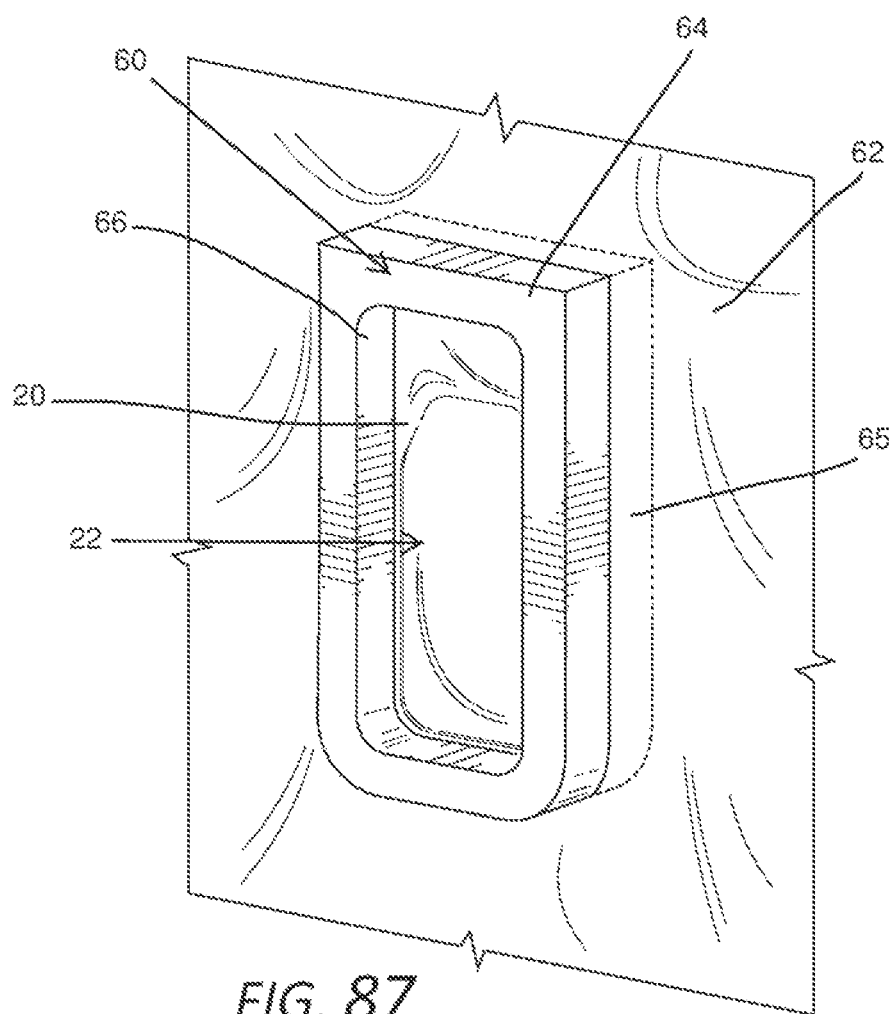
FIG. 87 is a perspective view showing another step in the embodiment of the process for connecting the housing of FIG. 62 to the wearable article.

In one example embodiment, the housing assembly 19 is connected to the article 10 by bonding the housing assembly 19 to the article 10. FIGS. 85-87 illustrate an embodiment of a method and a heat press assembly 60 for bonding a housing assembly 19 to an article 10 using a heat press operation on at least a portion of the housing 20. The heat pressing may utilize a bonding material 61, such as a heat-activated film. The heat press assembly 60 in FIGS. 86-87 is configured for heat pressing around the flange 26 of the housing 20, with the flange 26 being pressed between at least a top layer 62 and a bottom layer 63 of fabric or other material forming the adjacent portions of the article 10. The top and bottom layers 62, 63 may be separate pieces or may be part of a single piece that is folded over to create both layers 62, 63. It is understood that additional layers may be used, and that the top and bottom layers 62, 63 in the embodiment shown in FIGS. 85-87 may include multiple top layers 62 or bottom layers 63, respectively. Prior to heat pressing as shown in FIGS. 85-87, the components to be bonded are assembled in a layered configuration for bonding, such as having the bonding material 61 applied around top and bottom sides of the flange 26 of the housing 20, and the top and bottom layers 62, 63 positioned above the top side and below the bottom side of the flange 26, respectively. In one embodiment, the housing assembly 19 may first be connected to one or both layers 62, 63 of the article 10 by a temporary connection, e.g., by stitching, in order to hold the housing assembly 19 in place during the operation.

Figure 89:
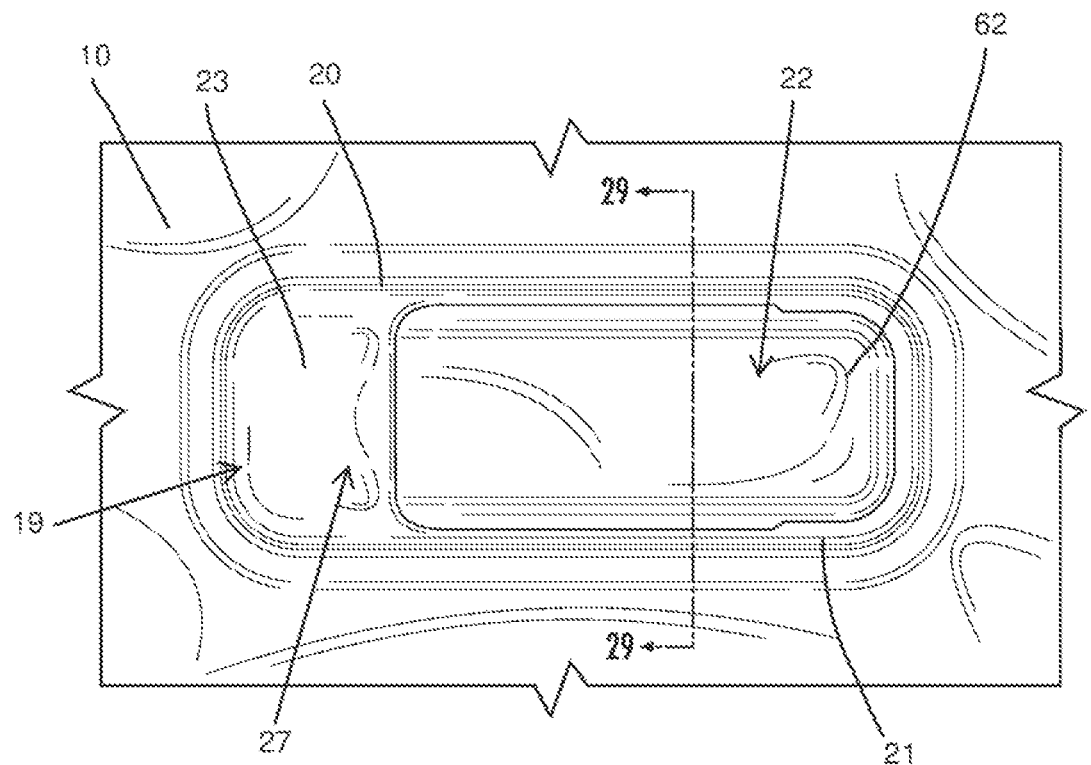
FIG. 89 is a plan view of another embodiment of a housing assembly connected to a wearable article according to aspects of the disclosure.
Figure 90:
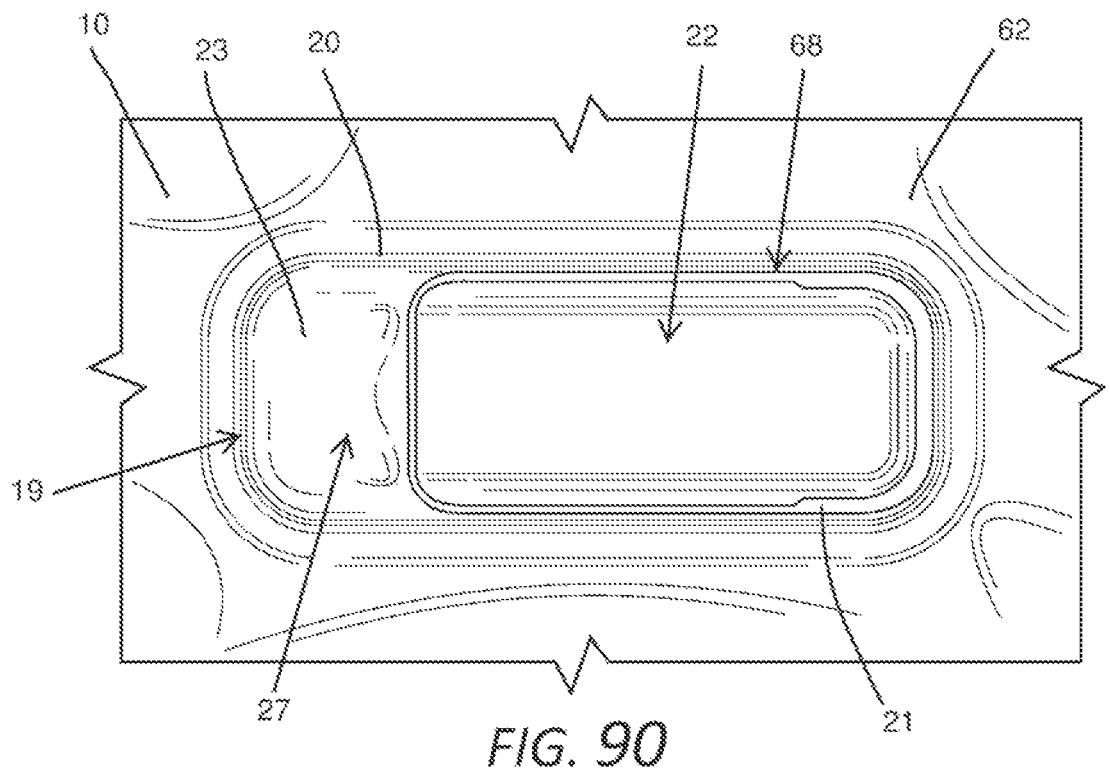
FIG. 90 is a plan view of another embodiment of a housing assembly connected to a wearable article according to aspects of the disclosure.
Figure 91:
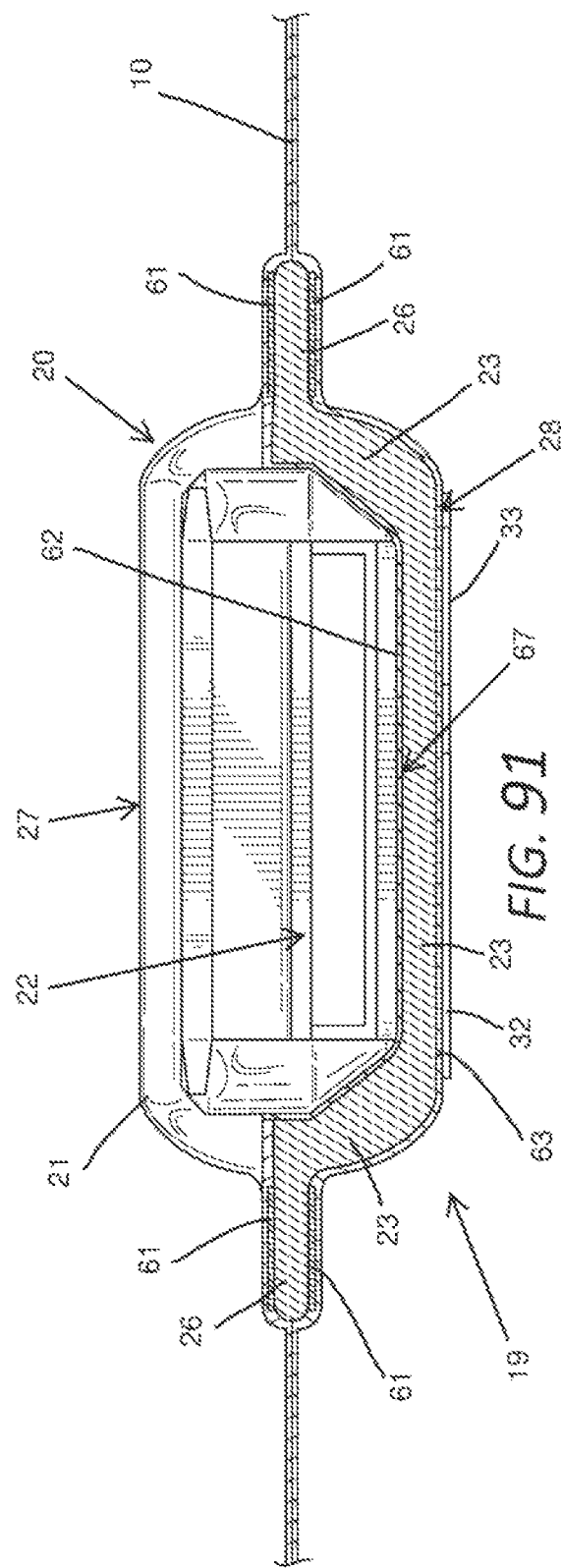
FIG. 91 is a cross-section view taken along lines 29-29 of FIG. 89.

The heat press assembly 60 as shown in FIGS. 86-87 includes two opposed mold pieces 64, 65 that are annular in shape, each having an internal opening 66, so that the mold pieces 64, 65 are configured to press only around the flange 26 of the housing 20. In this configuration, the main body of the housing 20 is received within the opening 66, so that the mold pieces 64, 65 do not press the main body of the housing 20 or the adjacent portions of the layers 62, 63, which localizes the heat application and avoids creating unwanted marks or discolorations on the non-pressed portions of the article 10 and the housing 20. In the embodiment shown in FIGS. 85-87, the layers 62, 63 of the material cover both the top and bottom sides 27, 28 of the receptacle 21. In this configuration, a hole or slit (not shown) is formed in the top layer 62 to provide access to the interface 31, and another hole or slit (not shown) is formed in the bottom layer 63 to provide access to the contact pads 35. The top layer 62 may be pushed down into the chamber 22 of the receptacle 21, as shown in FIGS. 89 and 91, and the arms 36 and contact pads 35 of the contact members 32, 33 may extend through the bottom layer 63 and be located below the bottom layer 63, as shown in FIGS. 81 and 91. In one embodiment, the top layer 62 may further be bonded to the housing 20 within the chamber 22 of the receptacle 21, such as by application of additional bonding material between the top layer 62 and one or more interior surfaces of the receptacle 21, such as at a location 67 as shown in FIG. 91. The additional bonding material may be heat pressed, either by modification of the top die 64 to heat press in the desired location or by use of a separate die (not shown) in the same or a subsequent heat pressing operation. Alternately, the additional bonding material may not require heat pressing, such as glue, cement, or other adhesive. Other portions of the housing 20 may be bonded to the layers 62, 63 in a similar manner. In another embodiment, a larger opening may be cut in the top layer 62, such as an opening 68 approximately the same size as the access opening 24 of the receptacle 21, as shown in FIG. 90.

After the leads 17 are connected to the contact members 32, 33 and the housing assembly 19 is connected to the article 10, an insulative material 69 may be applied to cover part or all of the exposed portions of the electrical connecting structure 30 in one embodiment, as shown in FIG. 81. In this embodiment, the insulative material 69 covers at least the contact pads 35 and the connections to the leads 17. The insulative material 69 in the embodiment of FIG. 81 covers all portions of the electrical connecting structure 30 that are exposed on the exterior of the housing 20 and below the bottom side 28 of the receptacle 21, including the contact pads 35 and portions of the arms 36 of the contact members 32, 33 that are not already covered by the covering member 53, as well as portions of the leads 17. This insulative material 69 resists shorts and shocks that may occur if both of the contact members 32, 33 are contacted when electrical power is applied. The insulative material 69 may also provide at least some sealing of the electrical connecting structure 30 against ingress of environmental materials, especially moisture. This is particularly advantageous when the housing assembly 19 is connected to an athletic garment, as perspiration could affect the functioning of the module 80 and/or the electrical connecting structure 30, as well as increase the risk of shocks. The insulative material 69 may be the same material used for the covering member 53 in one embodiment. Examples of materials that may be used as the insulative material 69 and/or the material of the covering member 53 include a patch of material or an applied coating that adheres to the components of the housing assembly 19.

In other embodiments, different connection techniques may be used to connect the housing assembly 19 to an article 10 that do not utilize heat pressing, such as by using a different bonding material 61 or by using mechanical connection techniques such as sewing or fasteners. Additionally, the housing assembly 19 can be used in connection with non-wearable articles 10 in other embodiments. The housing assembly 19 provides numerous advantages that can be realized when connected to a wearable article 10 using any connection technique, and that can also be realized when used in connection with a different type of article 10.

Figure 92:
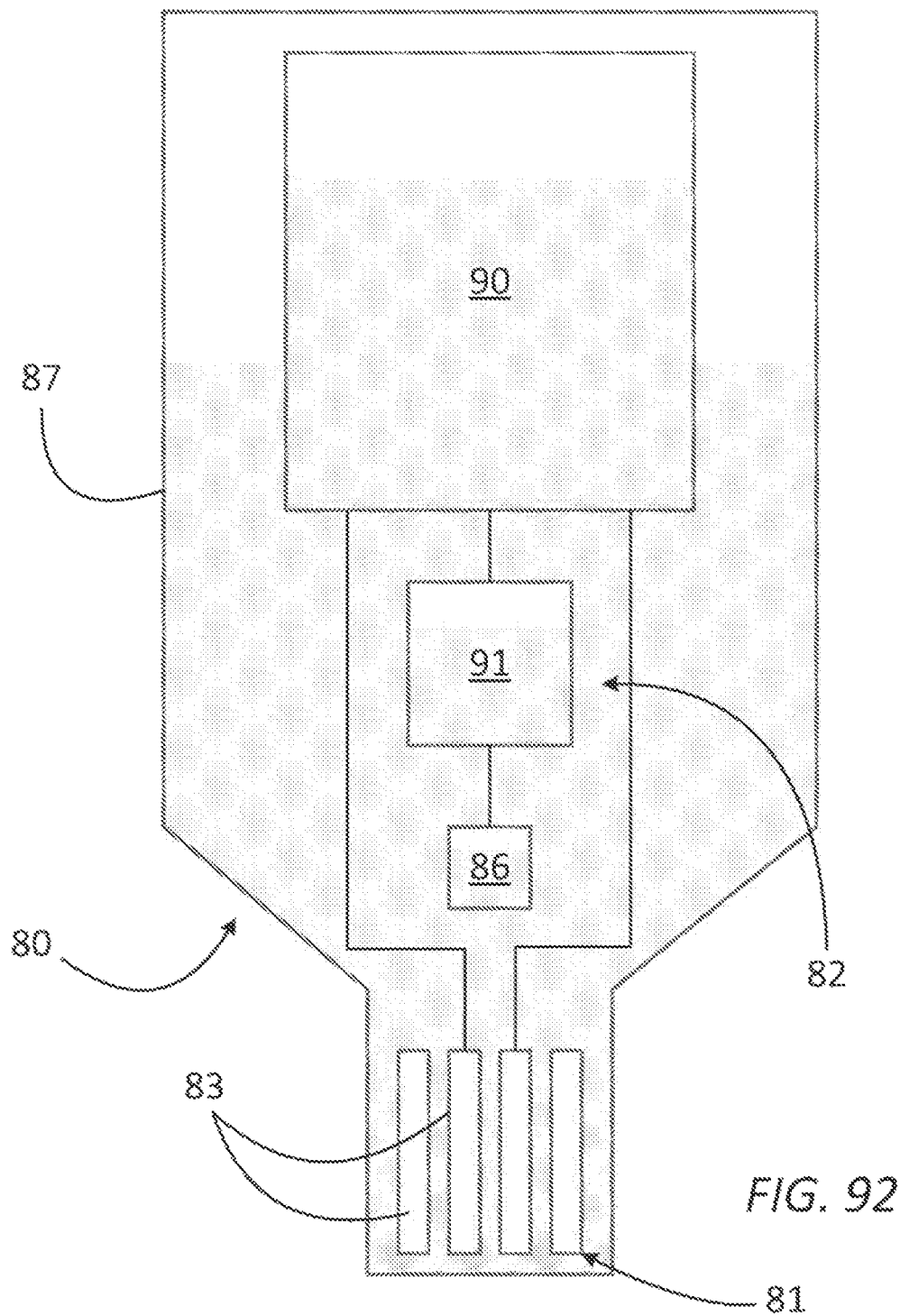
FIG. 92 is a schematic view of one embodiment of an electronic module according to aspects of the disclosure.
Figure 93:
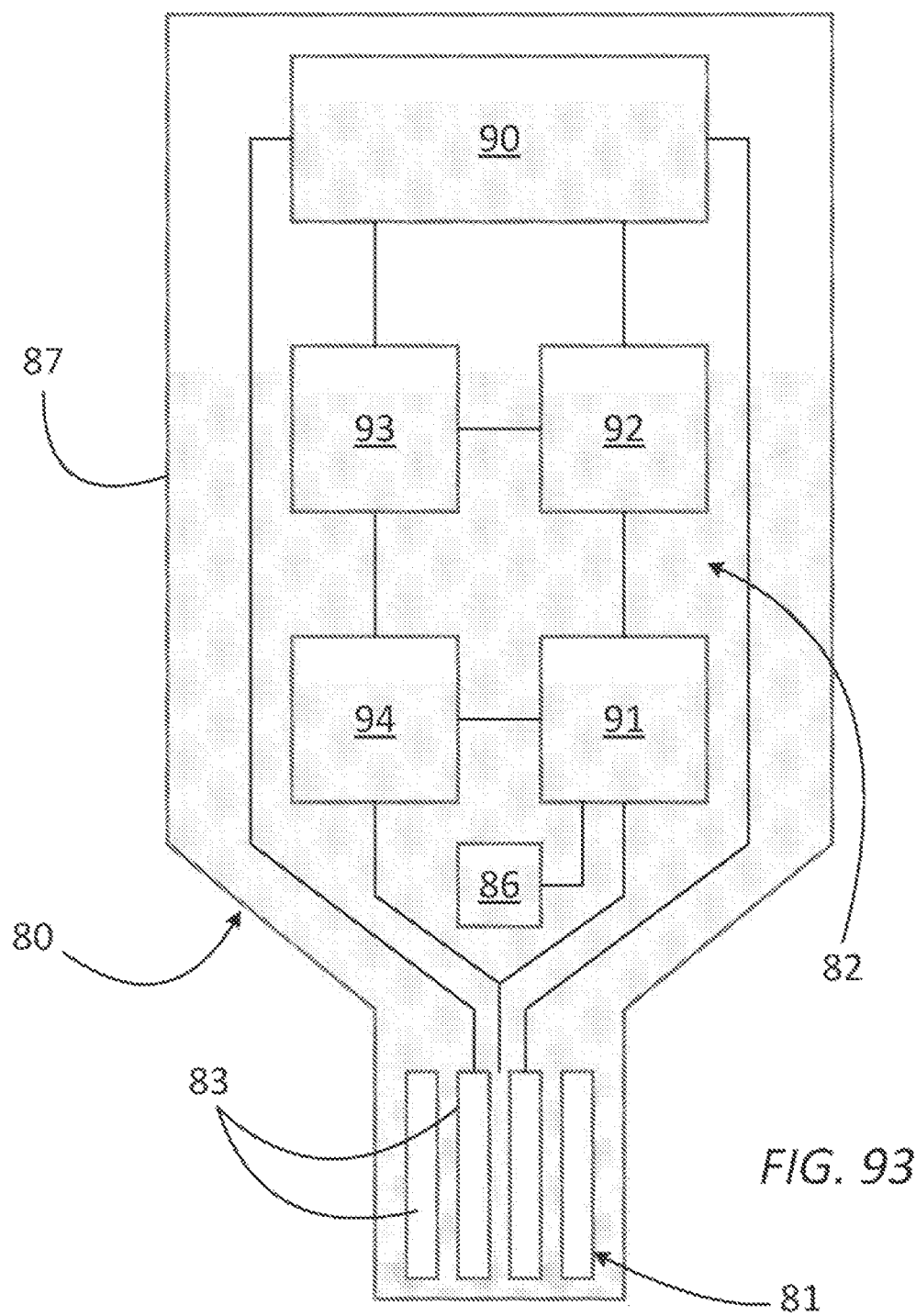
FIG. 93 is a schematic view of another embodiment of an electronic module according to aspects of the disclosure.

An example of an electronic module 80 that is usable in connection with the system 12 and/or the housing assembly 19 is shown in FIGS. 62-64 and 72. As illustrated in FIGS. 62-64 and 72, the module 80 in this embodiment includes a casing 87 that supports an external connector 81 and contains one or more electronic components 82. The external connector 81 may have various configurations depending on the intended usage of the module 80. In the embodiment of FIGS. 62-64 and 72, the connector 81 is a USB-format connector that includes a plurality of terminals 83, which can be connected to a USB port, such as for charging and/or communication with a computer device connected to the port. FIGS. 92 and 93 illustrate embodiments of the module 80 schematically. The electronic components 82 may include at least a power source 90 in one embodiment, and may include additional electronic components, including a processor 91, a memory 92, an input-output device (I/O) 93, a transmitter/receiver (TX/RX) 94, and/or other components as illustrated in FIGS. 92 and 93 and described in greater detail herein. FIG. 92 illustrates one embodiment, where the module 80 is configured for use in supplying power only, and not for data collection, performance monitoring, or communication. In this embodiment, the module 80 includes a power source 90, a processor 91 (which may be in the form of a printed circuit board), and a magnetic sensor 86 as described in greater detail below. Other components, such as a memory, may be included in other embodiments. FIG. 93 illustrates another embodiment, where the module 80 is configured for multiple functions, including supplying power as well as data collection, performance monitoring, and/or communication. In this embodiment, the module 80 additionally includes a memory 92, an I/O 93, and a TX/RX 94. The module 80 may include additional components, such as sensors as described herein which are not illustrated for the sake of simplicity, and it is understood that the module 80 may include further additional or alternate components in other embodiments.

The connector 81 may be connected to one or more electronic components 82 of the module 80. For example, in the embodiment of FIGS. 62-64 and 73, the module 80 is configured for providing electric power output through the connector 81, and the connector 81 is connected to the power source 90 in order to do so, as shown in FIGS. 92 and 93. Additionally, in the embodiment of FIGS. 62-64 and 73, the connector 81 has a plurality of terminals 83 (four in the embodiment shown), and only two of the terminals 83 are actively engaged by the interface 31, such that additional terminals 83 are not engaged. More specifically, in the embodiment of FIGS. 63-75, the interface 31 includes two 34 electrical contacts (power and ground), and when the module 80 of FIGS. 62-64 and 73 is inserted into the housing 20, the power contact 34 engages a first terminal 83 and the ground contact 34 engages a second terminal 83 of the plurality of terminals 83 of the connector 81. In this configuration, the power supply 90 of the module 80 is configured to supply power through the power and ground contacts 34 via the two active terminals 83, and the remainder of the terminals 83 of the connector 81 are inactive or not actively engaged by the interface 31, as illustrated in FIG. 92. This configuration enables the connector 81 to be configured as a USB-format connector that is configured for insertion into a USB port of a computer device, while also functioning to supply power through an interface 31 with only two electrical contacts 34.

In another embodiment, the module 80 may additionally or alternately be configured for transmitting and receiving data, instructions, and other information through the connector 81. The connector 81 in this embodiment may be connected to the processor 91, the memory 92, the TX/RX 94, and/or other components in order to enable this functionality, as shown in FIG. 93. For example, the module 80 and the connector 81 may be configured for receiving data through the interface 31 from other components in communication with the interface, such as a movement sensor (e.g., accelerometer, gyroscope, force sensor, angular rate sensor, compass, etc.), a location-determining device (e.g., GPS), a light (including non-visible light) sensor, a temperature sensor (including ambient temperature and/or body temperature), a sleep pattern sensor, a heart rate monitor, an image-capturing sensor, and/or a moisture sensor, among others. As another example, the module 80 and the connector 81 may also be configured for transmitting instructions through the interface 31 to control other components in communication with the interface 31. As a further example, the module 80 and the connector 81 may be configured for communication through a port on a separate computer device, such as by removal of the module 80 from the housing 20 and insertion of the connector 81 into the port, as described above. It is understood that such communication with other components may be accomplished wirelessly or by use of multiple connectors 81 in other embodiments.

The module 80 may further include one or more buttons 84 that are configured to control operation of the electronic component(s) 82. For example, in the embodiment of FIGS. 62-64, the module 80 includes a single button 84 configured for use as a "power" button, to activate or deactivate the output of the power supply 90 through the connector 81. The casing 87 and the connector 81 of the module 80, and the button 84 if present, may also be sealed against ingress of moisture, which can be particularly advantageous when used in connection with articles 10 for athletic use. In one embodiment, the sealing can be accomplished by ultrasonic welding around any junctures 85 in the casing 87 and around any junctures between the casing 87 and the terminals 83 or the button 84.

Figure 63:
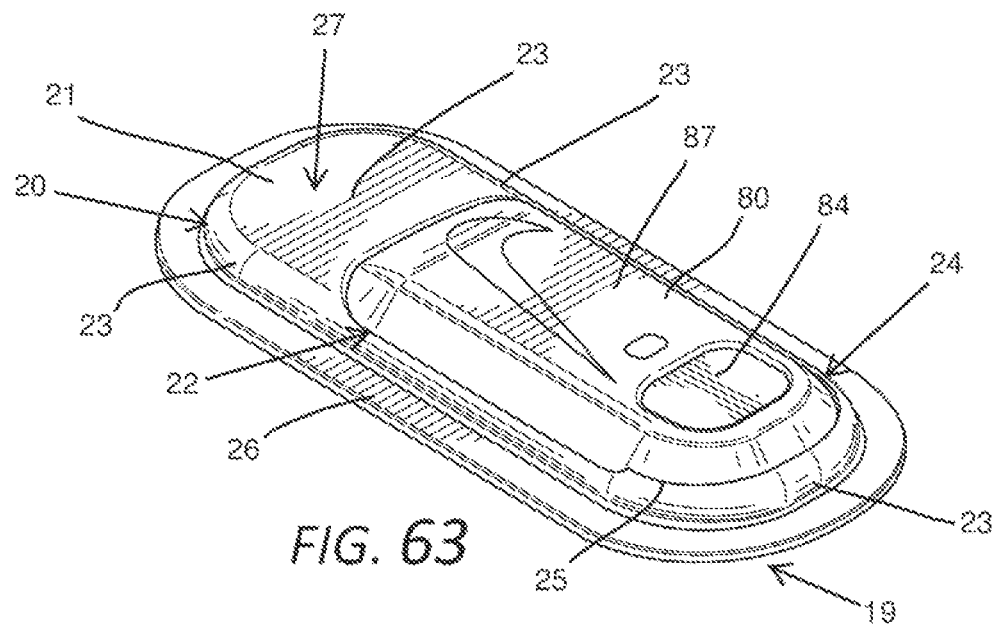
FIG. 63 is a top rear perspective view of the module of FIG. 1 engaged with one embodiment of a housing according to aspects of the present disclosure.
Figure 64:
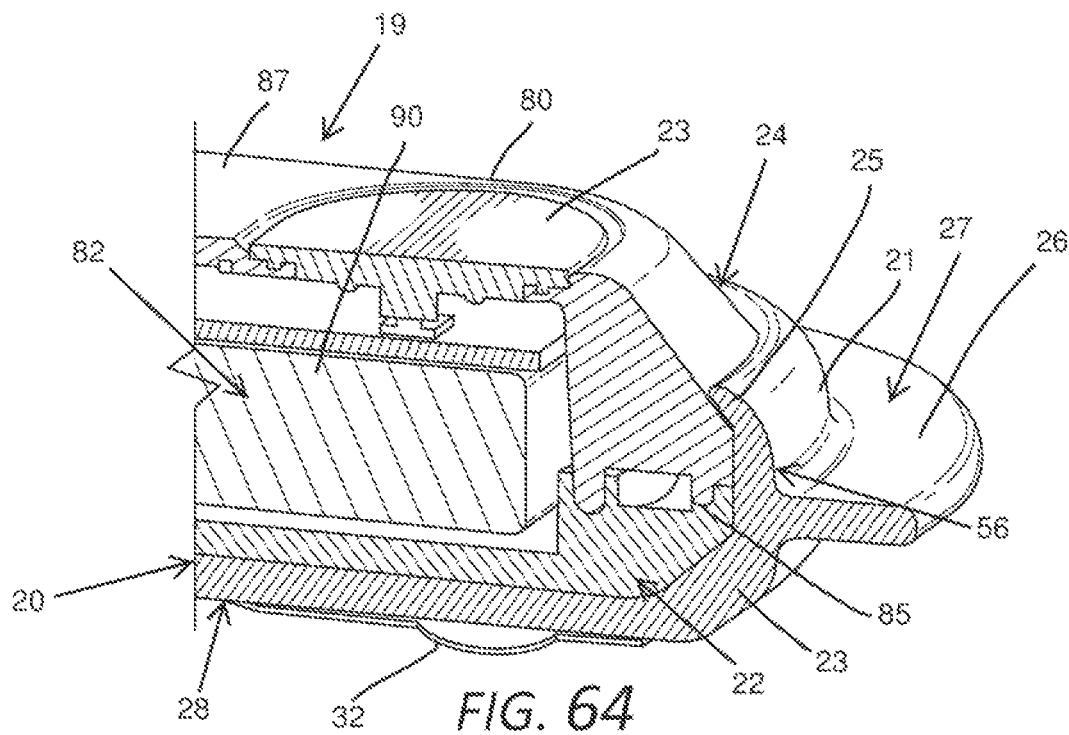
FIG. 64 is a partial cross-sectional view of the housing and the module of FIG. 63.
Figure 65:
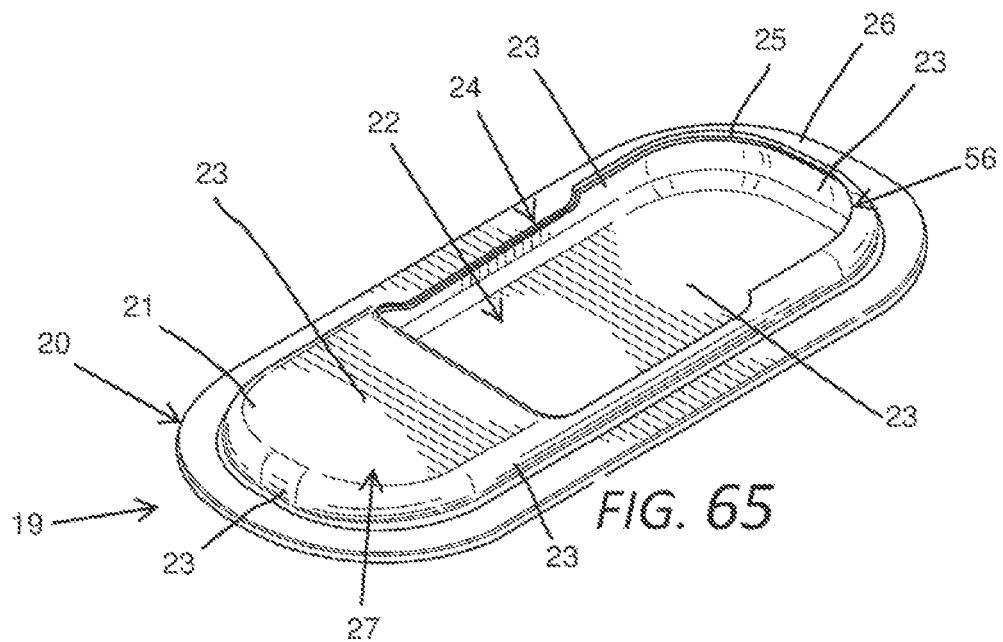
FIG. 65 is a top front perspective view of the housing of FIG. 63.
Figure 66:
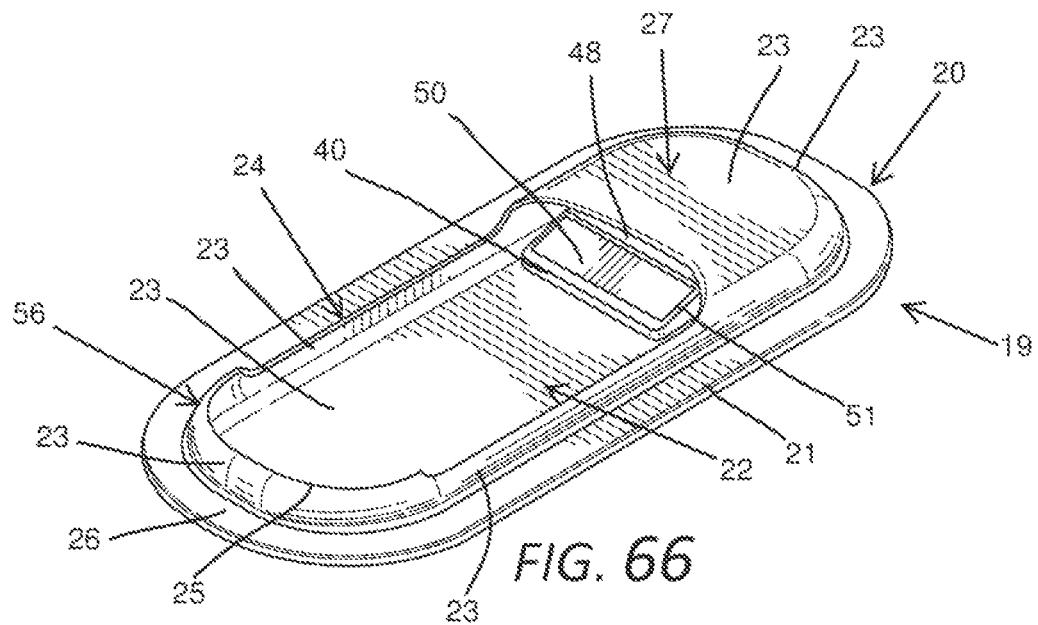
FIG. 66 is a top rear perspective view of the housing of FIG. 63.

The housing 20 includes structures to physically and electronically engage the module 80 when the module 80 is received in the housing 20. The interface 31 and the electrical contacts 34 thereof, which function to physically and electronically engage the connector 81 of the module 80 as described above. The carrier 40 engages the top, bottom, and sides of the end of the connector 81, as shown in FIG. 73. In this configuration, the shelf 46 and the base 48 engage the top and bottom of the connector 81, and the shelf 46, the column 47, and the base 48 combine to define a receiver 57 configured to receive the end of the connector 81. The carrier 40 also has sidewalls 58 that extend between the shelf 46 and the base 48 to further define sides of the receiver 57. The walls 23 of the receptacle 21 also define portions of the receiver 57 in this embodiment, including the walls 23 on the top and bottom sides 27, 28 of the receptacle 21 and the adjacent walls 23 on the sides of the receptacle 21. The base 48 of the carrier 40 and the wall 23 on the bottom side 28 of the receptacle 21 combine to create a ramped surface 59 leading into the receiver 57, and the wall 23 on the top side 27 of the receptacle 21 similarly defines a ramped surface 59, to ease insertion of the connector 81. The receiver 57 and the structures defining the receiver 57 also enclose the connector 81 in order to protect it from inadvertent shorting, dirt, dust, moisture, etc. The lip 25 around at least a portion of the access opening 24, further engages the module 80 to retain the module 80 within the chamber 22, as illustrated in FIGS. 63-64. In this embodiment, the lip 25 extends inwardly around only a portion of the access opening 24, including across the end 56 of the opening 24 opposite the interface 31 and down a portion of each side 24 of the opening 24 adjacent the end 56. Configured in this way, the structures of the carrier 40 and the receptacle 21 around the receiver 57 retain the connector 81 of the module 80 and the lip 25 retains the end of the module 80 opposite the connector 81, thus creating a stable, multi-point retaining structure. In other embodiments, the module 80 may be engaged and retained by the housing 20 in other ways, using different connecting and retaining structure.

The module 80 may be configured with a lockout feature that functions to prevent activation of the terminals 83 of the connector 81 when the module 80 is not engaged with the housing 20 and/or the interface 31. In the embodiment of FIGS. 62-75, the module 80 includes a magnetic sensor 86, such as a Hall effect sensor, that is configured to detect the magnet 50 when in proximity to the magnet 50. The magnetic sensor 86 is shown schematically in FIG. 72, and the magnetic field of the magnet 50 is sufficient such that the magnetic field extends into the chamber 22 and is detectable by the sensor 86 when the module 80 is received in the chamber 22. The module 80 in this embodiment is configured to deactivate the connector 81 when the sensor 86 does not sense the magnet 50 and to activate the connector 81 when the sensor 86 does sense the magnet 50. The module 80 only supplies power from the power source 90 through the terminals 83 when the connector is activated, i.e., when the module 80 is engaged with the housing 20 and the interface 31 thereof. This lockout feature increases safety of the module 80, because a short or shock could occur if a user contacts both of the terminals 83 when the module 80 is active outside the receptacle 21.

The various embodiments of athletic bands and other articles of apparel, housings, and modules described herein provide benefits over existing technology. For example, the configuration of the module and the pocket in which it is received can operate to place physiological sensors in close proximity to the user's skin, which can enhance the ability of such sensors to capture physiological data of the user. As another example, the structures of the band and/or housing described herein can control stretching of the elastic material in order to make pulling the band on and off an appendage quicker and easier; assist in preventing slippage of the band during use; facilitate moisture passage away from the electronic module during use; and increase durability and washability of the band, among other benefits described herein and/or recognized by those skilled in the art. As a further example, the additional input device as described herein provides enhanced ability for communication and interaction with an external device, as well as a simple interface for on-the-go operation of and communication with such an external device by an athlete in the middle of a competition or other athletic event. The various embodiments of manufacturing methods described herein also provide benefits over existing technology. For example, the manufacturing methods for the band as described herein create a durable structure that is efficient to produce. The various methods for operation of the module, the input device, and the external device described herein can enhance the performance monitoring operation of the module and provide enhanced functionality for a user in connection with use of the band and module. Still further benefits are recognizable by those skilled in the art.

Several alternative embodiments and examples have been described and illustrated herein. A person of ordinary skill in the art would appreciate the features of the individual embodiments, and the possible combinations and variations of the components. A person of ordinary skill in the art would further appreciate that any of the embodiments could be provided in any combination with the other embodiments disclosed herein. It is understood that the invention may be embodied in other specific forms without departing from the spirit or central characteristics thereof. The present examples and embodiments, therefore, are to be considered in all respects as illustrative and not restrictive, and the invention is not to be limited to the details given herein. Terms such as "first," "second," "top," "bottom," etc., as used herein, are intended for illustrative purposes only and do not limit the embodiments in any way. Additionally, the term "plurality," as used herein, indicates any number greater than one, either disjunctively or conjunctively, as necessary, up to an infinite number. Further, "providing" an article or apparatus, as used herein, refers broadly to making the article available or accessible for future actions to be performed on the article and does not connote that the party providing the article has manufactured, produced, or supplied the article or that the party providing the article has ownership or control of the article. Accordingly, while specific embodiments have been illustrated and described, numerous modifications come to mind without significantly departing from the spirit of the invention.

What is claimed is:

1. A system comprising:
a wearable article having a top layer and a bottom layer of material forming at least a portion of the wearable article;
a housing assembly comprising a receptacle defining a chamber and having an access opening on a top side of the receptacle providing access to the chamber, such that receptacle is configured to removably receive an electronic module within the chamber by insertion of the electronic module through the access opening, wherein the housing assembly is bonded to the wearable article between the top layer and the bottom layer, such that the top layer and the bottom layer are bonded to the receptacle by a bonding material, the housing assembly further comprising an interface having first and second electrical contacts exposed to the chamber and configured for connection with a connector of the electronic module when the electronic module is received in the receptacle;
a first conductive lead connected to the first electrical contact through a bottom side of the receptacle to place the first conductive lead in electronic communication with the interface; and
a second conductive lead connected to the second electrical contact through the bottom side of the receptacle to place the second conductive lead in electronic communication with the interface.

2. The system of claim 1, wherein the housing assembly further comprises first and second contact members extending from the first and second electrical contacts of the interface through the bottom side of the receptacle, and wherein the first and second conductive leads are connected to the first and second contact members on the bottom side of the receptacle.

3. The system of claim 2, wherein the first and second contact members are mounted on a carrier received in a cavity in the receptacle, such that the carrier is engaged with the receptacle and supports the first and second electrical contacts to form the interface.

4. The system of claim 1, further comprising an electrically-powered component connected to the wearable article, wherein the first and second conductive leads are connected to the electrically-powered component and are configured to provide power from the electronic module to power the electrically-powered component.

5. The system of claim 1, wherein the housing assembly further comprises a carrier engaged with the receptacle and at least partially positioned within the chamber, wherein the carrier supports the first and second electrical contacts within the chamber to form the interface.

6. The system of claim 5, wherein the carrier has a shelf extending forward into the chamber, a column depending from the shelf, and a base connected to the column and positioned proximate to the bottom side of the receptacle, wherein the shelf supports the first and second electrical contacts within the chamber to form the interface.

7. The system of claim 6, wherein the shelf has a first slot and a second slot receiving the first and second electrical contacts to support the first and second electrical contacts within the chamber.

8. The system of claim 5, wherein the receptacle has an opening on the bottom side, and the first and second conductive leads are connected to the first and second electrical contacts through the opening, and wherein a portion of the carrier is positioned within the opening.

9. The system of claim 1, wherein the receptacle has a flange extending outwardly around at least a portion of a periphery of the receptacle, and wherein the flange is received between the top layer and the bottom layer, and the top layer and the bottom layer are bonded to the flange by the bonding material.

10. A system comprising:
a wearable article having a top layer and a bottom layer of material forming at least a portion of the wearable article;
a housing assembly comprising a receptacle defining a chamber and having an access opening on a top side of the receptacle providing access to the chamber, such that receptacle is configured to removably receive an electronic module within the chamber by insertion of the electronic module through the access opening, wherein the housing assembly is bonded to the wearable article between the top layer and the bottom layer, such that the top layer and the bottom layer are bonded to the receptacle by a bonding material, the housing assembly further comprising an interface having a plurality of electrical contacts exposed to the chamber and configured for connection with a connector of the electronic module when the electronic module is received in the receptacle;
a plurality of conductive leads connected to the electrical contacts through a bottom side of the receptacle to place the conductive leads in electronic communication with the interface; and
an electrically-powered component connected to the wearable article, wherein the conductive leads are connected to the electrically-powered component.

11. The system of claim 10, wherein the conductive leads are configured to provide power from the electronic module to power the electrically-powered component.

12. The system of claim 10, wherein the housing assembly further comprises a plurality of contact members extending from the electrical contacts of the interface through the bottom side of the receptacle, and wherein the conductive leads are connected to the contact members on the bottom side of the receptacle.

13. The system of claim 12, wherein the contact members are mounted on a carrier received in a cavity in the receptacle, such that the carrier is engaged with the receptacle and supports the electrical contacts to form the interface.

14. The system of claim 10, wherein the housing assembly further comprises a carrier engaged with the receptacle and at least partially positioned within the chamber, wherein the carrier supports the electrical contacts within the chamber to form the interface.

15. The system of claim 14, wherein the carrier has a shelf extending forward into the chamber, a column depending from the shelf, and a base connected to the column and positioned proximate to the bottom side of the receptacle, wherein the shelf supports the electrical contacts within the chamber to form the interface.

16. The system of claim 15, wherein the shelf has slots receiving the electrical contacts to support the electrical contacts within the chamber.

17. The system of claim 14, wherein the receptacle has an opening on the bottom side, and the conductive leads are connected to the electrical contacts through the opening, and wherein a portion of the carrier is positioned within the opening.

18. The system of claim 10, wherein the receptacle has a flange extending outwardly around at least a portion of a periphery of the receptacle, and wherein the flange is received between the top layer and the bottom layer, and the top layer and the bottom layer are bonded to the flange by the bonding material.

19. A system comprising:
a wearable article having a top layer and a bottom layer of material forming at least a portion of the wearable article;
a housing assembly comprising a receptacle defining a chamber and having an access opening on a top side of the receptacle providing access to the chamber, such that receptacle is configured to removably receive an electronic module within the chamber by insertion of the electronic module through the access opening, wherein the housing assembly is bonded to the wearable article between the top layer and the bottom layer, such that the top layer and the bottom layer are bonded to the receptacle by a bonding material, the housing assembly further comprising an interface having a plurality of electrical contacts exposed to the chamber and configured for connection with a connector of the electronic module when the electronic module is received in the receptacle,
wherein the housing assembly further comprises a carrier engaged with the receptacle and at least partially positioned within the chamber, wherein the carrier has a shelf extending forward into the chamber to support the electrical contacts within the chamber to form the interface, a column depending from the shelf, and a base connected to the column and positioned proximate to a bottom side of the receptacle; and
a plurality of conductive leads connected to the electrical contacts through the bottom side of the receptacle to place the conductive leads in electronic communication with the interface.

20. The system of claim 19, wherein the shelf has slots receiving the electrical contacts to support the electrical contacts within the chamber.

21. The system of claim 19, wherein the receptacle has a flange extending outwardly around at least a portion of a periphery of the receptacle, and wherein the flange is received between the top layer and the bottom layer, and the top layer and the bottom layer are bonded to the flange by the bonding material.

22. The system of claim 19, wherein the receptacle has an opening on the bottom side, and the conductive leads are connected to the electrical contacts through the opening, and wherein a portion of the carrier is positioned within the opening.

\* \* \* \* \*